United States Patent [19]

Somerville et al.

[11] Patent Number: 5,668,292

[45] Date of Patent: Sep. 16, 1997

[54] USE OF PLANT FATTY ACYL HYDROXYLASES TO PRODUCE HYDROXYLATED FATTY ACIDS AND DERIVATIVES IN PLANTS

[75] Inventors: Chris Somerville, Portola Valley, Calif.; Frank van de Loo, Lexington, Ky.

[73] Assignee: Carnegie Institution of Washington, Washington, D.C.

[21] Appl. No.: 314,596

[22] Filed: Sep. 26, 1994

[51] Int. Cl.$^6$ .......................... A01H 5/00; C12N 15/29; C12N 15/82

[52] U.S. Cl. .................. 800/205; 800/DIG. 69; 435/172.1; 536/23.6; 530/377

[58] Field of Search ................... 435/172.1, 172.3, 435/240.4; 800/205, DIG. 69; 536/23.6; 530/377

[56] References Cited

FOREIGN PATENT DOCUMENTS 9411516  5/1994  WIPO.

OTHER PUBLICATIONS

Altschul et al, J. Mol. Biol., 215:403–410 (1990).
Arondel et al, Science, 258:1353–1355 (1992).
Atsmon et al, Castor, McGraw-Hill, New York pp. 438–447 (1989).
Bafor et al, Biochem., 280:507–514 (1991).
Battey et al, Plant Physiol., 90:835–840 (1989).
Bechtold et al, C.R. Acad. Sci. Paris, 316:1194–1199 (1993).
Beltz et al, Methods in Enzymology, 100:266–285 (1983).
Bray et al, Planta, 172:364–370 (1987).
Browse et al, Ann. Rev. Plant Physiol. Plant Mol. Biol., 42:467–506 (1991).
Canvin, Can. J. Biochem. Physiol., 41:1879–1885 (1963).
Ditta et al, Proc. Natl. Acad. Sci. USA, 77:7347–7351 (1980).
Fox et al, Proc. Natl. Acad. Sci., 90:2486–2490 (1993).
Galliard et al, J. Biol. Chem., 241:5806–5812 (1966).
Gould et al, Proc. Natl. Acad. Sci. USA, 86:1934–1938 (1989).
Greenwood et al, Can. J. Bot., 60:1751–1760 (1982).
Gunstone et al, The Lipid Handbook, Chapman and Hall, London, Chapters 1.9, pp. 19–20 and 3.3.5, pp. 57–58 (1986).
Howling et al, Biochim. Biophys. Acta, 260:10–19 (1972).
Huyuh t al, DNA Cloning, vol. 1: A Practical Approach, (ed) D.M. Glover, IRL Press, Washington, D.C., pp. 49–77 (1985).
Iba et al, J. Biol. Chem., 268:24099–24105 (1993).
James et al, Biochem. J., 95:448–452 (1965).
Kearns et al, Arch. Biochem. Biophys., 284:431–436 (1991).
Knuzton et al, Proc. Natl. Acad. Sci. USA, 89:2624–2628 (1992).
Kok et al, J. Biol. Chem., 264:5435–5441 (1989).
Konez et al, Mol. Gen. Genet., 204:383–396 (1986).
Kren et al, Experentia, 41:1476–1477 (1985).
Miquel et al, J. Biol. Chem., 267:1502–1509 (1992).
Moreau et al, Plant Physiol., 67:672–676 (1981).
Morris, Biochem. Biophys. Res. Commun., 29:311–315 (1967).
Morris, Biochem. J., 118:681–693 (1970).
Morris et al, Biochem. J., 100:29c–30c (1966).
Newman et al, Plant Cell, 5:701–714 (1993).
Okuley et al, Plant Cell, 6:147–158 (1994).
Ooms et al, Plasmid, 7:15–29 (1982).
Panaccione et al, Gene, 86:163–170 (1990).
Prasad et al, J. Am. Oil. Chem. Sos., 64:1424–1427 (1987).
Puissant et al, BioTechniques, 8:148–149 (1990).
Sambrook et al, Molecular Cloning: a Laboratory Manual, 2nd ed., Cold Spring Harbor Laboratory Press (1989).
Schmidt et al, American Society of Plant Physiologists, pp. 40–49 (1993).
Smith, Fatty Acids, Pryde E.H., Ed., American Oil Chemists' Society, Champaign, 2nd ed., pp. 29–47.
Smith et al, Biochem. J., 287:141–144 (1992).
Suzuki et al, J. Bacteriol., 173:1690–1695 (1991).
Thiede et al, J. Biol. Chem., 261:13230–13235 (1986).
van de Loo et al, Lipid Metabolism in Plants, T.S. Moore Jr., Ed., CRC Press, Boca Raton, pp. 91–126 (1993).
van de Loo et al, Plant Physiol., 105:443–444 (1994).
von Heijne, J. Mol. Biol., 184:99–105 (1985).
Yadav et al, Plant Physiol., 103:467–476 (1993).
Topfer et al 1995 Science 268:681–686.
Ohlrogge et al 1994 (Nov.) Plant Physiol 104: 821–826.
Kridl et al 1993 In Control of Plant Gene Expression, CRC Press, Verma (ed.) pp. 481–498.
Post–Beittenmiller et al 1993 ibid pp. 157–174.
Bafor et al 1991 Biochem Journal 280: 507–514.
Carlson et al 1990 J Am Oil Chem Soc 67(8): 495–498.
McKean et al 1994 (May) Plant Physical 105 (1): 64.

*Primary Examiner*—Patricia R. Moody
*Attorney, Agent, or Firm*—Cushman Darby & Cushman IP Group of Pillsbury Madison & Sutro

[57] ABSTRACT

The present invention relates to the identification of nucleic acid sequences and constructs, and methods related thereto, and the use of these sequences and constructs to produce genetically modified plants for the purpose of altering the composition of plant oils, waxes and related compounds.

14 Claims, 27 Drawing Sheets

FIG. 4

TGACCTCGGAATCTTTGCCACAACGTTTGTGCTTTATCAGGCTACAATGGCAAAAGG
GTTGGCTTGGGTAATGCGTATCTATGGGGTGCCATTGCTTATTGTTAACTGTTTCCTT
GTTATGATCACATACTTGCAGCACACTCACCCAGCTATTCCACGCTATGGCTCATCG
GAATGGGATTGGCTCCGGGGAGCAATGGTGACTGTCGATAGAGATTATGGGGTGTT
GAATAAAGTATTCCATAACATTGCAGNCACTCATGTAGCTCATCANCTCTTTGCTAC
AGTGNCACATTACCATGCAATGGGGNCNCTAAGCAATCAAGGCCTATAATGGGNG
GATNTTACCGGATNATNGGNCCCCATTTACAAGGGATTTTTGGGGGGCAAANNNAG
TCNTTTTNTNCTGGCCAATTAAGGGGNCTCAAAAAGGGTTTNTTGGCCCGCAAGTTT
AAAAGGNATTTGNCNGTTTTTAGGGNGGATTTNCCAAAGGATTTTTTTNGGAATTNT
NTTTNAGGGGGG

FIG. 5

CTGACCTCGGAATCTTTGCCACAACGTTTGTCCTTTATCAGGCTACAATGGCAAAAG
GGTTGGCTTGGGTAATGCGTATCTATGGGGTGCCATTGCTTATTGTTAACTGTTTCCT
TGTTATGATCACATACTTGCAGCACACTCACCCAGCTATTCCACGCTATGGCTCATC
GGAATGGGATTGGCTCCGGGGAGCAATGGTGACTGTCGATAGAGATTATGGGGTGT
TGAATAAAGTATTCCATAACATTGCAGACACTCATGTAGCTCATCATCTCTTTGCTA
CAGTGCCACATTACCATGCAATGGAGGCCACTAAAGCAATCAAGCCTATAATGGGT
GAGTATTACCGGTATGATGGTNCCCATTTTACAAGGCATTGTGGAGGGAGCAAAGG
AGTCTTNCCGNCGGCCAANTGAGNNGNCNCANAAGNGGTTTTGGCCCGACAAGTTT
AAAAGGCATNNCCTGTTTTNAGGGGGATTNCAANAGGATTTTTNNGGAATNGCTTT
NGGGNAAAANCAGCATTGNGTTAAGGNNGC

FIG. 6A

```
Sequences producing High-scoring Segment Pairs:           Reading  High   Smallest
                                                                                  Poisson
                                                          Reading  High   Probability
                                                          Frame    Score  P(N)       N gp|D14410|VIRARG1_1  ORF [Vigna radiata]                    +2     110    2.7e-16   3
gp|L01418|BNALINDES_1 linoleic acid desaturase [Brassi..    +2     112    3.2e-13   3
sp|P18395|UNR_RAT    UNR PROTEIN.>pir|S11210|S11210  ....   -3      55    0.72      1
gp|S55996|S55996_1   NRU gene product [human]               -3      55    0.72      1
pir|S27270|S27270    Prohormone convertases - Great p...    +1      55    0.82      1

>gp|D14410|VIRARG1_1 ORF [Vigna radiata] Length = 380
  Plus Strand HSPs:

Score = 110 (52.1 bits), Expect = 6.0e-08, P = 4.7e-08
Identities = 19/40 (47%), Positives = 25/40 (62%), Frame = +2

Query:  152 IPRYGSSEWDWLRGAMVTVDRDYGVLNKVFHNIAXTHVAH 271
            +P Y   EW +LRG + TVDRDYG +N V H+I   + H
Sbjct:  265 LPWYRGQEWSYLRGGLTTVDRDYGWINNVHHDIGTHVIHH 304

Score = 84 (39.8 bits), Expect = 0.00038, Poisson P(2) = 3.6e-13
Identities = 14/37 (37%), Positives = 21/37 (56%), Frame = +2

Query:  242 HNIAXTHVAHXLFATVXHYHAMGXXKQSRPIMGGXYR 352
            H+    THV H LF   + HYH  +   K ++  ++G   YR
Sbjct:  294 HHDIGTHVIHHLFPQIPHYHLVEATKSAKSVLGKYYR 330

Score = 70 (33.2 bits), Expect = 0.041, Poisson P(3) = 2.7e-16
Identities = 14/37 (37%), Positives = 23/37 (62%), Frame = +2

Query:   29 VLYQATMAKGLAWVMRIYGVPLLIVNCFLVMITYLQH 139
            VL  ++  G  ++++YGVP LI     +L  +TYL H
Sbjct:  222 VLLYLSLTIGPIFMLKLYGVPYLIFVMWLDFVTYLHH 258
```

FIG. 6B

>gp|L01418|BNALINDES_1 Linoleic acid desaturase [Brassica napus] Length = 383
Plus Strand HSPs:

Score = 112 (53.0 bits), Expect = 3.0e-08, P = 2.4e-08
Identities = 17/40 (42%), Positives = 25/40 (62%), Frame = +2

```
Query:  152 IPRYGSSEWDWLRGAMVTVDRDYGVLNKVFHNIAXTHVAH 271
            +P Y   EW +LRG +    T+DRDYG+ N + H+I   + H
Sbjct:  266 LPWYRGKEWSYLRGGLTTIDRDYGIFNNIHHDIGTHVIHH 305
```

Score = 80 (37.9 bits), Expect = 0.0014, Poisson P(2) = 5.5e-12
Identities = 13/37 (35%), Positives = 21/37 (56%), Frame = +2

```
Query:  242 HNIAXTHVAHXLFATVXHYHAMGXXKQSRPIMGGXYR 352
            H+    THV H LF  + HYH  +   + ++G  YR
Sbjct:  295 HHDIGTHVIHHLFPQIPHYHLVDATRAAKHVLGRYYR 331
```

Score = 63 (29.8 bits), Expect = 0.43, Poisson P(3) = 3.2e-13
Identities = 11/24 (45%), Positives = 17/24 (70%), Frame = +2

```
Query:   68 VMRIYGVPLLIVNCFLVMITYLQH 139
            V+++YGVP +I  +L  +TYL H
Sbjct:  236 VLKVYGVPYIIFVMWLDAVTYLHH 259
```

FIG. 7A

```
Query= crs834 61-600 (540 letters)
Translating both strands of query sequence in all 6 reading frames Database: Non-redundant PDB+SwissProt+PIR+SPupdate+GenPept+GPupdate, 5:08 AM
         EDT Jul 22, 1993
         95,852 sequences; 26,878,909 total letters.

Smallest
                                                                    Poisson
                                                Reading  High       Probability
Sequences producing High-scoring Segment Pairs:  Frame   Score      P(N)       N pir|A44227|A44227    omega-3 fatty acid desaturase,...    +3   126   6.8e-21  2
gp|D14410|VIRARG1_1  ORF [Vigna radiata] >gp|D14410|...   +3   131   2.7e-20  2
gp|M64253|HUMMHAKKA_1 HLA-A gene product [Homo sapiens]   -3    56   0.61     1
gp|M64254|HUMMHBKKA_1 HLA-B gene product [Homo sapiens]   -3    56   0.61     1
gp|M64257|HUMMHAJHA_1 HLA-A gene product [Homo sapiens]   -3    56   0.61     1

>pir|A44227|A44227 omega-3 fatty acid desaturase, omega-3 linoleate desaturase
         - rape | 0.0 0.0 0.0 0.0 0.0 >gp|L01418|BNALINDES_1 linoleic acid
         desaturase [Brassica napus] Length = 383

Plus Strand HSPs:

Score = 126 (60.6 bits), Expect = 2.5e-10, P = 2.5e-10
Identities = 20/37 (54%), Positives = 27/37 (72%), Frame = +3

Query:   243 HNIADTHVAHHLFATVPHYHAMEATKAIKPIMGEYYR 353
             H+      THV HHLF  +PHYH  ++AT+A K  +G YYR
Sbjct:   295 HHDIGTHVIHHLFPQIPHYHLVDATRAAKHVLGRYYR 331

Score = 111 (53.4 bits), Expect = 6.8e-21, Poisson P(2) = 6.8e-21
Identities = 17/40 (42%), Positives = 25/40 (62%), Frame = +3

Query:   153 IPRYGSSEWDWLRGAMVTVDRDYGVLNKVFHNIADTHVAH 272
             +P Y   EW +LRG + T+DRDYG+ N + H+I    + H
Sbjct:   266 LPWYRGKEWSYLRGGLTTIDRDYGIFNNIHHDIGTHVIHH 305

Score = 63 (30.3 bits), Expect = 1.3e-12, Poisson P(3) = 1.3e-12
Identities = 11/24 (45%), Positives = 17/24 (70%), Frame = +3
```

FIG. 7B

```
Query:  69 VMRIYGVPLLIVNCFLVMITYLQH 140
           V+++YGVP +I    +L  +TYL H
Sbjct: 236 VLKVYGVPYIIFVMWLDAVTYLHH 259

>gp|D14410|VIRARG1_1 ORF [Vigna radiata] >gp|D14410|VIRARG1_1 ORF [Vigna radiata] Length = 380
 Plus Strand HSPs:

Score = 131 (63.0 bits), Expect = 4.4e-11, P = 4.4e-11
 Identities = 21/37 (56%), Positives = 28/37 (75%), Frame = +3

Query: 243 HNIADTHVAHHLFATVPHYHAMEATKAIKPIMGEYYR 353
           H+   THV HHLF  +PHYH  +EATK+ K ++G+YYR
Sbjct: 294 HHDIGTHVIHHLFPQIPHYHLVEATKSAKSVLGKYYR 330

Score = 109 (52.4 bits), Expect = 2.7e-20, Poisson P(2) = 2.7e-20
 Identities = 19/40 (47%), Positives = 25/40 (62%), Frame = +3

Query: 153 IPRYGSSEWDWLRGAMVTVDRDYGVLNKVFHNIADTHVAH 272
           +P Y   EW +LRG +  TVDRDYG +N V H+I    + H
Sbjct: 265 LPWYRGQEWSYLRGGLTTVDRDYGWINNVHHDIGTHVIHH 304

Score = 70 (33.7 bits), Expect = 9.5e-16, Poisson P(3) = 9.5e-16
 Identities = 14/37 (37%), Positives = 23/37 (62%), Frame = +3

Query:  30 VLYQATMAKGLAWVMRIYGVPLLIVNCFLVMITYLQH 140
           VL  ++  G  +++++YGVP LI  +L  +TYL H
Sbjct: 222 VLLYLSLTIGPIFMLKLYGVPYLIFVMWLDFVTYLHH 258
```

FIG. 8A

```
                         10        20        30        40        50        60
PCRS677.DNA  TGACCCTCGGAATCTTTGCCACAACGTTTGTGCTTTATCAGGCTACAATGGCAAAAGGGTT
             ||||||||||||||||||||||||||||||||  ||||||||||||||||||||||||||
PCRS834.DNA  TGACCCTCGGAATCTTTGCCACAACGTTTGTCCTTTATCAGGCTACAATGGCAAAAGGGTT
                         10        20        30        40        50        60

70        80        90       100       110       120
PCRS677.DNA  GGCTTGGGTAATGCGTATCTATGGGGTGCCATTGCTTATTGTTAACTGTTTCCTTGTTAT
             |||||||||||||||||||||||||||||||||||||||||||||||||||||||||||
PCRS834.DNA  GGCTTGGGTAATGCGTATCTATGGGGTGCCATTGCTTATTGTTAACTGTTTCCTTGTTAT
                         70        80        90       100       110       120

130       140       150       160       170       180
PCRS677.DNA  GATCACATACTTGCAGCACACTCACCCAGCTATTCCACGCTATGGCTCATCGGAATGGGA
             ||||||||||||||||||||||||||||||||||||||||||||||||||||||||||||
PCRS834.DNA  GATCACATACTTGCAGCACACTCACCCAGCTATTCCACGCTATGGCTCATCGGAATGGGA
                        130       140       150       160       170       180

190       200       210       220       230       240
PCRS677.DNA  TTGGCTCCGGGGAGCAATGGTGACTGTCGATAGAGATTATGGGGTGTTGAATAAAGTATT
             ||||||||||||||||||||||||||||||||||||||||||||||||||||||||||||
PCRS834.DNA  TTGGCTCCGGGGAGCAATGGTGACTGTCGATAGAGATTATGGGGTGTTGAATAAAGTATT
                        190       200       210       220       230       240

250       260       270       280       290       300
PCRS677.DNA  CCATAACATTGCAGNCACTCATGTAGCTTCATCANCTCTTTGCTACAGTGNCACATTACCA
             ||||||||||||||   ||||||||||||||||| ||||||||||||||| ||||||||
PCRS834.DNA  CCATAACATTGCAGACACTCATGTAGCTTCATCATCTCTTTGCTACAGTGCCACATTACCA
                        250       260       270       280       290       300
```

FIG. 8B

```
                    310        320        330        340        350
PCRS677.DNA  TGCAATGGGGNCNCT-AAGCAATCAAGGCCTATAATGGGNGGATNTTACCGG-ATNATN
             ||||||||| | ||  || |||||||||| ||||||||||| |||||| |||||| ||||||
PCRS834.DNA  TGCAATGGAGGCCACTAAAGCAATCAA-GCCTATAATGGGTGAGTATTACCGGTATGATG
                    310        320        330        340        350        360

370        380        390        400        410
PCRS677.DNA  GGNCCCCATTTACAAGGGGATTTTTGGGGGCAAANNNAGTCNTTTTNTNTNCTGGCCAATTA
             || |||||||||||| ||||| |||  || ||||||| |||| |||  |||  ||||||||
PCRS834.DNA  GTNCCCCATTTACAAGGAGCATTGTGTGGAGGAGCAAAGGAGTC--TTNCCGNCGGCCAANTG
                    370        380        390        400        410

430        440        450        460        470
PCRS677.DNA  AGGGGNCTCAAAAAGGGTTTNTTGGCCCG-CAAGTTTAAAAGGNATTTGNCNGTTTTTAG
             ||||| |||||||||||| || |||||||  |||||||||||||| |||| | |||| ||
PCRS834.DNA  AGNNGNCNCANAAGNGGTTT--TGGCCCGACAAGTTTAAAAGGCA-TNNCCTGTTTTNAG
                    430        440        450        460        470

490        500        510        520
PCRS677.DNA  GGNGGATTTNCCAAAGGATTTTTTTNGGAATTNTNTTTNAGGGGGG
             ||  |||  | |||| |||| |||||| ||||  |||  |||  ||
PCRS834.DNA  GG-GGA-TTNCAANAGGA-TTTTTNNGGAATNGCTTTNGGGGNAAA
                    490        500        510
```

FIG. 9

```
            210        220        230        240        250
3cvii    234 ACTTGGTGAT GATAGTTCCG GTTATAGCAA ATCCGACCAA AAACGGCCAG 283
3civ-1    79 CACACTTGGT GACCTCAAAT CAAACACCAC ACCTTATAAC TTAGTCTTAA 128
4cviii-1  -6 ---------- ---------- ---------- ---------- -----TTAA  -7
3cx-3    -56 ---------- ---------- ---------- ---------- ----------  31
3ci      -19 ---------- ---------- ---------- ---------- ----------  54
4av        5 ---------- ---------- ---------- ---------- ----------  52
2cii       3 ---------- ---------- ---------- ---------- ----------  10
3cix     -40 ---------- ---------- ---------- ---------- ----------  19
4avii    -31 ---------- ---------- ---------- ---------- ----------  53
2ciii-4    4 ---------- ---------- ---------- ---------- ----------

260        270        280        290        300
3cvii    284 TTACGGTTGA ACTCCCGCTT GAAGAACACG GGCCATGGAT CGAACCACCT 333
3civ-1   129 GAGAGAGAGA GAGAGAGAGG AGACATTTCT CTTCTCTGAG ATAAGCACTT 178
4cviii-1  45 GAGAGAGAGA GAGAGAGAGG AGACATTTCT CTTCTCTGAG ATAAGCACTT  94
3cx-3     -6 ---------- ---------- ---------- -----CTCT ------TT   44
3ci       32 ---------- ---------- ---------- ---------- AAAGGCACTT  81
4av       55 ---------- GAGAGAGAGG AGACATTTCT CTTCTCTGAG ATAAGCACTT 104
2cii      53 ---------- ----AGG    AGACACTTCT CTTCTCTGAG ATAAGCACTT 102
3cix      11 ---------- ---------- ---------- ---------- ---------  60
4avii     20 ---------- ---------- ---------- ---------- ---ACTT    69
2ciii-4   54 ---------- ---------- -GACATTTCT CTTCTCTGAG ATAAGCACTT 103

310        320        330        340        350
3cvii    334 TTTCATCTTT TCTCGAAGCC TCAGGAAAGT GTTTAAAAAA GAGCTTTAGA 383
3civ-1   179 CTCTTCCAGA CATCGAAGCC TCAGGAAAGT GCTTAAAAAG AGCTTAAGAA 228
4cviii-1  95 CTCTTCCAGA CATCGAAGCC TCAGGAAAGT GCTTAAAAAG AGCTTAAGAA 144
3cx-3     45 CTCTTCCAGA CATCGAAGCC TCAGGAAAGT GCTTAAAAAG AGCTTAAGAA  94
3ci       82 CTCTTCCAGA CATCGAAGCC TCAGGAAAGT GCTTAAAAAG AGCTTAAGAA 131
4av      105 CTCTTCCAGA CATCGAAGCC TCAGGAAAGT GCTTAAAAAG AGCTTAAGAA 154
2cii     103 CTCTTCCAGA CATCGAAGCC TCAGGAAAGT GCTTAAAAAG AGCTTAAGAA 152
3cix      61 -----CAGA CATCGAAGCC TCAGGAAAGT GCTTAAAAAG AGCTTAAGAA 110
4avii     70 CTCTTCCAGA CATCGAAGCC TCAGGAAAGT GCTTAAAAAG AGCTTAAGAA 119
2ciii-4  104 CTCTTCCAGA CATCGAAGCC TCAGGAAAGT GCTTAAAAAG AGCTTAAGAA 153
```

FIG. 10A

```
  1  GCC ACC TTA AGC GAG CGC CGC ACA CGA AGC CTC CTT TCA CAC TTG GTG ACC TCA AAT CAA
 61  ACA CCA CAC CTT ATA ACT TAG TCT TCT AGA GAG AGA AGA AAA GGA GAC ATT TCT CTT
121  CTC TGA GAT AAG CAC TTC TCT TCC AGA CAT CGA AGC CTC AGG AAA AGC CTT AAA AAG AGC
        M   G   G   G   G   R   M   S   T   V   I   T   S   N   N   T
181  TTA AGA ATG GGA GGT GGT CGC ATG TCT ACT GTC ATA ACC AGC AAC AAC GTG ACC GAG AAG
 19  K   G   G   S   S   H   L   K   R   A   P   H   T   K   K   P   F   L   G
241  AAA GGA GGA AGC AGC CAC CTT AAG CGA GCG CCG CAC ACG AAG AAG CCT TTC ACA CTT GGT
 39  D   L   K   R   A   I   P   P   H   C   F   E   R   S   L   V   R   S   F   S
301  GAC CTC AAG AGA GCC ATC CCA CCA CAT TGC TTT GAA CGC TCT CTT GTG CGC TCA TTC TCC
 59  Y   V   A   Y   D   V   C   L   S   L   F   Y   I   A   T   N   F   F
361  TAT GTT GCC TAT GAT GTC TGC TTA AGT CTT TTC TAC TCG ATC GCC ACC AAC TTC TTC
 79  P   Y   I   S   S   P   L   S   Y   V   A   W   L   V   Y   W   L   F   Q   G
421  CCT TAC ATC TCT TCT CCG CTC TCG TAT GTC GCT TGG CTG GTT TAC TGG CTC TTC CAA GGC
 99  C   I   L   T   G   L   W   V   I   G   H   E   C   G   H   S   A   F   S   E
481  TGC ATT CTC ACT GGT CTT TGG GTC ATC GGC CAT GAA TGT GGC CAT TCT GCA TTT AGT GAG
119  Y   Q   L   A   D   D   I   V   G   L   I   V   H   S   A   L   L   V   P   Y
541  TAT CAG CTG GCT GAT GAC ATT GTT GGC CTA ATT GTC CAT TCT GCA CTT CTG GTT CCA TAT
139  F   S   W   K   Y   S   H   R   R   H   H   S   N   I   G   S   L   E   R   D
601  TTT TCA TGG AAA TAT AGC CAT CGC CGC CAC CAT TCT AAC ATA GGA TCT CTC GAG CGA GAC
159  E   V   F   V   P   K   S   K   S   K   I   S   W   Y   S   K   Y   S   N   N
661  GAA GTG TTC GTC CCG AAA TCA AAG TCG AAA ATT TCA TGG TAT TCT AAG TAC TCA AAC AAC
179  P   P   G   R   V   L   T   L   A   A   T   L   L   L   G   W   P   L   Y   L
721  CCG CCA GGT CGA GTT TTG ACA CTT GCT GCC ACG CTC CTC CTC GGC TGG CCT TTA TAC TTA
199  A   F   N   V   S   G   R   P   Y   D   R   F   A   C   H   Y   D   P   Y   G
781  GCT TTC AAT GTC TCT GGT AGA CCT TAC GAT CGC TTT GCT TGC CAT TAT GAT CCC TAT GGC
```

FIG. 10B

```
219  P   I   F   S   E   R   L   Q   I   Y   I   A   D   L   G   I   F   A
841  CCA ATA TTT TCC GAA AGA CTT CAG ATT TAC ATT GCT GAC CTC GGA ATC TTT GCC

239  T   T   F   V   P   L   Y   Q   M   A   T   K   G   V   A   L   M   R   I
901  ACA ACG TTT GTG CTT CTT TAT CAG ATG GCA ACA AAA GGG GCT TTG ATG CGT ATC

259  Y   G   V   P   A   I   L   I   N   C   F   L   V   M   I   Y   L   Q   H
961  TAT GGG GTG CCA GCT ATT TTG ATT AAC TGT TTC CTT GTT ATG ATC TAC TTG CAG CAC

279  T   H   P   A   D   R   P   R   Y   G   S   E   W   D   L   R   G   A   M
1021 ACT CAC CCA GCT GAT AGA CCA CGC TAT GGG TCA GAA TGG GAT CTC CGG GGA GCA ATG

299  V   T   V   D   R   L   F   A   G   V   N   K   V   H   F   H   N   I   A   D   T
1081 GTG ACT GTC GAT AGA CTC TTT GCT GGG GTG AAT AAA GTA TTC CAT CAT AAC ATT GCA GAC ACT

319  H   V   A   H   H   L   F   T   Y   V   P   H   Y   H   A   M   E   A   T   K
1141 CAT GTA GCT CAT CAT CTC TTT ACA GTG CCA CAT TAC CAT GCA ATG GAG GCC ACT AAA

339  A   I   K   P   I   M   G   E   Y   R   Y   D   G   T   P   F   P   Y   K   A
1201 GCA ATC AAG CCT ATA ATG GGT GAG TAT CGG TAC GAT GGT ACC CCA TTT CCA TAC AAG GCA

359  L   W   R   E   A   K   L   F   V   E   P   D   G   A   P   T   Q
1261 TTG TGG AGG GAG GCA AAG CTT TTC GTC GAG CCA GAT GGA GCT CCT ACA CAA

379  G   V   F   W   Y   R   N   K   Y   *
1321 GGC GTT TTC TGG TAC CGG AAC AAG TAT TAA AAA AGT GTC ATG TAG CCT GTT TCT TTA AGA

1381 GAA GTA ATT AGA ACA AGA AAT GTG TAA TGT GTT CTA ATA AAG AAG GCA

1441 AAA AAA AA
```

FIG. 11

```
FAD2.AMI                                                             10                    20                    30                    40                    50
FAH12.AMI  MGAGGRMP----- VPTSSKKSETDTTKRVPCEKPPFSVGDLKKAIPPHCFKRSIPRSFSYL
                                                                     10                    20                    30                    40                    50                    60
           MGGGGRMSTVITSNNSEKKGGSSHLKRAPHTKPPFTLGDLKRAIPPHCFERSFVRSFSYV

FAD2.AMI                    70                    80                    90                   100                   110
           ISDIIIASCFYYVATNYFSLLPQPLSYLAMPLYWACQGCVLTGIWVIAHECGHHAFSDYQ
FAH12.AMI                   70                    80                    90                   100                   110                   120
           AYDVCLSFLFYSIATNFFPYISSPLSYVAWLVYWLFQGCILTGLWVIGHECGHHAFSEYQ

FAD2.AMI                   130                   140                   150                   160                   170
           WLDDTVGLIFHSFLLVPYFSWKYSHRRHHSNTGSLERDEVFVPKQKSAIKWYGKYLNNPL
FAH12.AMI                  130                   140                   150                   160                   170                   180
           LADDIVGLIVHSALLVPYFSWKYSHRRHHSNIGSLERDEVFVPKSKSKISWYSKYSNNPP

FAD2.AMI                   190                   200                   210                   220                   230
           GRIMLTVQFVLGWPLYLAFNVSGRPYDGFACHFFPNAPIYNDRERLQIYLSDAGILAVC
FAH12.AMI                  190                   200                   210                   220                   230                   240
           GRVLTLAATLLLGWPLYLAFNVSGRPYDRFACHYDPYGPIFSERERLQIYIADLGIFATT

FAD2.AMI                   250                   260                   270                   280                   290
           FGLYRYAAAQGMASMICLYGVPLLIVNAFLVLITYLQHTHPSLPHYDSSEWDWLRGALAT
FAH12.AMI                  250                   260                   270                   280                   290                   300
           FVLYQATMAKGLAWVMRIYGVPLLIVNCFLVMITYLQHTHPAIPRYGSSEWDWLRGAMVT

FAD2.AMI                   310                   320                   330                   340                   350
           VDRDYGILNKVFHNITDTHVAHHLFSTMPHYNAMEATKAIKPILGDYYQFDGTPWYVAMY
FAH12.AMI                  310                   320                   330                   340                   350                   360
           VDRDYGVLNKVFHNIADTHVAHHLFATVPHYHAMEATKAIKPIMGEYYRYDGTPFYKALW

FAD2.AMI                   370                   380
           REAKECIYVEPDREGDKKGVYWYNNKL
FAH12.AMI                  370                   380
           REAKECLFVEPDEGAPTQGVFWYRNKY
```

FIG. 12A 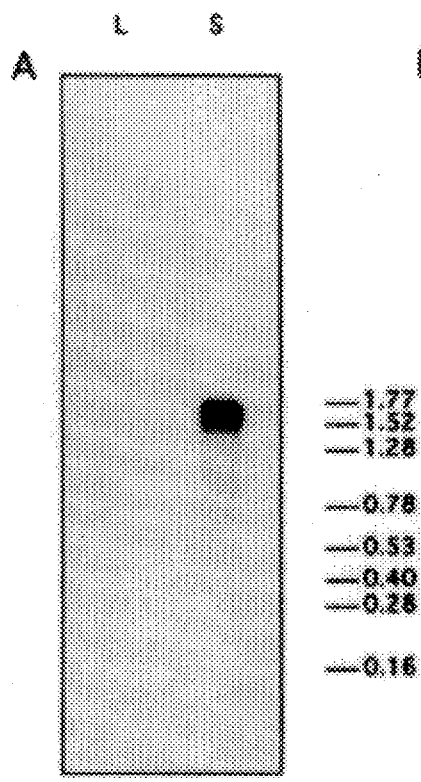 FIG. 12B 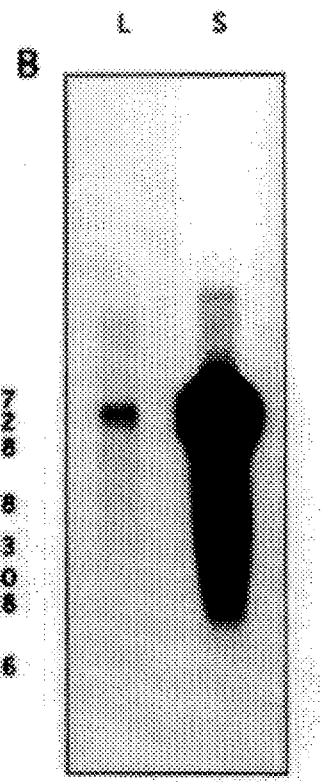
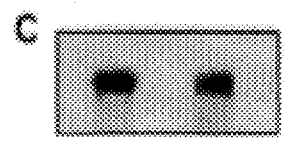
FIG. 12C

FIG. 15A

```
65.4% identity in 1196 bp overlap, initial score: 2188 optimized score: 2210

230       240       250       260       270       280
FAH12.DNA          ACAACAGTGAGAAGAAAGGAGGAAGCAGCCACC-TTAAGCGAGCGCCGCACACGAAGCCT
                                                    X=====   ||||| |||| |||| |||| ||||
FAD2.DNA           CTACTTCTTCCAAGAAA-TCGGAAACCGACCACACCACAAAGCGTGTGCCGTGCGAGAAACCG
                   130       140       150       160       170

290       300       310       320       330       340
FAH12.DNA          CCTTTCACACTGGTGACCTCAAGAGAGCCATCCCACCCCATTGCTTTGAACGCTCTTTT
                   ||||| ||  || ||||| || | |||| || ||| ||  || |||||||||  ||| 
FAD2.DNA           CCTTTCTCGGTGGGAGATCTGAAGAAAGCAATCCCGCCGCATTGTTTCAAACGCTCAATC
                   180       190       200       210       220       230

350       360       370       380       390       400
FAH12.DNA          GTGCGCTCATTCTCCTATGTTGCCTATGATGTCTGCTTAAGTTTTCTTTTCTACTCGATC
                   |||| |||||| ||| |  || ||||||||||   |||||||||  || |||||| ||| 
FAD2.DNA           CCTGGCTCTTCTTCTCCTACCTTATCAGTGACATCATTATAGCCTTCATGCTTCTACTACGTC
                   240       250       260       270       280       290

410       420       430       440       450       460
FAH12.DNA          GCCACCAACTTCTTCCCTTACACATCTCTTCCGCTCTCGTATGTCGCTTGGCTTGGTTTAC
                   ||||||  ||| ||||| |||| || || | |||| | |||||| |||||||||| | |
FAD2.DNA           GCCACCAATTACTTCTCCCTCAGCCTCCTTACTTGGCTTGGCCACTCTAT
                   300       310       320       330       340       350

470       480       490       500       510       520
FAH12.DNA          TGGCTCTTCCAAGGCTGCATTCTCACTGGTCTTTGGGTCATCGGCCATGAATGTGGCCAT
                   |||  || || ||||||| ||| |  ||||| || |||||||||  || |||||||| |
FAD2.DNA           TGGGCCTGTCAAGGCTGTGTCCTAACTGGTATCTGGGTCATAGCCCACGAATGCGGGTCAC
                   360       370       380       390       400       410

530       540       550       560       570       580
FAH12.DNA          CATGCTTTTTAGTGAGTATCAGCTGGCT-GATGACATTGTTGGCCTAATTGTCCATTCTGC
                   || ||||| |||||||||| || |||| ||||| || |||||| ||  || || ||| ||
FAD2.DNA           CACGCATTCAGGCACTACCA-ATGGCTGGATGACACAGTTGGTCTTTATCTTCCATTCCTT
                   420       430       440       450       460       470

590       600       610       620       630       640
FAH12.DNA          ACTTCTGGTTCCATATTTTCATGGAAATATAGCCATCGCCGCCACCATTCTAACATAGG
                   |||||||| ||||| || |  |||| ||||| ||| ||||||| |||| || ||| ||
FAD2.DNA           CCTCCCTCGTCCCTTACTTCTCCTGGAAGTATAGTCATCGCCGTCACCATTCCAACACTGG
                   480       490       500       510       520       530
```

FIG. 15B

```
              650        660        670        680        690        700
FAH12.DNA  ATCTCTCGAGCGAGACGAAGTGTTCGTCCCGAAATCAAAGTCGAAAATTTCATGGTATTC
              ::: ::::::    :::: :::::: :: ::   :: :::::  ::::: ::::
FAD2.DNA   ATCCCTCGAAAAGAGATGAAGTATTTGTCCCAAAGCAGAAATCAGCAATCAAGTGTACGG
              540        550        560        570        580        590

710        720        730        740        750        760
FAH12.DNA  TAAGTACTCAAACAACCCGCCAGTTCGAGTTTGACACTTGCTGCCACGCTCCTCCTTGG
              :: :::::: :: ::  ::::: ::::: :::: ::::::: :::::  :::::  ::
FAD2.DNA   GAAATACCTCAACACAACCCTCTTGACGCATCATGATGTTAACCGTCCAGTTTGTCCTCGG
              600        610        620        630        640        650

770        780        790        800        810        820
FAH12.DNA  CTGGCCTTTATACTTAGCTTTCAATGTCTCTGGTAGACCTTACGATCGCTTTGCTTGCCA
              :::::::: :: :::::::: :::: ::::::  :::::::: : :: :::::::::::
FAD2.DNA   GTGGCCCTTGTACTTAGCCTTTAACGTCTCTGGCAGACCGTATGACGGGTTCGCTTGCCA
              660        670        680        690        700        710

830        840        850        860        870        880
FAH12.DNA  TTATGATCCCTATGGCCCAATATTTTCCGAAAGAGAAAGGCTTCAGATTTACATTGCTGA
              ::    :::::::: :  :::::: :  :: :::::: ::::::::::: :::::::
FAD2.DNA   TTTCTTCCCAACGCTCCATCTACAATGACCGAGAACGCCTCGTTACGGCTACAATGGCAAAAGGGTTGGC
              720        730        740        750        760        770

890        900        910        920        930        940
FAH12.DNA  CCTCGGAATCTTTGCCACAACGTTTGTGCTTTATCAGGCTACAATGGCAAAAGGGTTGGC
              ::: ::  : ::::  ::::: ::: : ::::::::   ::::::   :::::::::::
FAD2.DNA   TGCGGGTATTCTAGCCGTCTGTCTTTGGTCTTGTTCCGTTACCGTTACGCTGCTGCACAAGGATGGC
              780        790        800        810        820        830

950        960        970        980        990       1000
FAH12.DNA  TTGGGTAATGCGTATCTATGGGGTGCCATTGCTTATTGTTAACTGTTCCTTGTTATGAT
              ::::::::::: ::::::::  :::::   ::::: :::::::: ::::::::: :::
FAD2.DNA   CTCGATGATCGCTGCCTGCCGCTCTACGGAGTACCGCTTCTGATAGTGAATGCGTTCCTCGTTGAT
              840        850        860        870        880        890

1010       1020       1030       1040       1050       1060
FAH12.DNA  CACATACTTGCAGCACACTCACCCAGCTATTCCACGCTATGGCTCATCGGAATGGGATTG
              ::: :::::::::::: :: : ::::::::::::::::::::::: : :::::: ::
FAD2.DNA   CACTTACTTGCAGCACACTCATCCCCGTTGCCTCACTAGTCATCAGATTCATCAGAGTGGGACTG
              900        910        920        930        940        950
```

FIG. 15C

```
FAH12.DNA              1070      1080      1090      1100      1110      1120
           GCTCCGGGGAGCAATGGTGACTGTCGATAGAGATTATGGGGTGTTGAATAAAGTATTCCA
           ::::  ::::::::::  ::  ::  ::::::  :::::  :  ::::::::  :::
           GCTCAGGGGAGCTTTGGCTACCGTAGACAGAGACTACGGAATCTTGAACAAGGTGTTCCA
FAD2.DNA        960       970       980       990      1000      1010

FAH12.DNA              1130      1140      1150      1160      1170      1180
           TAACATTGCAGACACTCATGTAGCTCATCTCTTTGCTACAGTGCCACATTACCATGC
           :::::::  :::::  :::::::  :::  :::  ::  :::::  ::::::  ::
           CAACATTACAGACACACACACGTGGCTCATCACCTGTTCTCGACAATGCCGATTATAACGC
FAD2.DNA       1020      1030      1040      1050      1060      1070

FAH12.DNA              1190      1200      1210      1220      1230      1240
           AATGGAGGCCACTAAAGCAATCAAGCCTATAATGGGTGAGTATTACCGGTATGATGGTAC
           ::::::::: ::     ::::  :::::  :::  :::::  ::::::::::
           AATGGAAGCTACAAAGGCGATAAAGCCAATTCTGGGAGACTATTACCAGTTCGATGGAAC
FAD2.DNA   1080      1090      1100      1110      1120      1130

FAH12.DNA              1250      1260      1270      1280      1290      1300
           CCCATTTTACAAGGCATTGTGGAGGAGGCAAAGGAGTGCTTGTTCGTCGAGCCAGATGA
           ::  ::  ::   ::  ::  ::::::::::::  ::::::::
           ACCGTGGTATGTAGCGATGTATAGGGAGGCAAAGGAGTGTATCTATGTAGAACCGGACAG
FAD2.DNA        1140      1150      1160      1170      1180      1190

FAH12.DNA              1310      1320      1330      1340      1350
           AGGAGCTCCTACACAAGGCCGTTTTCTGGTACCGGAACAAG-TAT---TAAAAAGTG---
           ::  :  ::  ::::::  ::::  :    ::::  ::::::   :::v^::
           GGAAGGTGACAAGAAAGGTGTGTACTGGTACAACAATAAGTTATGAGCATGATGGTGAAG
FAD2.DNA        1200      1210      1220      1230      1240      1250

FAH12.DNA              1360      1370      1380      1390      1400      1410
           -TCATGTAG-CCTGTTTCTTAAGAGAAGTAATTAGAACAAGAAGGAATGTGTGTAGT
           :::::::: ::    ::  :: ::::::::  :::::::  :::::::  :
           AAATTGTCGACCTTTCTCTTGTCTCTGTTTTGTTAAAGAAGCTATGCTTCGTTTTA
FAD2.DNA   1260      1270      1280      1290      1300      1310

FAH12.DNA              1420      1430      1440
           GTAATGTGTTCTAATAAAGAAGGCAAAAAAAA
           ::::  :
           ATAATCTTATTGTCCATTTTGTTGTTATGAC
FAD2.DNA   1320      1330      1340      1350
```

TMS-methyl-ricinoleate:

Characteristic Ions:

M/Z

187   Cleavage ion alpha to TMS group

299   "         "

270   Rearrangement ion characteristic of the compound
      $[CH_3O(OTMS)C(CH_2)_7 CH=CH-CH_2]^+$ 369   [M-CH$_3$]   (Molecular ion 384 minus methyl)

353   [M-OCH$_3$]

The ions at m/z 187, 299 and 270 unequivocally establish the Hydroxyl at C12

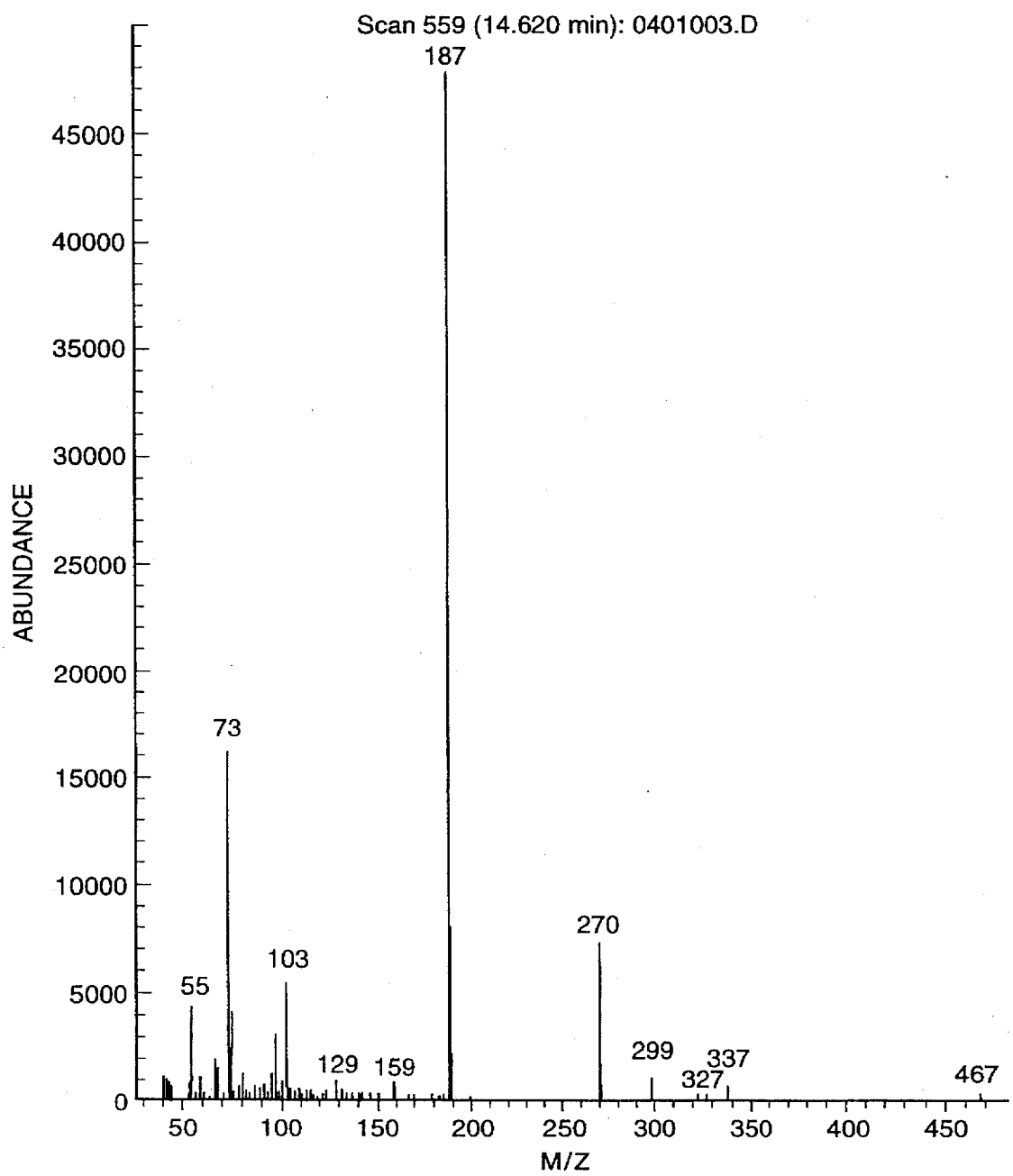

ns. These are synthesized from the fully saturated

SEQUENCE LISTING ( 1 ) GENERAL INFORMATION:

( i i i ) NUMBER OF SEQUENCES: 48

( 2 ) INFORMATION FOR SEQ ID NO:1:

( i ) SEQUENCE CHARACTERISTICS:
        ( A ) LENGTH: 523 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
TGACCTCGGA   ATCTTTGCCA   CAACGTTTGT   GCTTTATCAG   GCTACAATGG   CAAAAGGGTT      60

GGCTTGGGTA   ATGCGTATCT   ATGGGGTGCC   ATTGCTTATT   GTTAACTGTT   TCCTTGTTAT     120

GATCACATAC   TTGCAGCACA   CTCACCCAGC   TATTCCACGC   TATGGCTCAT   CGGAATGGGA     180

TTGGCTCCGG   GGAGCAATGG   TGACTGTCGA   TAGAGATTAT   GGGGTGTTGA   ATAAAGTATT     240

CCATAACATT   GCAGNCACTC   ATGTAGCTCA   TCANCTCTTT   GCTACAGTGN   CACATTACCA     300
```

```
TGCAATGGGG GNCNCTAAGC AATCAAGGCC TATAATGGGN GGATNTTACC GGATNATNGG    360

NCCCCATTTA CAAGGGATTT TTGGGGGGCA AANNNAGTCN TTTTNTNCTG GCCAATTAAG    420

GGGNCTCAAA AAGGGTTTNT TGGCCCGCAA GTTTAAAAGG NATTGNCNG TTTTTAGGGN     480

GGATTTNCCA AAGGATTTTT TTNGGAATTN TNTTTNAGGG GGG                      523
```

( 2 ) INFORMATION FOR SEQ ID NO:2:

( i ) SEQUENCE CHARACTERISTICS:
        ( A ) LENGTH: 540 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

```
CTGACCTCGG AATCTTTGCC ACAACGTTTG TCCTTTATCA GGCTACAATG GCAAAAGGGT    60

TGGCTTGGGT AATGCGTATC TATGGGGTGC CATTGCTTAT TGTTAACTGT TTCCTTGTTA    120

TGATCACATA CTTGCAGCAC ACTCACCCAG CTATTCCACG CTATGGCTCA TCGGAATGGG    180

ATTGGCTCCG GGGAGCAATG GTGACTGTCG ATAGAGATTA TGGGGTGTTG AATAAAGTAT    240

TCCATAACAT TGCAGACACT CATGTAGCTC ATCATCTCTT TGCTACAGTG CCACATTACC    300

ATGCAATGGA GGCCACTAAA GCAATCAAGC CTATAATGGG TGAGTATTAC CGGTATGATG    360

GTNCCCATTT TACAAGGCAT TGTGGAGGGA GCAAAGGAGT CTTNCCGNCG GCCAANTGAG    420

NNGNCNCANA AGNGGTTTTG GCCCGACAAG TTTAAAAGGC ATNNCCTGTT TTNAGGGGGA    480

TTNCAANAGG ATTTTTNNGG AATNGCTTTN GGGGNAAAAN CAGCATTGNG TTAAGGNNGC    540
```

( 2 ) INFORMATION FOR SEQ ID NO:3:

( i ) SEQUENCE CHARACTERISTICS:
        ( A ) LENGTH: 40 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Ile Pro Arg Tyr Gly Ser Ser Glu Trp Asp Trp Leu Arg Gly Ala Met
 1               5                  10                  15

Val Thr Val Asp Arg Asp Tyr Gly Val Leu Asn Lys Val Phe His Asn
            20                  25                  30

Ile Ala Xaa Thr His Val Ala His
            35                  40
```

( 2 ) INFORMATION FOR SEQ ID NO:4:

( i ) SEQUENCE CHARACTERISTICS:
        ( A ) LENGTH: 40 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Leu Pro Trp Tyr Arg Gly Gln Glu Trp Ser Tyr Leu Arg Gly Gly Leu
 1               5                  10                  15

Thr Thr Val Asp Arg Asp Tyr Gly Trp Ile Asn Asn Val His His Asp
            20                  25                  30
```

```
        Ile  Gly  Thr  His  Val  Ile  His  His
                  35                       40
```

( 2 ) INFORMATION FOR SEQ ID NO:5:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
His  Asn  Ile  Ala  Xaa  Thr  His  Val  Ala  His  Xaa  Leu  Phe  Ala  Thr  Val
 1                  5                        10                       15

Xaa  His  Tyr  His  Ala  Met  Gly  Xaa  Xaa  Lys  Gln  Ser  Arg  Pro  Ile  Met
               20                       25                       30

Gly  Gly  Xaa  Tyr  Arg
          35
```

( 2 ) INFORMATION FOR SEQ ID NO:6:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
His  His  Asp  Ile  Gly  Thr  His  Val  Ile  His  His  Leu  Phe  Pro  Gln  Ile
 1                  5                        10                       15

Pro  His  Tyr  His  Leu  Val  Glu  Ala  Thr  Lys  Ser  Ala  Lys  Ser  Val  Leu
               20                       25                       30

Gly  Lys  Tyr  Tyr  Arg
          35
```

( 2 ) INFORMATION FOR SEQ ID NO:7:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Val  Leu  Tyr  Gln  Ala  Thr  Met  Ala  Lys  Gly  Leu  Ala  Trp  Val  Met  Arg
 1                  5                        10                       15

Ile  Tyr  Gly  Val  Pro  Leu  Leu  Ile  Val  Asn  Cys  Phe  Leu  Val  Met  Ile
               20                       25                       30

Thr  Tyr  Leu  Gln  His
          35
```

( 2 ) INFORMATION FOR SEQ ID NO:8:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

Val Leu Leu Tyr Leu Ser Leu Thr Ile Gly Pro Ile Phe Met Leu Lys
1               5                   10                  15

Leu Tyr Gly Val Pro Tyr Leu Ile Phe Val Met Trp Leu Asp Phe Val
            20              25                  30

Thr Tyr Leu His His
            35

( 2 ) INFORMATION FOR SEQ ID NO:9:

( i ) SEQUENCE CHARACTERISTICS:
         ( A ) LENGTH: 40 amino acids
         ( B ) TYPE: amino acid
         ( C ) STRANDEDNESS: single
         ( D ) TOPOLOGY: linear ( i i ) MOLECULE TYPE: peptide ( x i ) SEQUENCE DESCRIPTION: SEQ ID NO:9:

Ile Pro Arg Tyr Gly Ser Ser Glu Trp Asp Trp Leu Arg Gly Ala Met
1               5                   10                  15

Val Thr Val Asp Arg Asp Tyr Gly Val Leu Asn Lys Val Phe His Asn
            20              25                  30

Ile Ala Xaa Thr His Val Ala His
            35              40

( 2 ) INFORMATION FOR SEQ ID NO:10:

( i ) SEQUENCE CHARACTERISTICS:
         ( A ) LENGTH: 40 amino acids
         ( B ) TYPE: amino acid
         ( C ) STRANDEDNESS: single
         ( D ) TOPOLOGY: linear ( i i ) MOLECULE TYPE: peptide ( x i ) SEQUENCE DESCRIPTION: SEQ ID NO:10:

Leu Pro Trp Tyr Arg Gly Lys Glu Trp Ser Tyr Leu Arg Gly Gly Leu
1               5                   10                  15

Thr Thr Ile Asp Arg Asp Tyr Gly Ile Phe Asn Asn Ile His His Asp
            20              25                  30

Ile Gly Thr His Val Ile His His
            35              40

( 2 ) INFORMATION FOR SEQ ID NO:11:

( i ) SEQUENCE CHARACTERISTICS:
         ( A ) LENGTH: 37 amino acids
         ( B ) TYPE: amino acid
         ( C ) STRANDEDNESS: single
         ( D ) TOPOLOGY: linear ( i i ) MOLECULE TYPE: peptide ( x i ) SEQUENCE DESCRIPTION: SEQ ID NO:11:

His Asn Ile Ala Xaa Thr His Val Ala His Xaa Leu Phe Ala Thr Val
1               5                   10                  15

Xaa His Tyr His Ala Met Gly Xaa Xaa Lys Gln Ser Arg Pro Ile Met
            20              25                  30

Gly Gly Xaa Tyr Arg
            35

( 2 ) INFORMATION FOR SEQ ID NO:12:

( i ) SEQUENCE CHARACTERISTICS:
    ( A ) LENGTH: 37 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:12:

His His Asp Ile Gly Thr His Val Ile His His Leu Phe Pro Gln Ile
1               5                   10                  15

Pro His Tyr His Leu Val Asp Ala Thr Arg Ala Ala Lys His Val Leu
            20                  25                  30

Gly Arg Tyr Tyr Arg
            35

( 2 ) INFORMATION FOR SEQ ID NO:13:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

Val Met Arg Ile Tyr Gly Val Pro Leu Leu Ile Val Asn Cys Phe Leu
1               5                   10                  15

Val Met Ile Thr Tyr Leu Gln His
            20

( 2 ) INFORMATION FOR SEQ ID NO:14:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

Val Leu Lys Val Tyr Gly Val Pro Tyr Ile Ile Phe Val Met Trp Leu
1               5                   10                  15

Asp Ala Val Thr Tyr Leu His His
            20

( 2 ) INFORMATION FOR SEQ ID NO:15:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

His Asn Ile Ala Asp Thr His Val Ala His His Leu Phe Ala Thr Val
1               5                   10                  15

Pro His Tyr His Ala Met Glu Ala Thr Lys Ala Ile Lys Pro Ile Met
            20                  25                  30

Gly Glu Tyr Tyr Arg
            35

( 2 ) INFORMATION FOR SEQ ID NO:16:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

```
His His Asp Ile Gly Thr His Val Ile His His Leu Phe Pro Gln Ile
 1               5                  10                  15

Pro His Tyr His Leu Val Asp Ala Thr Arg Ala Ala Lys His Val Leu
                20                  25                  30

Gly Arg Tyr Tyr Arg
            35
```

( 2 ) INFORMATION FOR SEQ ID NO:17:

( i ) SEQUENCE CHARACTERISTICS:
        ( A ) LENGTH: 40 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

```
Ile Pro Arg Tyr Gly Ser Ser Glu Trp Asp Trp Leu Arg Gly Ala Met
 1               5                  10                  15

Val Thr Val Asp Arg Asp Tyr Gly Val Leu Asn Lys Val Phe His Asn
                20                  25                  30

Ile Ala Asp Thr His Val Ala His
            35                  40
```

( 2 ) INFORMATION FOR SEQ ID NO:18:

( i ) SEQUENCE CHARACTERISTICS:
        ( A ) LENGTH: 40 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:18:

```
Leu Pro Trp Tyr Arg Gly Lys Glu Trp Ser Tyr Leu Arg Gly Gly Leu
 1               5                  10                  15

Thr Thr Ile Asp Arg Asp Tyr Gly Ile Phe Asn Asn Ile His His Asp
                20                  25                  30

Ile Gly Thr His Val Ile His His
            35                  40
```

( 2 ) INFORMATION FOR SEQ ID NO:19:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:19:

```
Val Met Arg Ile Tyr Gly Val Pro Leu Leu Ile Val Asn Cys Phe Leu
 1               5                  10                  15
```

```
Val  Met  Ile  Thr  Tyr  Leu  Gln  His
               20
```

( 2 ) INFORMATION FOR SEQ ID NO:20:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:20:

```
Val  Leu  Lys  Val  Tyr  Gly  Val  Pro  Tyr  Ile  Ile  Phe  Val  Met  Trp  Leu
 1              5                        10                       15

Asp  Ala  Val  Thr  Tyr  Leu  His  His
               20
```

( 2 ) INFORMATION FOR SEQ ID NO:21:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:21:

```
His  Asn  Ile  Ala  Asp  Thr  His  Val  Ala  His  His  Leu  Phe  Ala  Thr  Val
 1              5                        10                       15

Pro  His  Tyr  His  Ala  Met  Glu  Ala  Thr  Lys  Ala  Ile  Lys  Pro  Ile  Met
               20                       25                       30

Gly  Glu  Tyr  Tyr  Arg
               35
```

( 2 ) INFORMATION FOR SEQ ID NO:22:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:22:

```
His  His  Asp  Ile  Gly  Thr  His  Val  Ile  His  His  Leu  Phe  Pro  Gln  Ile
 1              5                        10                       15

Pro  His  Tyr  His  Leu  Val  Glu  Ala  Thr  Lys  Ser  Ala  Lys  Ser  Val  Leu
               20                       25                       30

Gly  Lys  Tyr  Tyr  Arg
               35
```

( 2 ) INFORMATION FOR SEQ ID NO:23:

( i ) SEQUENCE CHARACTERISTICS:
        ( A ) LENGTH: 40 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:23:

```
Ile  Pro  Arg  Tyr  Gly  Ser  Ser  Glu  Trp  Asp  Trp  Leu  Arg  Gly  Ala  Met
1              5                        10                       15

Val  Thr  Val  Asp  Arg  Asp  Tyr  Gly  Val  Leu  Asn  Lys  Val  Phe  His  Asn
               20                       25                       30

Ile  Ala  Asp  Thr  His  Val  Ala  His
          35                    40
```

( 2 ) INFORMATION FOR SEQ ID NO:24:

( i ) SEQUENCE CHARACTERISTICS:
        ( A ) LENGTH: 40 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:24:

```
Leu  Pro  Trp  Tyr  Arg  Gly  Gln  Glu  Trp  Ser  Tyr  Leu  Arg  Gly  Gly  Leu
1              5                        10                       15

Thr  Thr  Val  Asp  Arg  Asp  Tyr  Gly  Trp  Ile  Asn  Asn  Val  His  His  Asp
               20                       25                       30

Ile  Gly  Thr  His  Val  Ile  His  His
          35                    40
```

( 2 ) INFORMATION FOR SEQ ID NO:25:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:25:

```
Val  Leu  Tyr  Gln  Ala  Thr  Met  Ala  Lys  Gly  Leu  Ala  Trp  Val  Met  Arg
1              5                        10                       15

Ile  Tyr  Gly  Val  Pro  Leu  Leu  Ile  Val  Asn  Cys  Phe  Leu  Val  Met  Ile
               20                       25                       30

Thr  Tyr  Leu  Gln  His
          35
```

( 2 ) INFORMATION FOR SEQ ID NO:26:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:26:

```
Val  Leu  Leu  Tyr  Leu  Ser  Leu  Thr  Ile  Gly  Pro  Ile  Phe  Met  Leu  Lys
1              5                        10                       15

Leu  Tyr  Gly  Val  Pro  Tyr  Leu  Ile  Phe  Val  Met  Trp  Leu  Asp  Phe  Val
               20                       25                       30

Thr  Tyr  Leu  His  His
          35
```

( 2 ) INFORMATION FOR SEQ ID NO:27:

( i ) SEQUENCE CHARACTERISTICS:
        ( A ) LENGTH: 523 base pairs (B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:27:

| | | | | | |
|---|---|---|---|---|---|
| TGACCTCGGA | ATCTTTGCCA | CAACGTTTGT | GCTTTATCAG | GCTACAATGG | CAAAAGGGTT | 60
| GGCTTGGGTA | ATGCGTATCT | ATGGGGTGCC | ATTGCTTATT | GTTAACTGTT | TCCTTGTTAT | 120
| GATCACATAC | TTGCAGCACA | CTCACCCAGC | TATTCCACGC | TATGGCTCAT | CGGAATGGGA | 180
| TTGGCTCCGG | GGAGCAATGG | TGACTGTCGA | TAGAGATTAT | GGGGTGTTGA | ATAAAGTATT | 240
| CCATAACATT | GCAGNCACTC | ATGTAGCTCA | TCANCTCTTT | GCTACAGTGN | CACATTACCA | 300
| TGCAATGGGG | GNCNCTAAGC | AATCAAGGCC | TATAATGGGN | GGATNTTACC | GGATNATNGG | 360
| NCCCCATTTA | CAAGGGATTT | TGGGGGGCA | AANNNAGTCN | TTTTNTCTG | GCCAATTAAG | 420
| GGGNCTCAAA | AAGGGTTTNT | TGGCCCGCAA | GTTAAAAGG | NATTTGNCNG | TTTTTAGGGN | 480
| GGATTTNCCA | AAGGATTTTT | TTNGGAATTN | TNTTTNAGGG | GGG | | 523

(2) INFORMATION FOR SEQ ID NO:28:

(i) SEQUENCE CHARACTERISTICS:
(A) LENGTH: 517 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:28:

| | | | | | |
|---|---|---|---|---|---|
| TGACCTCGGA | ATCTTTGCCA | CAACGTTTGT | CCTTTATCAG | GCTACAATGG | CAAAAGGGTT | 60
| GGCTTGGGTA | ATGCGTATCT | ATGGGGTGCC | ATTGCTTATT | GTTAACTGTT | TCCTTGTTAT | 120
| GATCACATAC | TTGCAGCACA | CTCACCCAGC | TATTCCACGC | TATGGCTCAT | CGGAATGGGA | 180
| TTGGCTCCGG | GGAGCAATGG | TGACTGTCGA | TAGAGATTAT | GGGGTGTTGA | ATAAAGTATT | 240
| CCATAACATT | GCAGACACTC | ATGTAGCTCA | TCATCTCTTT | GCTACAGTGC | CACATTACCA | 300
| TGCAATGGAG | GCCACTAAAG | CAATCAAGCC | TATAATGGGT | GAGTATTACC | GGTATGATGG | 360
| TNCCCATTTT | ACAAGGCATT | GTGGAGGGAG | CAAAGGAGTC | TTNCCGNCGG | CCAANTGAGN | 420
| NGNCNCANAA | GNGGTTTTGG | CCCGACAAGT | TTAAAAGGCA | TNNCCTGTTT | TNAGGGGGAT | 480
| TNCAANAGGA | TTTTTNNGGA | ATNGCTTTNG | GGGNAAA | | | 517

(2) INFORMATION FOR SEQ ID NO:29:

(i) SEQUENCE CHARACTERISTICS:
(A) LENGTH: 150 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:29:

| | | | | | |
|---|---|---|---|---|---|
| ACTTGGTGAT | GATAGTTCCG | GTTATAGCAA | ATCCGACCAA | AAACGGCCAG | TTACGGTTGA | 60
| ACTCCCGCTT | GAAGAACACG | GGCCATGGAT | CGAACCACCT | TTTCATCTTT | TCTCGAAGCC | 120
| TCAGGAAAGT | GTTAAAAAA | GAGCTTTAGA | | | | 150

(2) INFORMATION FOR SEQ ID NO:30:

(i) SEQUENCE CHARACTERISTICS:

(A) LENGTH: 150 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:30:

```
CACACTTGGT GACCTCAAAT CAAACACCAC ACCTTATAAC TTAGTCTTAA GAGAGAGAGA        60
GAGAGAGAGG AGACATTTCT CTTCTCTGAG ATAAGCACTT CTCTTCCAGA CATCGAAGCC       120
TCAGGAAAGT GCTTAAAAAG AGCTTAAGAA                                         150
```

(2) INFORMATION FOR SEQ ID NO:31:

(i) SEQUENCE CHARACTERISTICS:
(A) LENGTH: 104 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:31:

```
TTAAGAGAGA GAGAGAGAGA GAGGAGACAT TTCTCTTCTC TGAGATAAGC ACTTCTCTTC        60
CAGACATCGA AGCCTCAGGA AAGTGCTTAA AAAGAGCTTA AGAA                         104
```

(2) INFORMATION FOR SEQ ID NO:32:

(i) SEQUENCE CHARACTERISTICS:
(A) LENGTH: 52 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:32:

```
TTCTCTTCCA GACATCGAAG CCTCAGGAAA GTGCTTAAAA AGAGCTTAAG AA                 52
```

(2) INFORMATION FOR SEQ ID NO:33:

(i) SEQUENCE CHARACTERISTICS:
(A) LENGTH: 64 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:33:

```
CTCTAAAGGC ACTTCTCTTC CAGACATCGA AGCCTCAGGA AAGTGCTTAA AAAGAGCTTA        60
AGAA                                                                     64
```

(2) INFORMATION FOR SEQ ID NO:34:

(i) SEQUENCE CHARACTERISTICS:
(A) LENGTH: 90 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:34:

```
GAGAGAGAGG AGACATTTCT CTTCTCTGAG ATAAGCACTT CTCTTCCAGA CATCGAAGCC        60
TCAGGAAAGT GCTTAAAAAG AGCTTAAGAA                                          90
```

( 2 ) INFORMATION FOR SEQ ID NO:35:

( i ) SEQUENCE CHARACTERISTICS:
        ( A ) LENGTH: 83 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:35:

```
AGGAGACACT TCTCTTCTCT GAGATAAGCA CTTCTCTTCC AGACATCGAA GCCTCAGGAA    60

AGTGCTTAAA AAGAGCTTAA GAA                                           83
```

( 2 ) INFORMATION FOR SEQ ID NO:36:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:36:

```
CAGACATCGA AGCCTCAGGA AAGTGCTTAA AAAGAGCTTA AGAA                    44
```

( 2 ) INFORMATION FOR SEQ ID NO:37:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:37:

```
ACTTCTCTTC CAGACATCGA AGCCTCAGGA AAGTGCTTAA AAAGAGCTTA AGAA          54
```

( 2 ) INFORMATION FOR SEQ ID NO:38:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:38:

```
GACATTTCTC TTCTCTGAGA TAAGCACTTC TCTTCCAGAC ATCGAAGCCT CAGGAAAGTG    60

CTTAAAAAGA GCTTAAGAA                                                79
```

( 2 ) INFORMATION FOR SEQ ID NO:39:

( i ) SEQUENCE CHARACTERISTICS:
        ( A ) LENGTH: 1448 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 187..1350

( x i ) SEQUENCE DESCRIPTION: SEQ ID NO:39:

```
GCCACCTTAA GCGAGCGCCG CACACGAAGC CTCCTTTCAC ACTTGGTGAC CTCAAATCAA      60

ACACCACACC TTATAACTTA GTCTTAAGAG AGAGAGAGAG AGAGAGGAGA CATTTCTCTT     120

CTCTGAGATA AGCACTTCTC TTCCAGACAT CGAAGCCTCA GGAAAGTGCT TAAAAGAGC      180

TTAAGA ATG GGA GGT GGT GGT CGC ATG TCT ACT GTC ATA ACC AGC AAC        228
       Met Gly Gly Gly Gly Arg Met Ser Thr Val Ile Thr Ser Asn
         1               5                  10

AAC AGT GAG AAG AAA GGA GGA AGC AGC CAC CTT AAG CGA GCG CCG CAC        276
Asn Ser Glu Lys Lys Gly Gly Ser Ser His Leu Lys Arg Ala Pro His
 15              20                  25                  30

ACG AAG CCT CCT TTC ACA CTT GGT GAC CTC AAG AGA GCC ATC CCA CCC        324
Thr Lys Pro Pro Phe Thr Leu Gly Asp Leu Lys Arg Ala Ile Pro Pro
                 35                  40                  45

CAT TGC TTT GAA CGC TCT TTT GTG CGC TCA TTC TCC TAT GTT GCC TAT        372
His Cys Phe Glu Arg Ser Phe Val Arg Ser Phe Ser Tyr Val Ala Tyr
         50                  55                  60

GAT GTC TGC TTA AGT TTT CTT TTC TAC TCG ATC GCC ACC AAC TTC TTC        420
Asp Val Cys Leu Ser Phe Leu Phe Tyr Ser Ile Ala Thr Asn Phe Phe
             65                  70                  75

CCT TAC ATC TCT TCT CCG CTC TCG TAT GTC GCT TGG CTG GTT TAC TGG        468
Pro Tyr Ile Ser Ser Pro Leu Ser Tyr Val Ala Trp Leu Val Tyr Trp
         80                  85                  90

CTC TTC CAA GGC TGC ATT CTC ACT GGT CTT TGG GTC ATC GGC CAT GAA        516
Leu Phe Gln Gly Cys Ile Leu Thr Gly Leu Trp Val Ile Gly His Glu
 95             100                 105                 110

TGT GGC CAT CAT GCT TTT AGT GAG TAT CAG CTG GCT GAT GAC ATT GTT        564
Cys Gly His His Ala Phe Ser Glu Tyr Gln Leu Ala Asp Asp Ile Val
                115                 120                 125

GGC CTA ATT GTC CAT TCT GCA CTT CTG GTT CCA TAT TTT TCA TGG AAA        612
Gly Leu Ile Val His Ser Ala Leu Leu Val Pro Tyr Phe Ser Trp Lys
            130                 135                 140

TAT AGC CAT CGC CGC CAC CAT TCT AAC ATA GGA TCT CTC GAG CGA GAC        660
Tyr Ser His Arg Arg His His Ser Asn Ile Gly Ser Leu Glu Arg Asp
        145                 150                 155

GAA GTG TTC GTC CCG AAA TCA AAG TCG AAA ATT TCA TGG TAT TCT AAG        708
Glu Val Phe Val Pro Lys Ser Lys Ser Lys Ile Ser Trp Tyr Ser Lys
160                 165                 170

TAC TCA AAC AAC CCG CCA GGT CGA GTT TTG ACA CTT GCT GCC ACG CTC        756
Tyr Ser Asn Asn Pro Pro Gly Arg Val Leu Thr Leu Ala Ala Thr Leu
175                 180                 185                 190

CTC CTT GGC TGG CCT TTA TAC TTA GCT TTC AAT GTC TCT GGT AGA CCT        804
Leu Leu Gly Trp Pro Leu Tyr Leu Ala Phe Asn Val Ser Gly Arg Pro
                195                 200                 205

TAC GAT CGC TTT GCT TGC CAT TAT GAT CCC TAT GGC CCA ATA TTT TCC        852
Tyr Asp Arg Phe Ala Cys His Tyr Asp Pro Tyr Gly Pro Ile Phe Ser
            210                 215                 220

GAA AGA GAA AGG CTT CAG ATT TAC ATT GCT GAC CTC GGA ATC TTT GCC        900
Glu Arg Glu Arg Leu Gln Ile Tyr Ile Ala Asp Leu Gly Ile Phe Ala
        225                 230                 235

ACA ACG TTT GTG CTT TAT CAG GCT ACA ATG GCA AAA GGG TTG GCT TGG        948
Thr Thr Phe Val Leu Tyr Gln Ala Thr Met Ala Lys Gly Leu Ala Trp
        240                 245                 250

GTA ATG CGT ATC TAT GGG GTG CCA TTG CTT ATT GTT AAC TGT TTC CTT        996
Val Met Arg Ile Tyr Gly Val Pro Leu Leu Ile Val Asn Cys Phe Leu
255                 260                 265                 270

GTT ATG ATC ACA TAC TTG CAG CAC ACT CAC CCA GCT ATT CCA CGC TAT       1044
Val Met Ile Thr Tyr Leu Gln His Thr His Pro Ala Ile Pro Arg Tyr
                275                 280                 285
```

| | | | | | | | | | | | | | | | | |
|---|---|---|---|---|---|---|---|---|---|---|---|---|---|---|---|---|
| GGC | TCA | TCG | GAA | TGG | GAT | TGG | CTC | CGG | GGA | GCA | ATG | GTG | ACT | GTC | GAT | 1092 |
| Gly | Ser | Ser | Glu | Trp | Asp | Trp | Leu | Arg | Gly | Ala | Met | Val | Thr | Val | Asp | |
| | | | 290 | | | | | 295 | | | | 300 | | | | |
| AGA | GAT | TAT | GGG | GTG | TTG | AAT | AAA | GTA | TTC | CAT | AAC | ATT | GCA | GAC | ACT | 1140 |
| Arg | Asp | Tyr | Gly | Val | Leu | Asn | Lys | Val | Phe | His | Asn | Ile | Ala | Asp | Thr | |
| | | 305 | | | | | 310 | | | | | 315 | | | | |
| CAT | GTA | GCT | CAT | CAT | CTC | TTT | GCT | ACA | GTG | CCA | CAT | TAC | CAT | GCA | ATG | 1188 |
| His | Val | Ala | His | His | Leu | Phe | Ala | Thr | Val | Pro | His | Tyr | His | Ala | Met | |
| | 320 | | | | | 325 | | | | | 330 | | | | | |
| GAG | GCC | ACT | AAA | GCA | ATC | AAG | CCT | ATA | ATG | GGT | GAG | TAT | TAC | CGG | TAT | 1236 |
| Glu | Ala | Thr | Lys | Ala | Ile | Lys | Pro | Ile | Met | Gly | Glu | Tyr | Tyr | Arg | Tyr | |
| 335 | | | | | 340 | | | | | 345 | | | | | 350 | |
| GAT | GGT | ACC | CCA | TTT | TAC | AAG | GCA | TTG | TGG | AGG | GAG | GCA | AAG | GAG | TGC | 1284 |
| Asp | Gly | Thr | Pro | Phe | Tyr | Lys | Ala | Leu | Trp | Arg | Glu | Ala | Lys | Glu | Cys | |
| | | | | 355 | | | | | 360 | | | | | 365 | | |
| TTG | TTC | GTC | GAG | CCA | GAT | GAA | GGA | GCT | CCT | ACA | CAA | GGC | GTT | TTC | TGG | 1332 |
| Leu | Phe | Val | Glu | Pro | Asp | Glu | Gly | Ala | Pro | Thr | Gln | Gly | Val | Phe | Trp | |
| | | | 370 | | | | | 375 | | | | | 380 | | | |
| TAC | CGG | AAC | AAG | TAT | TAAAAAGTG | | TCATGTAGCC | | TGTTTCTTTA | | AGAGAAGTAA | | | | | 1387 |
| Tyr | Arg | Asn | Lys | Tyr | | | | | | | | | | | | |
| | | 385 | | | | | | | | | | | | | | |

TTAGAACAAG AAGGAATGTG TGTGTAGTGT AATGTGTTCT AATAAAGAAG GCAAAAAAAA  1447

A  1448

( 2 ) INFORMATION FOR SEQ ID NO:40:

( i ) SEQUENCE CHARACTERISTICS:
        ( A ) LENGTH: 387 amino acids
        ( B ) TYPE: amino acid
        ( D ) TOPOLOGY: linear ( i i ) MOLECULE TYPE: protein ( x i ) SEQUENCE DESCRIPTION: SEQ ID NO:40:

| | | | | | | | | | | | | | | |
|---|---|---|---|---|---|---|---|---|---|---|---|---|---|---|
| Met | Gly | Gly | Gly | Gly | Arg | Met | Ser | Thr | Val | Ile | Thr | Ser | Asn | Asn | Ser |
| 1 | | | | 5 | | | | | 10 | | | | | 15 | |
| Glu | Lys | Lys | Gly | Gly | Ser | Ser | His | Leu | Lys | Arg | Ala | Pro | His | Thr | Lys |
| | | | 20 | | | | | 25 | | | | 30 | | | |
| Pro | Pro | Phe | Thr | Leu | Gly | Asp | Leu | Lys | Arg | Ala | Ile | Pro | Pro | His | Cys |
| | | | 35 | | | | 40 | | | | | 45 | | | |
| Phe | Glu | Arg | Ser | Phe | Val | Arg | Ser | Phe | Ser | Tyr | Val | Ala | Tyr | Asp | Val |
| | 50 | | | | | 55 | | | | | 60 | | | | |
| Cys | Leu | Ser | Phe | Leu | Phe | Tyr | Ser | Ile | Ala | Thr | Asn | Phe | Phe | Pro | Tyr |
| 65 | | | | | 70 | | | | | 75 | | | | | 80 |
| Ile | Ser | Ser | Pro | Leu | Ser | Tyr | Val | Ala | Trp | Leu | Val | Tyr | Trp | Leu | Phe |
| | | | | 85 | | | | | 90 | | | | | 95 | |
| Gln | Gly | Cys | Ile | Leu | Thr | Gly | Leu | Trp | Val | Ile | Gly | His | Glu | Cys | Gly |
| | | | 100 | | | | | 105 | | | | | 110 | | |
| His | His | Ala | Phe | Ser | Glu | Tyr | Gln | Leu | Ala | Asp | Asp | Ile | Val | Gly | Leu |
| | | | 115 | | | | | 120 | | | | | 125 | | |
| Ile | Val | His | Ser | Ala | Leu | Leu | Val | Pro | Tyr | Phe | Ser | Trp | Lys | Tyr | Ser |
| | | 130 | | | | | 135 | | | | | 140 | | | |
| His | Arg | Arg | His | His | Ser | Asn | Ile | Gly | Ser | Leu | Glu | Arg | Asp | Glu | Val |
| 145 | | | | | 150 | | | | | 155 | | | | | 160 |
| Phe | Val | Pro | Lys | Ser | Lys | Ser | Lys | Ile | Ser | Trp | Tyr | Ser | Lys | Tyr | Ser |
| | | | 165 | | | | | 170 | | | | | 175 | | |
| Asn | Asn | Pro | Pro | Gly | Arg | Val | Leu | Thr | Leu | Ala | Ala | Thr | Leu | Leu | Leu |
| | | | 180 | | | | | 185 | | | | | 190 | | |

| | | | | | | | | | | | | | | |
|---|---|---|---|---|---|---|---|---|---|---|---|---|---|---|
| Gly | Trp | Pro 195 | Leu | Tyr | Leu | Ala | Phe 200 | Asn | Val | Ser | Gly 205 | Arg | Pro | Tyr | Asp |
| Arg | Phe 210 | Ala | Cys | His | Tyr 215 | Asp | Pro | Tyr | Gly | Pro 220 | Ile | Phe | Ser | Glu | Arg |
| Glu 225 | Arg | Leu | Gln | Ile | Tyr 230 | Ile | Ala | Asp | Leu | Gly 235 | Ile | Phe | Ala | Thr | Thr 240 |
| Phe | Val | Leu | Tyr | Gln 245 | Ala | Thr | Met | Ala | Lys 250 | Gly | Leu | Ala | Trp | Val 255 | Met |
| Arg | Ile | Tyr | Gly 260 | Val | Pro | Leu | Leu | Ile 265 | Val | Asn | Cys | Phe | Leu 270 | Val | Met |
| Ile | Thr | Tyr 275 | Leu | Gln | His | Thr | His 280 | Pro | Ala | Ile | Pro | Arg 285 | Tyr | Gly | Ser |
| Ser | Glu 290 | Trp | Asp | Trp | Leu | Arg 295 | Gly | Ala | Met | Val | Thr 300 | Val | Asp | Arg | Asp |
| Tyr 305 | Gly | Val | Leu | Asn | Lys 310 | Val | Phe | His | Asn | Ile 315 | Ala | Asp | Thr | His | Val 320 |
| Ala | His | His | Leu | Phe 325 | Ala | Thr | Val | Pro | His 330 | Tyr | His | Ala | Met | Glu 335 | Ala |
| Thr | Lys | Ala | Ile 340 | Lys | Pro | Ile | Met | Gly 345 | Glu | Tyr | Tyr | Arg | Tyr 350 | Asp | Gly |
| Thr | Pro | Phe 355 | Tyr | Lys | Ala | Leu | Trp 360 | Arg | Glu | Ala | Lys | Glu 365 | Cys | Leu | Phe |
| Val | Glu 370 | Pro | Asp | Glu | Gly | Ala 375 | Pro | Thr | Gln | Gly | Val 380 | Phe | Trp | Tyr | Arg |
| Asn 385 | Lys | Tyr | | | | | | | | | | | | | |

(2) INFORMATION FOR SEQ ID NO:41:

(i) SEQUENCE CHARACTERISTICS:
    (A) LENGTH: 383 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:41:

| | | | | | | | | | | | | | | |
|---|---|---|---|---|---|---|---|---|---|---|---|---|---|---|
| Met 1 | Gly | Ala | Gly | Gly 5 | Arg | Met | Pro | Val | Pro 10 | Thr | Ser | Ser | Lys | Lys 15 | Ser |
| Glu | Thr | Asp | Thr 20 | Thr | Lys | Arg | Val | Pro 25 | Cys | Glu | Lys | Pro | Pro 30 | Phe | Ser |
| Val | Gly | Asp 35 | Leu | Lys | Lys | Ala | Ile 40 | Pro | Pro | His | Cys | Phe 45 | Lys | Arg | Ser |
| Ile | Pro 50 | Arg | Ser | Phe | Ser | Tyr 55 | Leu | Ile | Ser | Asp | Ile 60 | Ile | Ile | Ala | Ser |
| Cys 65 | Phe | Tyr | Tyr | Val | Ala 70 | Thr | Asn | Tyr | Phe | Ser 75 | Leu | Leu | Pro | Gln | Pro 80 |
| Leu | Ser | Tyr | Leu | Ala 85 | Trp | Pro | Leu | Tyr | Trp 90 | Ala | Cys | Gln | Gly | Cys 95 | Val |
| Leu | Thr | Gly | Ile 100 | Trp | Val | Ile | Ala | His 105 | Glu | Cys | Gly | His | His 110 | Ala | Phe |
| Ser | Asp | Tyr 115 | Gln | Trp | Leu | Asp | Asp 120 | Thr | Val | Gly | Leu | Ile 125 | Phe | His | Ser |
| Phe | Leu 130 | Leu | Val | Pro | Tyr | Phe 135 | Ser | Trp | Lys | Tyr | Ser 140 | His | Arg | Arg | His |
| His | Ser | Asn | Thr | Gly | Ser | Leu | Glu | Arg | Asp | Glu | Val | Phe | Val | Pro | Lys |

-continued

|  | 145 |  |  |  | 150 |  |  |  | 155 |  |  |  | 160 |
|---|---|---|---|---|---|---|---|---|---|---|---|---|---|
| Gln | Lys | Ser | Ala | Ile<br>165 | Lys | Trp | Tyr | Gly | Lys<br>170 | Tyr | Leu | Asn | Asn<br>175 | Pro | Leu |

Gly Arg Ile Met Met Leu Thr Val Gln Phe Val Leu Gly Trp Pro Leu
         180                   185                   190

Tyr Leu Ala Phe Asn Val Ser Gly Arg Pro Tyr Asp Gly Phe Ala Cys
         195                   200                   205

His Phe Phe Pro Asn Ala Pro Ile Tyr Asn Asp Arg Glu Arg Leu Gln
    210                   215                   220

Ile Tyr Leu Ser Asp Ala Gly Ile Leu Ala Val Cys Phe Gly Leu Tyr
225                   230                   235                   240

Arg Tyr Ala Ala Ala Gln Gly Met Ala Ser Met Ile Cys Leu Tyr Gly
            245                   250                   255

Val Pro Leu Leu Ile Val Asn Ala Phe Leu Val Leu Ile Thr Tyr Leu
            260                   265                   270

Gln His Thr His Pro Ser Leu Pro His Tyr Asp Ser Ser Glu Trp Asp
        275                   280                   285

Trp Leu Arg Gly Ala Leu Ala Thr Val Asp Arg Asp Tyr Gly Ile Leu
    290                   295                   300

Asn Lys Val Phe His Asn Ile Thr Asp Thr His Val Ala His His Leu
305                   310                   315                   320

Phe Ser Thr Met Pro His Tyr Asn Ala Met Glu Ala Thr Lys Ala Ile
                325                   330                   335

Lys Pro Ile Leu Gly Asp Tyr Tyr Gln Phe Asp Gly Thr Pro Trp Tyr
            340                   345                   350

Val Ala Met Tyr Arg Glu Ala Lys Glu Cys Ile Tyr Val Glu Pro Asp
            355                   360                   365

Arg Glu Gly Asp Lys Lys Gly Val Tyr Trp Tyr Asn Asn Lys Leu
370                   375                   380

(2) INFORMATION FOR SEQ ID NO:42:

(i) SEQUENCE CHARACTERISTICS:
        (A) LENGTH: 387 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:42:

Met Gly Gly Gly Gly Arg Met Ser Thr Val Ile Thr Ser Asn Asn Ser
1               5                   10                  15

Glu Lys Lys Gly Gly Ser Ser His Leu Lys Arg Ala Pro His Thr Lys
            20                  25                  30

Pro Pro Phe Thr Leu Gly Asp Leu Lys Arg Ala Ile Pro Pro His Cys
        35                  40                  45

Phe Glu Arg Ser Phe Val Arg Ser Phe Ser Tyr Val Ala Tyr Asp Val
    50                  55                  60

Cys Leu Ser Phe Leu Phe Tyr Ser Ile Ala Thr Asn Phe Phe Pro Tyr
65                  70                  75                  80

Ile Ser Ser Pro Leu Ser Tyr Val Ala Trp Leu Val Tyr Trp Leu Phe
                85                  90                  95

Gln Gly Cys Ile Leu Thr Gly Leu Trp Val Ile Gly His Glu Cys Gly
            100                 105                 110

His His Ala Phe Ser Glu Tyr Gln Leu Ala Asp Asp Ile Val Gly Leu
        115                 120                 125

Ile Val His Ser Ala Leu Leu Val Pro Tyr Phe Ser Trp Lys Tyr Ser
130                     135                     140

His Arg Arg His His Ser Asn Ile Gly Ser Leu Glu Arg Asp Glu Val
145                     150                     155                     160

Phe Val Pro Lys Ser Lys Ser Lys Ile Ser Trp Tyr Ser Lys Tyr Ser
                165                     170                     175

Asn Asn Pro Pro Gly Arg Val Leu Thr Leu Ala Ala Thr Leu Leu Leu
            180                     185                     190

Gly Trp Pro Leu Tyr Leu Ala Phe Asn Val Ser Gly Arg Pro Tyr Asp
        195                     200                     205

Arg Phe Ala Cys His Tyr Asp Pro Tyr Gly Pro Ile Phe Ser Glu Arg
210                     215                     220

Glu Arg Leu Gln Ile Tyr Ile Ala Asp Leu Gly Ile Phe Ala Thr Thr
225                     230                     235                     240

Phe Val Leu Tyr Gln Ala Thr Met Ala Lys Gly Leu Ala Trp Val Met
                245                     250                     255

Arg Ile Tyr Gly Val Pro Leu Leu Ile Val Asn Cys Phe Leu Val Met
            260                     265                     270

Ile Thr Tyr Leu Gln His Thr His Pro Ala Ile Pro Arg Tyr Gly Ser
        275                     280                     285

Ser Glu Trp Asp Trp Leu Arg Gly Ala Met Val Thr Val Asp Arg Asp
290                     295                     300

Tyr Gly Val Leu Asn Lys Val Phe His Asn Ile Ala Asp Thr His Val
305                     310                     315                     320

Ala His His Leu Phe Ala Thr Val Pro His Tyr His Ala Met Glu Ala
                325                     330                     335

Thr Lys Ala Ile Lys Pro Ile Met Gly Glu Tyr Tyr Arg Tyr Asp Gly
            340                     345                     350

Thr Pro Phe Tyr Lys Ala Leu Trp Arg Glu Ala Lys Glu Cys Leu Phe
        355                     360                     365

Val Glu Pro Asp Glu Gly Ala Pro Thr Gln Gly Val Phe Trp Tyr Arg
370                     375                     380

Asn Lys Tyr
385

( 2 ) INFORMATION FOR SEQ ID NO:43:

( i ) SEQUENCE CHARACTERISTICS:
        ( A ) LENGTH: 1222 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:43:

```
ACAACAGTGA GAAGAAAGGA GGAAGCAGCC ACCTTAAGCG AGCGCCGCAC ACGAAGCCTC      60

CTTTCACACT TGGTGACCTC AAGAGAGCCA TCCCACCCCA TTGCTTTGAA CGCTCTTTTG     120

TGCGCTCATT CTCCTATGTT GCCTATGATG TCTGCTTAAG TTTTCTTTTC TACTCGATCG     180

CCACCAACTT CTTCCCTTAC ATCTCTTCTC CGCTCTCGTA TGTCGCTTGG CTGGTTTACT     240

GGCTCTTCCA AGGCTGCATT CTCACTGGTC TTTGGGTCAT CGGCCATGAA TGTGGCCATC     300

ATGCTTTTAG TGAGTATCAG CTGGCTGATG ACATTGTTGG CCTAATTGTC CATTCTGCAC     360

TTCTGGTTCC ATATTTTTCA TGGAAATATA GCCATCGCCG CCACCATTCT AACATAGGAT     420

CTCTCGAGCG AGACGAAGTG TTCGTCCCGA AATCAAAGTC GAAAATTTCA TGGTATTCTA     480
```

```
AGTACTCAAA CAACCCGCCA GGTCGAGTTT TGACACTTGC TGCCACGCTC CTCCTTGGCT        540
GGCCTTTATA CTTAGCTTTC AATGTCTCTG GTAGACCTTA CGATCGCTTT GCTTGCCATT        600
ATGATCCCTA TGGCCCAATA TTTTCCGAAA GAGAAAGGCT TCAGATTTAC ATTGCTGACC        660
TCGGAATCTT TGCCACAACG TTTGTGCTTT ATCAGGCTAC AATGGCAAAA GGGTTGGCTT        720
GGGTAATGCG TATCTATGGG GTGCCATTGC TTATTGTTAA CTGTTTCCTT GTTATGATCA        780
CATACTTGCA GCACACTCAC CCAGCTATTC CACGCTATGG CTCATCGGAA TGGGATTGGC        840
TCCGGGGAGC AATGGTGACT GTCGATAGAG ATTATGGGGT GTTGAATAAA GTATTCCATA        900
ACATTGCAGA CACTCATGTA GCTCATCATC TCTTTGCTAC AGTGCCACAT TACCATGCAA        960
TGGAGGCCAC TAAAGCAATC AAGCCTATAA TGGGTGAGTA TTACCGGTAT GATGGTACCC       1020
CATTTTACAA GGCATTGTGG AGGGAGGCAA AGGAGTGCTT GTTCGTCGAG CCAGATGAAG       1080
GAGCTCCTAC ACAAGGCGTT TTCTGGTACC GGAACAAGTA TTAAAAAAGT GTCATGTAGC       1140
CTGTTTCTTT AAGAGAAGTA ATTAGAACAA GAAGGAATGT GTGTGTAGTG TAATGTGTTC       1200
TAATAAAGAA GGCAAAAAAA AA                                                1222
```

( 2 ) INFORMATION FOR SEQ ID NO:44:

( i ) SEQUENCE CHARACTERISTICS:
        ( A ) LENGTH: 1231 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:44:

```
CTACTTCTTC CAAGAAATCG GAAACCGACA CCACAAAGCG TGTGCCGTGC GAGAAACCGC         60
CTTTCTCGGT GGGAGATCTG AAGAAAGCAA TCCCGCCGCA TTGTTTCAAA CGCTCAATCC        120
CTCGCTCTTT CTCCTACCTT ATCAGTGACA TCATTATAGC CTCATGCTTC TACTACGTCG        180
CCACCAATTA CTTCTCTCTC CTCCCTCAGC CTCTCTCTTA CTTGGCTTGG CCACTCTATT        240
GGGCCTGTCA AGGCTGTGTC CTAACTGGTA TCTGGGTCAT AGCCCACGAA TGCGGTCACC        300
ACGCATTCAG CGACTACCAA TGGCTGGATG ACACAGTTGG TCTTATCTTC CATTCCTTCC        360
TCCTCGTCCC TTACTTCTCC TGGAAGTATA GTCATCGCCG TCACCATTCC AACACTGGAT        420
CCCTCGAAAG AGATGAAGTA TTTGTCCCAA AGCAGAAATC AGCAATCAAG TGGTACGGGA        480
AATACCTCAA CAACCCTCTT GGACGCATCA TGATGTTAAC CGTCCAGTTT GTCCTCGGGT        540
GGCCCTTGTA CTTAGCCTTT AACGTCTCTG GCAGACCGTA TGACGGGTTC GCTTGCCATT        600
TCTTCCCCAA CGCTCCCATC TACAATGACC GAGAACGCCT CCAGATATAC CTCTCTGATG        660
CGGGTATTCT AGCCGTCTGT TTTGGTCTTT ACCGTTACGC TGCTGCACAA GGGATGGCCT        720
CGATGATCTG CCTCTACGGA GTACCGCTTC TGATAGTGAA TGCGTTCCTC GTCTTGATCA        780
CTTACTTGCA GCACACTCAT CCCTCGTTGC CTCACTACGA TTCATCAGAG TGGGACTGGC        840
TCAGGGGAGC TTTGGCTACC GTAGACAGAG ACTACGGAAT CTTGAACAAG GTGTTCCACA        900
ACATTACAGA CACACACGTG GCTCATCACC TGTTCTCGAC AATGCCGCAT TATAACGCAA        960
TGGAAGCTAC AAAGGCGATA AAGCCAATTC TGGGAGACTA TTACCAGTTC GATGGAACAC       1020
CGTGGTATGT AGCGATGTAT AGGGAGGCAA AGGAGTGTAT CTATGTAGAA CCGGACAGGG       1080
AAGGTGACAA GAAAGGTGTG TACTGGTACA ACAATAAGTT ATGAGCATGA TGGTGAAGAA       1140
ATTGTCGACC TTTCTCTTGT CTGTTTGTCT TTTGTTAAAG AAGCTATGCT TCGTTTTAAT       1200
```

AATCTTATTG TCCATTTTGT TGTGTTATGA C                      1231

(2) INFORMATION FOR SEQ ID NO:45:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:45:

GCTCTTTTGT GCGCTCATTC                                    20

(2) INFORMATION FOR SEQ ID NO:46:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:46:

TCGACAGTCA CCATTGCTCC                                    20

(2) INFORMATION FOR SEQ ID NO:47:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:47:

TGGAARTA YW SNCA YMGNMG NCAMCA                           26

(2) INFORMATION FOR SEQ ID NO:48:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:48:

AANARRTGRT GNGCNACRTG NGTRTC                             26

USE OF PLANT FATTY ACYL HYDROXYLASES TO PRODUCE HYDROXYLATED FATTY ACIDS AND DERIVATIVES IN PLANTS This Invention was made with Government support under Contract No. DE-FG02-94ER20133 awarded by the Department of Energy. The Government has certain rights in this invention.

TECHNICAL FIELD

The present invention concerns the identification of nucleic acid sequences and constructs, and methods related thereto, and the use of these sequences and constructs to produce genetically modified plants for the purpose of altering the composition of plant oils, waxes and related compounds.

BACKGROUND

Extensive surveys of the fatty acid composition of seed oils from different species of higher plants have resulted in the identification of more than 210 naturally occurring fatty acids which differ by the number and arrangement of double or triple bonds and various functional groups, such as hydroxyls, ketones, epoxys, cyclopentenyl or cyclopropyl groups, furans or halogens (van de Loo et al. 1993). At least 33 structurally distinct monohydroxylated plant fatty acids, and 12 different polyhydroxylated fatty acids have been described (reviewed by van de Loo et al. 1993; Smith, 1985).

The most commonly occurring fatty acids in both membrane and storage lipids are 16- and 18-carbon fatty acids which may have from zero to three, methylene-interrupted, unsaturations. These are synthesized from the fully saturated species as the result of a series of sequential desaturations which usually begin at the Δ9 carbon and progress in the direction of the methyl carbon (Browse and Somerville, 1991). Fatty acids which cannot be described by this simple algorithm are generally considered "unusual" even though several, such as lauric (12:0), erucic (22:1) and ricinoleic acid (12D-hydroxyoctadec-cis-9-enoic acid) are of significant commercial importance. The biosynthesis of hydroxylated fatty acids such as ricinoleic acid in castor (*Ricinus communis*) seed is the subject of this invention.

The taxonomic relationships between plants having similar or identical kinds of unusual fatty acids have been examined (van de Loo et al., 1993). In some cases, particular fatty acids occur mostly or solely in related taxa. In other cases there does not appear to be a direct link between taxonomic relationships and the occurrence of unusual fatty acids. In this respect, ricinoleic acid has now been identified in 12 genera from 10 families (reviewed in van de Loo et al., 1993). Thus, it appears that the ability to synthesize hydroxylated fatty acids has evolved several times independently during the radiation of the angiosperms. This suggested to us that the enzymes which introduce hydroxyl groups into fatty acids arose by minor modifications of a related enzyme. Indeed, as noted below, this invention is based on our discovery that plant fatty acid hydroxylases are highly homologous to plant fatty acid desaturases.

A feature of hydroxylated or other unusual fatty acids is that they are generally confined to seed triacylglycerols, being largely excluded from the polar lipids by unknown mechanisms (Battey and Ohlrogge 1989; Prasad et al., 1987). This is particularly intriguing since diacylglycerol is a precursor of both triacylglycerol and polar lipid. With castor microsomes, there is some evidence that the pool of ricinoleoyl-containing polar lipid is minimized by a preference of diacylglycerol acyltransferase for ricinoleate-containing diacylglycerols (Bafor et al. 1991). Analyses of vegetative tissues have generated few reports of unusual fatty acids, other than those occurring in the cuticle. A small number of exceptions exist in which unusual fatty acids are found in tissues other than the seed.

Castor (*Ricinus communis* L.) is a minor oilseed crop. Approximately 50% of the seed weight is oil (triacylglycerol) in which 85–90% of total fatty acids are the hydroxylated fatty acid, ricinoleic acid (12D-hydroxyoctadec-cis-9-enoic acid). Oil pressed or extracted from castor seeds has many industrial uses based upon the properties endowed by the hydroxylated fatty acid. The most important uses are production of paints and varnishes, nylon-type synthetic polymers, resins, lubricants, and cosmetics (Atsmon 1989). In addition to oil, the castor seed contains the extremely toxic protein ricin, allergenic proteins, and the alkaloid ricinine. These constituents preclude the use of the untreated seed meal (following oil extraction) as a livestock feed, normally an important economic aspect of oilseed utilization. Furthermore, with the variable nature of castor plants and a lack of investment in breeding, castor has few favorable agronomic characteristics. For a combination of these reasons, castor is no longer grown in the United States and the development of an alternative domestic source of hydroxylated fatty acids would be attractive. The production of ricinoleic acid, the important constituent of castor oil, in an established oilseed crop through genetic engineering would be a particularly effective means of creating a domestic source.

The biosynthesis of ricinoleic (12D-hydroxyoctadec-cis-9-enoic) acid from oleic acid in the developing endosperm of castor (*Ricinus communis*) has been studied by a variety of methods. Morris (1967) established in double-labeling studies that hydroxylation occurs directly by hydroxyl substitution rather than via an unsaturated-, keto- or epoxy-intermediate. Hydroxylation using oleoyl-CoA as precursor can be demonstrated in crude preparations or microsomes, but activity in microsomes is unstable and variable, and isolation of the microsomes involved a considerable, or sometimes complete loss of activity (Galliard and Stumpf, 1966; Moreau and Stumpf, 1981. Oleic acid can replace oleoyl-CoA as a precursor, but only in the presence of CoA, $Mg^{2+}$ and ATP (Galliard and Stumpf, 1966) indicating that activation to the acyl-CoA is necessary. However, no radioactivity could be detected in ricinoleoyl-CoA (Moreau and Stumpf, 1981). These and more recent observations (Bafor et al., 1991) have been interpreted as evidence that the substrate for the castor oleate hydroxylase is oleic acid esterified to phosphatidylcholine or another phospholipid.

The hydroxylase is sensitive to cyanide and azide, and dialysis against metal chelators reduces activity, which could be restored by addition of $FeSO_4$, suggesting iron involvement in enzyme activity (Galliard and Stumpf, 1966). Ricinoleic acid synthesis requires molecular oxygen (Galliard and Stumpf, 1966; Moreau and Stumpf 1981) and requires NAD(P)H to reduce cytochrome b5 which is thought to be the intermediate electron donor for the hydroxylase reaction (Smith et al., 1992). Carbon monoxide does not inhibit hydroxylation, indicating that a cytochrome P450 is not involved (Galliard and Stumpf, 1966; Moreau and Stumpf 1981). Data from a study of the substrate specificity of the hydroxylase show that all substrate parameters (i.e. chain length and double bond position with respect to both ends) are important; deviations in these parameters caused reduced activity relative to oleic acid (Howling et al., 1972). The position at which the hydroxyl was introduced, however, was determined by the position of the double bond, always being three carbons distal. Thus, the castor acyl hydroxylase enzyme can produce a family of different hydroxylated fatty acids depending on the availability of substrates. Thus, although we refer to the enzyme throughout as oleate hydroxylase it can more properly be considered an acyl hydroxylase of broad substrate specificity.

The only other organism in which ricinoleic acid biosynthesis has been investigated is the ergot fungus, *Claviceps purpurea*. Ricinoleate accumulates (up to 40% of the fatty acids) in the glycerides produced particularly by sclerotia of anaerobic cultures (Kren et al., 1985). As this suggests, oxygen is not necessary for the synthesis of ricinoleic acid in Claviceps, and the precursor of ricinoleic acid in fact appears to be linoleic acid (Morris et al., 1966). However, ricinoleic acid may not be formed simply by hydration of linoleic acid, since there are no free hydroxyl groups in ergot oil. Rather, the hydroxyl groups are all esterified to other, non-hydroxy fatty acids, leading to a range of tetra-acyl-, penta-acyl- and hexa-acyl-glycerides. These estolides may be formed by a direct enzymic addition of non-hydroxy fatty acids across the Δ12 double bond of linoleate (Morris, 1970). Ricinoleic acid may, therefore, be merely an artifact of the hydrolysis employed to study the fatty acid composition of the oil.

The castor oleate hydroxylase has many superficial similarities to the microsomal fatty acyl desaturases (Browse and Somerville, 1991). In particular, plants have a microsomal oleate desaturase active at the Δ12 position. The substrate of this enzyme (Schmidt et al., 1993) and of the hydroxylase (Bafor et al., 1991) appears to be oleate esterified to the sn-2 position of phosphatidylcholine. The modification occurs at the same position (Δ12) in the carbon chain, and requires the same cofactors, namely electrons from NADH via cytochrome $b_5$ (Kearns et al., 1991; Smith et al., 1992) and molecular oxygen. Neither enzyme is inhibited by carbon monoxide (Moreau and Stumpf, 1981) the characteristic inhibitor of cytochrome P450 enzymes.

Conceptual Basis of the Invention

A feature of certain fatty acid modifying enzymes such as fatty acyl desaturases and castor oleate hydroxylase is that they catalyze reactions in which an unactivated C—H bond is cleaved. To catalyze this energetically demanding cleavage, these fatty acid modifying enzymes utilize the high oxidizing power of molecular oxygen. There are presently two known classes of enzyme cofactors capable of this type of $O_2$-dependent chemistry. The haem-containing oxygenase including cytochromes P450 are one class. However, as noted above, substantial evidence indicates that oleate hydroxylase is not a cytochrome P450 enzyme. The second class of cofactor known to be capable of this type of $O_2$-dependent chemistry is less well characterized, but is typified by the bacterial enzyme methane monooxygenase (van de Loo et al., 1993). The cofactor in the hydroxylase component of methane monooxygenase is termed a μ-oxo bridged diiron cluster (FeOFe). The two iron atoms of the FeOFe cluster are liganded by protein-derived nitrogen or oxygen atoms, and are tightly redox-coupled by the covalently-bridging oxygen atom. The catalytic cycle of methane monooxygenase is not so well understood as that of the P450 oxygenases, but there are known differences and similarities. Rather than two discrete single-electron reductions of the haem cofactor, the FeOFe cluster accepts two electrons, reducing it to the diferrous state, before oxygen binding. Upon oxygen binding, it is likely that heterolytic cleavage also occurs, leading to a high valent oxoiron reactive species that is very similar to that of the haem cofactor, but stabilized by resonance rearrangements possible within the tightly coupled FeOFe cluster, rather than through a porphyrin-or protein-derived ligand. The stabilized high-valent oxoiron state of methane monooxygenase is capable of proton extraction from methane, followed by oxygen transfer, giving methanol.

The FeOFe cofactor has been shown to be directly relevant to plant fatty acid modifications by the demonstration that castor stearoyl-ACP desaturase contains this type of cofactor (Fox et al., 1993). This desaturase is a member of a small family of plant fatty acid desaturases that are soluble enzymes, whereas most other desaturases are membrane-bound. Putative iron-binding motifs have been identified in the castor stearoyl-ACP desaturase primary structure by comparison to other soluble enzymes containing the FeOFe cluster (Fox et al., 1993). These similar motifs, (D/E)—E—X—R—H, are characteristically spaced approximately 90 residues apart in a number of soluble diiron-oxo proteins, including methane monooxygenase. Recently, cDNA clones for several plant membrane-bound desaturases encoding microsomal and plastid ω-3 and ω-6 desaturases of several plant species have been isolated (Arondel et al., 1992; Iba et al., 1993; Okuley et al., 1994; Yadav et al., 1993). Of great interest is the identification of a similarly repeated motif in all of these sequences (Schmidt et al., 1993), the membrane-bound rat stearoyl-CoA desaturase (Thiede et al., 1986) and in two membrane-bound monooxygenases (Kok et al., 1989; Suzuki et al., 1991). This motif, H—X—X—H—H in the desaturases and H—X—X—X—H—H in the monooxygenases, may be the functional equivalent in membrane-bound FeOFe proteins of the (D/E)—E—X—R—H motif in the soluble FeOFe proteins. This suggests that the plant membrane bound desaturases may also accomplish oxygen-dependent fatty acid desaturation through an FeOFe cofactor.

Of the well-characterized FeOFe-containing enzymes, methane monooxygenase catalyses a reaction involving oxygen-atom transfer ($CH_4 \rightarrow CH_3OH$), while the FeOFe cluster of ribonucleotide reductase catalyses the oxidation of tyrosine to form a tyrosyl cation radical without oxygen-atom transfer. However, site-directed mutagenesis of Phe208 to Tyr resulted in the conversion of this enzyme to an oxygen transfer catalyst, Tyr208 being hydroxylated and shown to be acting as a ligand to one iron of the FeOFe cluster. Therefore, the argument made for the P450 oxygenases catalyzing a range of reactions through the use of the same reactive intermediate modulated by the electronic and structural environment provided by the protein, can also be applied to FeOFe-containing enzymes. Modifications of the active site of plant fatty acid oxidizing enzymes containing FeOFe clusters could thus alter the outcome of the reaction, including whether oxygen-atom transfer occurs or not.

On the basis of the foregoing considerations, we hypothesized that the castor oleate hydroxylase is a structurally modified fatty acyl desaturase, based upon three arguments. The first argument involves the taxonomic distribution of plants containing ricinoleic acid. Ricinoleic acid has been found in 12 genera of 10 families of higher plants (reviewed in van de Loo et al., 1993). Thus, plants in which ricinoleic acid occurs are found throughout the plant kingdom, yet close relatives of these plants do not contain the unusual fatty acid. This pattern suggests that the ability to synthesize ricinoleic acid has arisen several times independently, and is therefore a quite recent divergence. In other words, the ability to synthesize ricinoleic acid has evolved rapidly, suggesting that a relatively minor genetic change was necessary to accomplish it. Several mechanisms for such facile evolution of a new enzyme activity are envisaged. One mechanism would be for the modification of a gene normally encoding a fatty acid hydroxylase active in the epidermis and involved in the synthesis of a hydroxy-fatty acid cutin monomer. The other mechanism would be for modification of a gene encoding a microsomal fatty acid desaturase, such that instead of performing one type of oxidation reaction (desaturation) it now performs another (hydroxylation).

The second argument is that many biochemical properties of castor oleate-12-hydroxylase are similar to those of the microsomal desaturases, as discussed above (eg., both preferentially act on fatty acids esterified to the sn-2 position of phosphatidylcholine, both use cytochrome b5 as an intermediate electron donor, both are inhibited by cyanide, both require molecular oxygen as a substrate, both are thought to be located in the endoplasmic reticulum).

The third argument stems from the discussion of oxygenase cofactors above, in which it is suggested that the plant membrane bound fatty acid desaturases may have a μ-oxo bridged diiron cluster-type cofactor, and that such cofactors are capable of catalyzing both fatty acid desaturations and hydroxylations, depending upon the electronic and structural properties of the protein active site.

Taking these three arguments together, it was hypothesized that oleate-12-hydroxylase of castor endosperm is homologous to the microsomal oleate Δ12 desaturase found in all plants. When this invention was conceived, the structure of microsomal oleate Δ12 desaturase (also known as ω-6 desaturase) was not known. However, based on the high degree of homology between plastid and endoplasmic-reticulum-localized ω-3 desaturases (Iba et al., 1993), we further hypothesized that the microsomal Δ12 desaturase was homologous to the microsomal (ω-3) desaturase in particular, and also to the equivalent desaturases of the chloroplast inner envelope. A number of genes encoding microsomal ω-3 desaturases from various species have recently been cloned and substantial information about the structure of these enzymes is now known (Arondel et al., 1992; Iba et al., 1993; van de Loo and Somerville, 1993; Yadav et al., 1993). Hence in the following invention we teach how to use structural information about fatty acyl desaturases to isolate fatty acyl hydroxylase genes. Although, in the following example we reduce this invention to practice only for the castor oleate hydroxylase, this example unequivocally teaches the method by which any carbon-monoxide insensitive plant fatty acyl hydroxylase gene can be identified by one skilled in the art.

The invention is more fully described by reference to the following:

BRIEF DESCRIPTION OF THE DRAWINGS

FIG. 4. Partial uncorrected nucleotide sequences of castor cDNA clone pCRS677 (SEQ ID NO:1).

FIG. 5. Partial uncorrected nucleotide sequences of castor cDNA clone pCRS834 (SEQ ID NO:2).

FIGS. 6a and 6b. Abbreviated results from BLASTX-mediated comparison (SEQ ID NOS: 4, 6, 8, 10, 12 and 14) of all six translations (SEQ ID NOs: 3, 5, 7, 9, 11 and 13) of the partial nucleotide sequence of pCRS677 (FIG. 4) with the public sequence databases. The result shows that pCRS677 exhibits significant deduced amino acid sequence homology to an ω-3 desaturase from Brassica napus.

FIGS. 7a and 7b. Abbreviated results from BLASTX-mediated comparison (SEQ ID NOs: 16, 18, 20, 22, 24 and 26) of all six translations (SEQ ID Nos: 15, 17, 19, 21, 23 and 25) of the partial nucleotide sequence of pCRS834 (FIG. 5) with the public sequence databases. The result shows that pCRS834 exhibits significant deduced amino acid sequence homology to an ω-3 desaturase from Brassica napus.

FIGS. 8a and 8b. Comparison of the partial (uncorrected) nucleotide sequences of pCRS677 and pCRS834 (SEQ ID NOs: 27 and 28, respectively).

FIG. 9. Comparison of partial nucleotide sequences of ten castor cDNA clones (SEQ ID Nos: 29–38, respectively).

FIG. 10a and 10b. Nucleotide sequence of cDNA insert in pFL2 (SEQ. ID. NO. 39) and the deduced amino acid sequence (SEQ. ID. NO. 40) in single letter code. The positions of the putative iron-binding sites are highlighted.

FIG. 11. Comparison of deduced amino acid sequences of the cDNA insert in pFL2 and the Arabidopsis fad2 cDNA clone encoding (SEQ ID Nos: 41 and 42) an ω-6 fatty acyl desaturase.

FIGS. 12a, 12b and 12c. Northern blot analysis of pFL2 expression in castor. A $^{32}$P-labelled probe corresponding to ~700 bp of the 3' end of clone pFL2 was hybridized to poly(A)$^+$ RNA from leaves (L) and developing seeds (S) of castor. Panel A: the blot was exposed to film for 30 min. The migration of RNA standards (kb) is shown to the right. Panel B: the same blot was exposed for 16 h. Panel C: the same blot was hybridized to a $^{32}$P-labelled probe made from the Colletotrichum graminicola β-tubulin gene TUB2.

FIGS. 15a, 15b and 15c. Comparison of the nucleotide sequences of the castor fah12 cDNA insert in pFL2 and the Arabidopsis fad2 cDNA (SEQ ID Nos: 43 and 44).

FIG. 24. Mass spectrum of TMS-methyl ricinoleate standard.

SUMMARY OF THE INVENTION

Figure 1:
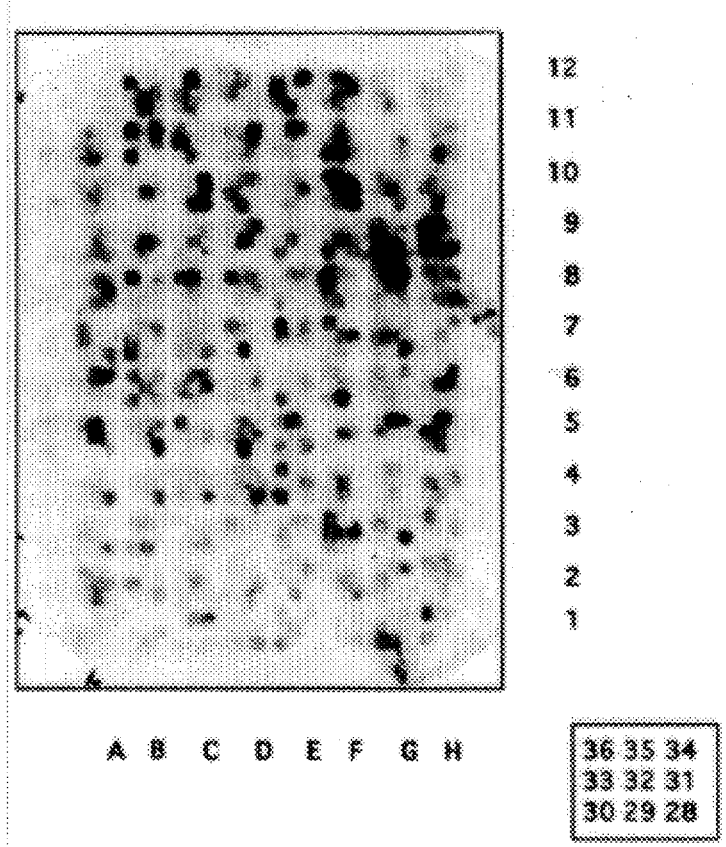
FIG. 1. Autoradiogram of a filter containing castor cDNA clones from 96-well plates #28–36 which had been replicated in a 3×3 grid and probed with $^{32}$P-labelled cDNA from developing castor seeds. The positions of the wells in the original 96-well plates is indicated by the numbers and letters along the edges. The position of clones from each 96-well plate relative to other 96-well plates is indicated in the box at the lower right corner.

This invention relates to plant fatty acyl hydroxylases. Methods to use conserved amino acid or nucleotide sequences to obtain plant fatty acyl hydroxylases are described. Also described is the use of cDNA clones encoding a plant hydroxylase to produce hydroxylated fatty acids in transgenic plants.

In a first embodiment, this invention is directed to nucleic acid sequences which encode a plant oleate hydroxylase. This includes sequences which encode biologically active plant oleate hydroxylase as well as sequences which are to be used as probes, vectors for transformation or cloning intermediates. All or a portion of the amino acid sequence, the genomic sequence or cDNA sequence of plant oleate hydroxylase is intended.

Of special interest are recombinant DNA constructs which can provide for the transcription or transcription and translation (expression) of the plant oleate hydroxylase sequence. In particular, constructs which are capable of transcription or transcription and translation in plant host cells are preferred. Such constructs may contain a variety of regulatory regions including transcriptional initiation regions obtained from genes preferentially expressed in plant seed tissue.

In a second aspect, this invention relates to the presence of such constructs in host cells, especially plant host cells which have an expressed plant oleate hydroxylase therein.

In yet a different aspect, this invention relates to a method for producing a plant oleate hydroxylase in a host cell or progeny thereof via the expression of a construct in the cell. Cells containing a plant oleate hydroxylase as a result of the production of the plant oleate hydroxylase encoding sequence are also contemplated herein.

In a different embodiment, this invention relates to methods of using a DNA sequence encoding a plant oleate hydroxylase for the modification of the proportion of hydroxylated fatty acids produced within a cell, especially plant cells. Plant cells having such a modified hydroxylated fatty acid composition are also contemplated herein.

In a further aspect of this invention, plant oleate hydroxylase proteins and sequences which are related thereto, including amino acid and nucleic acid sequences, are contemplated.

Plant oleate hydroxylase exemplified herein includes a *Ricinus communis* (castor) oleate hydroxylase. This exemplified oleate hydroxylase may be used to obtain other plant fatty acid hydroxylases of this invention.

DETAILED DESCRIPTION OF THE INVENTION

A genetically transformed plant of the present invention which accumulates hydroxylated fatty acids can be obtained by expressing the double-stranded DNA molecules described in this application.

A plant oleate hydroxylase of this invention includes any sequence of amino acids, such as a protein, polypeptide or peptide fragment, or nucleic acid sequences encoding such polypeptides, obtainable from a plant source which demonstrates the ability to catalyze the production of hydroxyoleic acid from CoA, ACP or lipid-linked substrates under plant enzyme reactive conditions. By "enzyme reactive conditions" is meant that any necessary conditions are available in an environment (i.e., such factors as temperature, pH, lack of inhibiting substances) which will permit the enzyme to function.

Preferential activity of a plant oleate hydroxylase toward a particular fatty acyl substrate is determined upon comparison of hydroxylated fatty acid product amounts obtained per different fatty acyl substrates. For example, by "oleate preferring" is meant that the hydroxylase activity of the enzyme preparation demonstrates a preference for oleate-containing substrates over other substrates. Although the precise substrate of the oleate desaturase is not known, it is thought to be an oleic acid moiety which is esterified to a phospholipid such as phosphatidylcholine, phosphatidylethanolamine, phosphatidic acid or a neutral lipid such as diacylglycerol or a Coenzyme-A thioester. As noted above, significant activity has been observed in radioactive labelling studies using other fatty acyl substrates (Howling et al., 1972) indicating that the substrate specificity is for a family of related fatty acyl compounds. Of particular interest, we envision that the castor oleate hydroxylase may be used for production of 12-hydroxy-9-octadecenoic acid (ricinoleate), 12-hydroxy-9-hexadecenoic acid, 14-hydroxy-11-eicosenoic acid, 16-hydroxy-13-docosenoic acid, 9-hydroxy-6-octadecenoic acid by expression in plants species which produce the non hydroxylated precursors. We also envision production of additionally modified fatty acids such as 12-hydroxy-9,15-octadecadienoic acid that result from desaturation of hydroxylated fatty acids (eg., 12-hydroxy-9-octadecenoic acid in this example).

As noted above, a plant oleate hydroxylase of this invention will display activity toward fatty acyl substrates. During biosynthesis of lipids in a plant cell, fatty acids are typically covalently bound to acyl carrier protein (ACP), coenzyme A (CoA) or various cellular lipids. Plant oleate hydroxylases which display preferential activity toward lipid-linked acyl substrate are especially preferred because they are likely to be closely associated with normal pathway of storage lipid synthesis in immature embryos. However, activity toward acyl-CoA substrates or other synthetic substrates, for example, is also contemplated herein.

Other plant oleate hydroxylases are obtainable from the specific exemplified sequences provided herein. Furthermore, it will be apparent that one can obtain natural and synthetic plant oleate hydroxylases including modified amino acid sequences and starting materials for synthetic-protein modeling from the exemplified plant oleate hydroxylase and from plant oleate hydroxylases which are obtained through the use of such exemplified sequences. Modified amino acid sequences include sequences which have been mutated, truncated, increased and the like, whether such sequences were partially or wholly synthesized. Sequences which are actually purified from plant preparations or are identical or encode identical proteins thereto, regardless of the method used to obtain the protein or sequence, are equally considered naturally derived.

Thus, one skilled in the art will readily recognize that antibody preparations, nucleic acid probes (DNA and RNA) and the like may be prepared and used to screen and recover "homologous" or "related" oleate hydroxylases from a variety of plant sources. Typically, nucleic acid probes are labeled to allow detection, preferably with radioactivity although enzymes or other methods may also be used. For immunological screening methods, antibody preparations either monoclonal or polyclonal are utilized. Polyclonal antibodies, although less specific, typically are more useful in gene isolation. For detection, the antibody is labeled using radioactivity or any one of a variety of second antibody/enzyme conjugate systems that are commercially available.

Homologous sequences are found when there is an identity of sequence and may be determined upon comparison of sequence information, nucleic acid or amino acid, or through hybridization reactions between a known oleate hydroxylase and a candidate source. Conservative changes, such as Glu/Asp, Val/Ile, Ser/Thr, Arg/Lys and Gln/Asn may also be considered in determining sequence homology. Typically, a lengthy nucleic acid sequence may show as little as 50–60% sequence identity, and more preferably at least about 70% sequence identity, between the target sequence and the given plant oleate hydroxylase of interest excluding any deletions which may be present, and still be considered related. Amino acid sequences are considered homologous by as little as 25% sequence identity between the two complete mature proteins. (See generally, Doolittle, R.F., OF URFS and ORFS, University Science Books, Calif., 1986.)

A genomic or other appropriate library prepared from the candidate plant source of interest may be probed with conserved sequences from the plant oleate hydroxylase to identify homologously related sequences. Use of an entire cDNA or other sequence may be employed if shorter probe sequences are not identified. Positive clones are then analyzed by restriction enzyme digestion and/or sequencing. When a genomic library is used, one or more sequences may be identified providing both the coding region, as well as the transcriptional regulatory elements of the oleate hydroxylase gene from such plant source. Probes can also be considerably shorter than the entire sequence. Oligonucleotides may be used, for example, but should be at least about 10, preferably at least about 15, more preferably at least 20 nucleotides in length. When shorter length regions are used for comparison, a higher degree of sequence identity is required than for longer sequences. Shorter probes are often particularly useful for polymerase chain reactions (PCR), especially when highly conserved sequences can be identified (See Gould, et al., 1989 for examples of the use of PCR to isolate homologous genes from taxonomically diverse species).

When longer nucleic acid fragments are employed (>100 bp) as probes, especially when using complete or large cDNA sequences, one would screen with low stringencies (for example 40°–50° C. below the melting temperature of the probe) in order to obtain signal from the target sample with 20–50% deviation, i.e., homologous sequences. (Beltz, et al. 1983).

In a preferred embodiment, a plant oleate hydroxylase of this invention will have at least 67% overall amino acid sequence similarity with the exemplified plant oleate hydroxylase. This level of similarity is sufficient to distinguish the castor oleate hydroxylase from the Arabidopsis fad2 gene product which encodes a Δ12 (or ω6) desaturase. In particular, oleate hydroxylases which are obtainable from an amino acid or nucleic acid sequence of a castor oleate hydroxylase (See, FIG. 10) are especially preferred. The plant oleate hydroxylases may have preferential activity toward longer or shorter chain fatty acyl substrates. Plant fatty acyl hydroxylases having oleate-12-hydroxylase activity and eicosenoate-14-hydroxylase activity are both considered homologously related proteins because of in vitro evidence, noted in the introduction, that the castor oleate hydroxylase will act on substrates other than oleate. As noted above, hydroxylated fatty acids may be subject to further enzymatic modification by other enzymes which are normally present or are introduced by genetic engineering methods. For example, 14-hydroxy-11,17-eicosadienoic acid, which is present in some Lesquerella species (Smith 1985), is thought to be produced by desaturation of 14-hydroxy-11-eicosenoic acid.

Again, not only can sequences such as shown in FIG. 10 be used to identify homologous plant fatty acyl hydroxylases, but the resulting sequences obtained therefrom may also provide a further method to obtain plant fatty acyl hydroxylases from other plant sources. In particular, PCR may be a useful technique to obtain related plant fatty acyl hydroxylases from sequence data provided herein. One skilled in the art will be able to design oligonucleotide probes based upon sequence comparisons or regions of typically highly conserved sequence. Of special interest are polymerase chain reaction primers based on the conserved regions of amino acid sequence between the castor oleate hydroxylase and the Arabidopsis fad2 shown in FIG. 11. Details relating to the design and methods for a PCR reaction using these probes is described more fully in the examples.

It should also be noted that the fatty acyl hydroxylases of a variety of sources can be used to investigate fatty acid hydroxylation events in a wide variety of plant and in vivo applications. Because all plants appear to synthesize fatty acids via a common metabolic pathway, the study and/or application of one plant fatty acid hydroxylase to a heterologous plant host may be readily achieved in a variety of species.

Once the nucleic acid sequence is obtained, the transcription, or transcription and translation (expression), of the plant fatty acyl hydroxylases in a host cell is desired to produce a ready source of the enzyme and/or modify the composition of fatty acids found therein in the form of free fatty acids, esters (particularly esterified to glycerolipids or as components of wax esters) or ethers. Other useful applications may be found when the host cell is a plant host cell, in vitro and in vivo.

For example, by increasing the amount of an oleate hydroxylase available to the plant, an increased percentage of ricinoleate or lesqueroleate (14-hydroxy-11-eicosenoic acid) may be provided.

Oleate Hydroxylase

By this invention, a mechanism for the biosynthesis of ricinoleic acid in plants is demonstrated. Namely, that a specific plant oleate hydroxylase having preferential activity toward fatty acyl substrates is involved in the accumulation of hydroxylated fatty acids in at least some plant species. The use of the terms ricinoleate or ricinoleic acid is intended to include the free acids, the ACP and CoA esters, the salts of these acids, the glycerolipid esters (particularly the triacylglycerol esters), the wax esters, and the ether derivatives of these acids.

The determination that plant fatty acyl hydroxylases are active in the in vivo production of hydroxylated fatty acids suggests several possibilities for plant enzyme sources. Hydroxylated fatty acids are found in some natural plant species in abundance. For example, three hydroxy fatty acids related to ricinoleate occur in major amounts in seed oils from various Lesquerella species. Of particular interest, Lesquerolic acid is a 20 carbon homolog of ricinoleate with two additional carbons at the carboxyl end of the chain (Smith 1985). Other natural plant sources of hydroxylated fatty acids are seeds of the Linum genus (van de Loo et al., 1993), seeds of Wrightia species, Lycopodium species, Strophanthus species, Convolvulaces species, Calendula species and many others (Gunstone et al., 1986).

Plants having significant presence of ricinoleate are preferred candidates to obtain naturally-derived oleate hydroxylases. However, it will also be recognized that other plant sources which do not have a significant presence of ricinoleate may be readily screened as other enzyme sources. For example, *Lesquerella densipila* contains a diunsaturated 18 carbon fatty acid with a hydroxyl group (Gunstone et al., 1986) that is thought to be produced by an enzyme that is closely related to the castor oleate hydroxylase, according to the theory on which this invention is based. In addition, a comparison between oleate- preferring plant fatty acyl hydroxylases and between plant fatty acyl hydroxylases which introduce hydroxyl groups at positions other than the 12-carbon or on substrates other than oleic acid may yield insights for protein modeling or other modifications to create synthetic hydroxylases as discussed above. For example, on the basis of information gained from structural comparisons of the Δ12 desaturases and the oleate hydroxylase, genetic modifications may be made in the structural genes for Δ15 desaturases that convert these desaturases to 15-hydroxylases (on 18 carbon fatty acids). Since the difference between a hydroxylase and a desaturase concerns the disposition of one proton, it is contemplated that by systematically changing the charged groups in the region of the enzyme near the active site, this change can be effected.

Especially of interest are fatty acyl hydroxylases which demonstrate activity toward fatty acyl substrates other than oleate, or which introduce the hydroxyl group at a location other than the C12 carbon. As noted above, such fatty acids may be obtained by expressing the oleate hydroxylase gene in plant species such as oilseed rape that contain suitable substrates other than oleate. As described above, other plant sources may also provide sources for these enzymes through the use of protein purification, nucleic acid probes, antibody preparations, protein modeling, or sequence comparisons, for example, and of special interest are the respective amino acid and nucleic acid sequences corresponding to such plant fatty acyl hydroxylases. Also as previously described, once nucleic acid sequence is obtained for the given plant hydroxylase, further plant sequences may be compared and/or probed to obtain homologously related DNA sequences thereto and so on.

Genetic Engineering Applications

As is well known in the art, once a cDNA clone encoding a plant oleate hydroxylase is obtained, it may be used to obtain its corresponding genomic nucleic acid sequences.

The nucleic acid sequences which encode plant fatty acyl hydroxylases may be used in various constructs, for example, as probes to obtain further sequences from the same or other species. Alternatively, these sequences may be used in conjunction with appropriate regulatory sequences to increase levels of the respective hydroxylase of interest in a host cell for the production of hydroxylated fatty acids or study of the enzyme in vitro or in vivo or to decrease or increase levels of the respective hydroxylase of interest for some applications when the host cell is a plant entity, including plant cells, plant parts (including but not limited to seeds, cuttings or tissues) and plants.

A nucleic acid sequence encoding a plant oleate hydroxylase of this invention may include genomic, cDNA or mRNA sequence. By "encoding" is meant that the sequence corresponds to a particular amino acid sequence either in a sense or anti-sense orientation. By "extrachromosomal" is meant that the sequence is outside of the plant genome of which it is naturally associated. By "recombinant" is meant that the sequence contains a genetically engineered modification through manipulation via mutagenesis, restriction enzymes, and the like. A cDNA sequence may or may not encode pre-processing sequences, such as transit or signal peptide sequences. Transit or signal peptide sequences facilitate the delivery of the protein to a given organelle and are frequently cleaved from the polypeptide upon entry into the organelle, releasing the "mature" sequence. The use of the precursor DNA sequence is preferred in plant cell expression cassettes.

Furthermore, as discussed above, the complete genomic sequence of the plant oleate hydroxylase may be obtained by the screening of a genomic library with a probe, such as a cDNA probe, and isolating those sequences which regulate expression in seed tissue. In this manner, the transcription and translation initiation regions, introns, and/or transcript termination regions of the plant oleate hydroxylase may be obtained for use in a variety of DNA constructs, with or without the oleate hydroxylase structural gene. Thus, nucleic acid sequences corresponding to the plant oleate hydroxylase of this invention may also provide signal sequences useful to direct transport into an organelle 5' upstream non-coding regulatory regions (promoters) having useful tissue and timing profiles, 3' downstream non-coding regulatory region useful as transcriptional and translational regulatory regions and may lend insight into other features of the gene.

Once the desired plant oleate hydroxylase nucleic acid sequence is obtained, it may be manipulated in a variety of ways. Where the sequence involves non-coding flanking regions, the flanking regions may be subjected to resection, mutagenesis, etc. Thus, transitions, transversions, deletions, and insertions may be performed on the naturally occurring sequence. In addition, all or part of the sequence may be synthesized. In the structural gene, one or more codons may be modified to provide for a modified amino acid sequence, or one or more codon mutations may be introduced to provide for a convenient restriction site or other purpose involved with construction or expression. The structural gene may be further modified by employing synthetic adapters, linkers to introduce one or more convenient restriction sites, or the like.

The nucleic acid or amino acid sequences encoding a plant oleate hydroxylase of this invention may be combined with other non-native, or "heterologous", sequences in a variety of ways. By "heterologous" sequences is meant any sequence which is not naturally found joined to the plant oleate hydroxylase, including, for example, combination of nucleic acid sequences from the same plant which are not naturally found joined together.

The DNA sequence encoding a plant oleate hydroxylase of this invention may be employed in conjunction with all or part of the gene sequences normally associated with the oleate hydroxylase. In its component parts, a DNA sequence encoding oleate hydroxylase is combined in a DNA construct having, in the 5' to 3' direction of transcription, a transcription initiation control region capable of promoting transcription and translation in a host cell, the DNA sequence encoding plant oleate hydroxylase and a transcription and translation termination region.

Potential host cells include both prokaryotic and eukaryotic cells. A host cell may be unicellular or found in a multicellular differentiated or undifferentiated organism depending upon the intended use. Cells of this invention may be distinguished by having a plant oleate hydroxylase foreign to the wild-type cell present therein, for example, by having a recombinant nucleic acid construct encoding a plant oleate hydroxylase therein.

Depending upon the host, the regulatory regions will vary, including regions from viral, plasmid or chromosomal genes, or the like. For expression in prokaryotic or eukaryotic microorganisms, particularly unicellular hosts, a wide variety of constitutive or regulatable promoters may be employed. Expression in a microorganism can provide a ready source of the plant enzyme. Among transcriptional initiation regions which have been described are regions from bacterial and yeast hosts, such as *E. coli*, *B. subtilis*, *Saccharomyces cerevisiae*, including genes such as beta-galactosidase, T7 polymerase, tryptophan E and the like.

For the most part, the constructs will involve regulatory regions functional in plants which provide for modified production of plant oleate hydroxylase with resulting modification of the fatty acid composition. The open reading frame, coding for the plant oleate hydroxylase or functional fragment thereof will be joined at its 5' end to a transcription initiation regulatory region such as the wild-type sequence naturally found 5' upstream to the oleate hydroxylase structural gene. Numerous other transcription initiation regions are available which provide for a wide variety of constitutive or regulatable, e.g., inducible, transcription of the structural gene functions. Among transcriptional initiation regions used for plants are such regions associated with the structural genes such as for nopaline and mannopine synthases, or with napin, soybean β-conglycinin, oleosin, 12S storage protein, the cauliflower mosaic virus 35S promoters and the like. The transcription/translation initiation regions corresponding to such structural genes are found immediately 5' upstream to the respective start codons. In embodiments wherein the expression of the oleate hydroxylase protein is desired in a plant host, the use of all or part of the complete plant oleate hydroxylase gene is desired; namely all or part of the 5' upstream non-coding regions (promoter) together with the structural gene sequence and 3' downstream non-coding regions may be employed. If a different promoter is desired, such as a promoter native to the plant host of interest or a modified promoter, i.e., having transcription initiation regions derived from one gene source and translation initiation regions derived from a different gene source, including the sequence encoding the plant oleate hydroxylase of interest, or enhanced promoters, such as double 35S CaMV promoters, the sequences may be joined together using standard techniques.

For such applications when 5' upstream non-coding regions are obtained from other genes regulated during seed maturation, those preferentially expressed in plant embryo tissue, such as transcription initiation control regions from the *B. napus* napin gene, or the Arabidopsis 12S storage protein, or soybean β-conglycinin (Bray et al., 1987), are desired. Transcription initiation regions which are preferentially expressed in seed tissue, i.e., which are undetectable in other plant parts, are considered desirable for fatty acid modifications in order to minimize any disruptive or adverse effects of the gene product.

Regulatory transcript termination regions may be provided in DNA constructs of this invention as well. Transcript termination regions may be provided by the DNA sequence encoding the plant oleate hydroxylase or a convenient transcription termination region derived from a different gene source, for example, the transcript termination region which is naturally associated with the transcript initiation region. Where the transcript termination region is from a different gene source, it will contain at least about 0.5 kb, preferably about 1–3 kb of sequence 3' to the structural gene from which the termination region is derived.

Plant expression or transcription constructs having a plant oleate hydroxylase as the DNA sequence of interest for increased or decreased expression thereof may be employed with a wide variety of plant life, particularly, plant life involved in the production of vegetable oils for edible and industrial uses. Most especially preferred are temperate oilseed crops. Plants of interest include, but are not limited to rapeseed (Canola and high erucic acid varieties), flax, sunflower, safflower, cotton, Cuphea, soybean, peanut, coconut and oil palms and corn. Depending on the method for introducing the recombinant constructs into the host cell, other DNA sequences may be required. Importantly, this invention is applicable to dicotyledons and monocotyledons species alike and will be readily applicable to new and/or improved transformation and regulation techniques.

The method of transformation is not critical to the current invention; various methods of plant transformation are currently available. As newer methods are available to transform crops, they may be directly applied hereunder. For example, many plant species naturally susceptible to Agrobacterium infection may be successfully transformed via tripartite or binary vector methods of Agrobacterium mediated transformation. In addition, techniques of microinjection, DNA particle bombardment, electroporation have been developed which allow for the transformation of various monocot and dicot plant species.

In developing the DNA construct, the various components of the construct or fragments thereof will normally be inserted into a convenient cloning vector which is capable of replication in a bacterial host, e.g., *E. coli*. Numerous vectors exist that have been described in the literature. After each cloning, the plasmid may be isolated and subjected to further manipulation, such as restriction, insertion of new fragments, ligation, deletion, insertion, resection, etc., so as to tailor the components of the desired sequence. Once the construct has been completed, it may then be transferred to an appropriate vector for further manipulation in accordance with the manner of transformation of the host cell.

Normally, included with the DNA construct will be a structural gene having the necessary regulatory regions for expression in a host and providing for selection of transformant cells. The gene may provide for resistance to a cytotoxic agent, e.g., antibiotic, heavy metal, toxin, etc., complementation providing prototropy to an auxotrophic host, viral immunity or the like. Depending upon the number of different host species the expression construct or components thereof are introduced, one or more markers may be employed, where different conditions for selection are used for the different hosts.

It is noted that the degeneracy of the DNA code provides that some codon substitutions are permissible of DNA sequences without any corresponding modification of the amino acid sequence.

As mentioned above, the manner in which the DNA construct is introduced into the plant host is not critical to this invention. Any method which provides for efficient transformation may be employed. Various methods for plant cell transformation include the use of Ti- or Ri-plasmids, microinjection, electroporation, infiltration, imbibition, DNA particle bombardment, liposome fusion, DNA bombardment or the like. In many instances, it will be desirable to have the construct bordered on one or both sides of the T-DNA, particularly having the left and right borders, more particularly the right border. This is particularly useful when the construct uses A. tumefaciens or A. rhizogenes as a mode for transformation, although the T-DNA borders may find use with other modes of transformation.

Where Agrobacterium is used for plant cell transformation, a vector may be used which may be introduced into the Agrobacterium host for homologous recombination with T-DNA or the Ti- or Ri-plasmid present in the Agrobacterium host. The Ti- or Ri-plasmid containing the T-DNA for recombination may be armed (capable of causing gall formation) or disarmed (incapable of causing gall), the latter being permissible, so long as the vir genes are present in the transformed Agrobacterium host. The armed plasmid can give a mixture of normal plant cells and gall.

In some instances where Agrobacterium is used as the vehicle for transforming plant cells, the expression construct bordered by the T-DNA border(s) will be inserted into a broad host spectrum vector, there being broad host spectrum vectors described in the literature. Commonly used is pRK2 or derivatives thereof. See, for example, Ditta et al., (1980), which are incorporated herein by reference. Included with the expression construct and the T-DNA will be one or more markers, which allow for selection of transformed Agrobacterium and transformed plant cells. A number of markers have been developed for use with plant cells, such as resistance to kanamycin, the aminoglycoside G418, hygromycin, or the like. The particular marker employed is not essential to this invention, one or another marker being preferred depending on the particular host and the manner of construction.

For transformation of plant cells using Agrobacterium, explants may be combined and incubated with the transformed Agrobacterium for sufficient time for transformation, the bacteria killed, and the plant cells cultured in an appropriate selective medium. Once callus forms, shoot formation can be encouraged by employing the appropriate plant hormones in accordance with known methods and the shoots transferred to rooting medium for regeneration of plants. The plants may then be grown to seed and the seed used to establish repetitive generations and for isolation of vegetable oils.

The invention now being generally described, it will be more readily understood by reference to the following examples which are included for purposes of illustration only and are not intended to limit the present invention.

EXAMPLES

In the experimental disclosure which follows, all temperatures are given in degrees centigrade (°), weights are given in grams (g), milligram (mg) or micrograms (µg), concentrations are given as molar (M), millimolar (mM) or micromolar (µM) and all volumes are given in liters (l), microliters (µl) or milliliters (ml), unless otherwise indicated.

Isolation of Castor Oleate Hydroxylase cDNA Overview

Ricinoleic acid is specific to the seed tissue of castor, and is not found in vegetative tissues (Canvin 1963; James et al., 1965). Therefore, a differential screening approach was used to enrich for cDNA clones which were expressed in seeds but not in leaves. A large number of clones with these properties were retained and partial nucleotide sequence information was obtained from each clone. The nucleotide sequences were translated in all six possible reading frames and the deduced amino acids sequences were compared to the sequences of plant fatty acid desaturases in order to identify clones which exhibited amino acid sequence homology. Candidate clones were then placed under transcriptional control of a plant promoter and introduced into transgenic plants of tobacco and Arabidopsis thaliana. Finally, the presence of ricinoleic acid in the seed oils of these transgenic plants was verified by gas chromatography and mass spectrometry. The various steps involved in this process are described in detail below.

RNA Isolation

Total RNA was purified from developing stage III to stage V (Greenwood and Bewley, 1982) castor cellular endosperm plus embryo by the technique of Puissant and Houdebine (1990) with minor modifications. Briefly, tissue (10 g) was powdered in liquid nitrogen and divided into 8 tubes. The frozen powder was suspended in 5 ml buffer (4M guanidinium thiocyanate, 25 mM sodium citrate pH 7.0, 0.5 % sarkosyl, 0.1M 2-mercaptoethanol). The following reagents were added, punctuated by vortexing of the tube: 2M sodium acetate pH 4.0 (0.5 ml), phenol (5 ml), and chloroform (1.0 ml). Following incubation on ice for 15 min, the tubes were centrifuged at 10,000 g (7000 rpm) for 10 min. Isopropanol (5 ml) was added to the upper phase and incubated on ice for 10 min, followed by centrifugation as before. The RNA pellet was dislodged with 1 ml 4 M LiCl and transferred to a microfuge tube. The original tube was rinsed with 0.5 ml more LiCl and the pellet vortexed for 5 min in the combined liquid. RNA was pelleted in a microfuge (10 min), then resuspended again in 1 ml 4M LiCl and pelleted again. The pellet was thoroughly resuspended in TE/0.5% SDS (750 µl) and extracted with an equal volume of chloroform/isoamyl alcohol (24:1). The aqueous phase was extracted a second time before precipitation of RNA by the addition of 2M sodium acetate (100 µl) and isopropanol (600 ul). RNA was pelleted and resuspended in water, and represented the purified total RNA fraction.

Production of cDNA Libraries

PolyA$^+$RNA (10ug) was prepared from total castor RNA (1.5 mg) by two passes down an oligo (dT) spin column. This was done using a kit (catalog number 5302-600750) according to the instructions of the manufacturer (5 Prime—3 Prime, Inc. 5603 Arapahoe, Boulder, Colo. 80303 USA).

A λZAPII cDNA library was prepared using a ZAP-cDNA synthesis kit (Stratagene, 11011 North Torrey Pines Road, La Jolla, Calif. 92037. catalog number 200400). First and second strand cDNA was synthesized from polyA$^+$ RNA (5 µg) using an oligo (dT) primer and Moloney-Murine Leukemia Virus Reverse Transcriptase exactly as described by the manufacturers instructions. Following addition of EcoRI linkers and digestion with XhoI the cDNA was purified on a sephacryl S-400 (Sigma chemical Company, PO box 14508, St Louis, Mo. 63178, USA. Catalog number S-400-HR) spin column prepared according to the instructions in the ZAP-cDNA synthesis kit. The cDNA was loaded onto the column which had been equilibrated in 10 mM Tris-Cl (pH 8.0), 1 mMEDTA. cDNA (400 ng) eluting in the second fraction was concentrated by ethanol precipitation. Half of this cDNA (200 ng) was ligated into Lambda ZAPII digested with XhoI and EcoRI according to the instructions supplied with the ZAP-cDNA synthesis kit. Construction of the λZAPII library included directional cloning, so that 5' ends of the inserts should be found at the T3 side of the polylinker. The entire ligation was packaged using Gigapack packaging extract (Stratagene, 11011 North Torrey Pines Road, La Jolla, Calif. 92037. catalog number 200211) according to the manufacturers instruction and plated on *E. coli* strain XL1-Blue (Stratagene, 11011 North Torrey Pines Road, La Jolla, Calif.). This yielded $1 \times 10^5$ primary plaques which were eluted in SM buffer (100 mM NaCl, 8 mM MgSO$_4$50 mM Tris-HCl pH 7.5, 0.1% gelatin per liter) and stored at 4° C.

A second cDNA library was prepared in the plasmid vector pYES2 (Invitrogen). Complementary DNA was prepared using a kit ("Librarian IV", Invitrogen) according to the instructions of the manufacturer. First strand cDNA (1.65 µg) was synthesized from poly(A)$^+$ RNA (5 µg) by priming with oligo dT and extension by avian myeloma virus reverse transcriptase. The RNA was nicked by *E. coli* RNaseH, forming primers for second-strand cDNA synthesis by *E. coli* DNA polymerase I. Any nicks in the dsDNA were repaired with *E. coli* DNA ligase. Ends of the dsDNA were made blunt with T4 DNA polymerase for ligation of BstX1 non-palindromic linkers. The cDNA was size-selected by agarose-gel electrophoresis, and molecules larger than ~750 bp were ligated into the BstXI-digested pYES2.0 vector and transformed into *E. coli* strain INV1αF', yielding four pools containing a total of $1.42 \times 10^6$ transformants.

Differential Screening of λZAPII Library

Phage from the castor λZAPII library was picked randomly into eighteen separate 96-well plates (designated #1–9 and #28–36). These were replicated onto bacterial lawns prepared by adding 0.2 ml of a saturated L-broth culture of *E. coli* strain XL1-blue (Stratagene) to 5 ml of molten top agar and pouring the mixture onto the surface of agar-solidified L-broth medium in a 132 mm petri dish. Each 96-well plate was replicated using a 96-prong device which could be lowered onto the lawn through a 3×3 array of guides. The blunt ~1 mm diameter prongs carried sufficient phage to give plaques of consistent size, without significant encroachment between neighboring plaques. Multiple filters, each representing 864 identifiable clones, were lifted from the resulting plaques and screened with $^{32}$P-labelled first-strand cDNA probes reverse transcribed from leaf or developing endosperm/embryo poly(A)$^+$ RNA. Triplicate nylon filters (Hybond N$^+$, Amersham) were lifted from these plaques. DNA was fixed to the filters by placing them on filter paper moist with denaturing solution (0.5M NaOH, 1.5M NaCl; 5 min), neutralizing solution (0.5M Tris-Cl pH 7.4, 1.5M NaCl; 5 min), and 2×SSC (0.3M NaCl, 0.03M Na-Citrate, pH 7.0). The filters were then air-dried, with no further fixation of the DNA. The filters were screened with the various probes described below. For plates 1–9, polyadenylic acid (1 µg ml$^{-1}$) was added to the hybridization solution, and results for plates 1–9 were obtained from a phosphor-imager (Molecular Dynamics) rather than from autoradiographs. Exposure times were: plates 1–9, 21 h (note that phosphor imaging is several-fold more sensitive than autoradiography); plates 28–36 leaf probe 3 days, seed probe 24 h, redundant-clone probe 1.5 h.

Probes for differential screening plates 1–9 were prepared as follows. Poly(A)$^+$RNA (1 µg) from seed or leaf in a volume of 17 µl was heated to 70° C. for 5 min, then chilled in ice-water, and added to the reaction tube, to a final volume of 50 µl. The reaction mixture contained in addition: 50 U RNasin (Promega), 1× reverse transcriptase buffer (Boehringer-Mannheim), 20 ng/µl oligo(dT)$_{12-18}$, 1 mM each of dGTP, dATP, dTTP, 4.8 µM dCTP (unlabelled), 100 µCi α-$^{32}$P dCTP (3000 Ci mmol$^{-1}$), 40 U Avian Myeloma Virus Reverse Transcriptase. The reaction was incubated at 42° C. for 60 min. The reaction was stopped and RNA removed by addition of EDTA (to 16 mM), SDS (to 0.4%), NaOH (to 0.4M) and incubation at 65° C. for 30 min. The probe was neutralized with 6 µl 2M HCl and 20 µl 1M Tris-Cl, pH7.4, then precipitated with 375 µl EtOH in the presence of 0.7M ammonium acetate and 10 µg denatured carrier (salmon sperm) DNA. After incubation at –20° C. for ~3 h, DNA (~60% of total radioactivity) was pelleted by centrifugation for 15 min, and resuspended in 200 µl water and added to the filters.

For plates 28–36, first-strand cDNA was made using the same RNA (0.5 µg seed, 1.2 µg leaf) in a reverse transcription reaction similar to that described above, but using unlabelled nucleotides and all other components from a reverse transcription kit (Promega). The RNA was hydrolysed and the cDNA was neutralized as described above, and then purified by batch chromatography on glass (GeneClean, Bio101). The cDNA was then labelled by random hexamer priming using 100 µCi α$^{32}$P dCTP. The probes were precipitated as described above, and heated to 100° C. (5 min) before addition to the filters. Incorporation of radioactivity was ~60% (leaf probe) or ~30% (seed probe).

Only those clones were selected which gave no detectable signal with the probe derived from leaf mRNA, and did not give a very strong signal with the probe derived from seed mRNA. Plates 1–9 were processed in this manner, from which the first batch of cDNA sequences were obtained (described below).

Of 864 possible plaques from plates 1–9, 10 did not develop and 15 were occluded by bubbles separating the plaque and filter, leaving 839 clones with DNA on the filter. Of these, 162 (19.3%) were scored as having a strong seed signal, while 280 (33.4%) gave no detectable signal with the leaf probe. Of these 280, 222 were not among the previous category and were selected for sequencing. These results therefore indicated that 222 of 839, or 26.5% of clones, were in the category "seed-specific and not highly abundant". Of the 162 clones having a strong seed signal, only 58 appeared to be seed specific.

Figure 2:
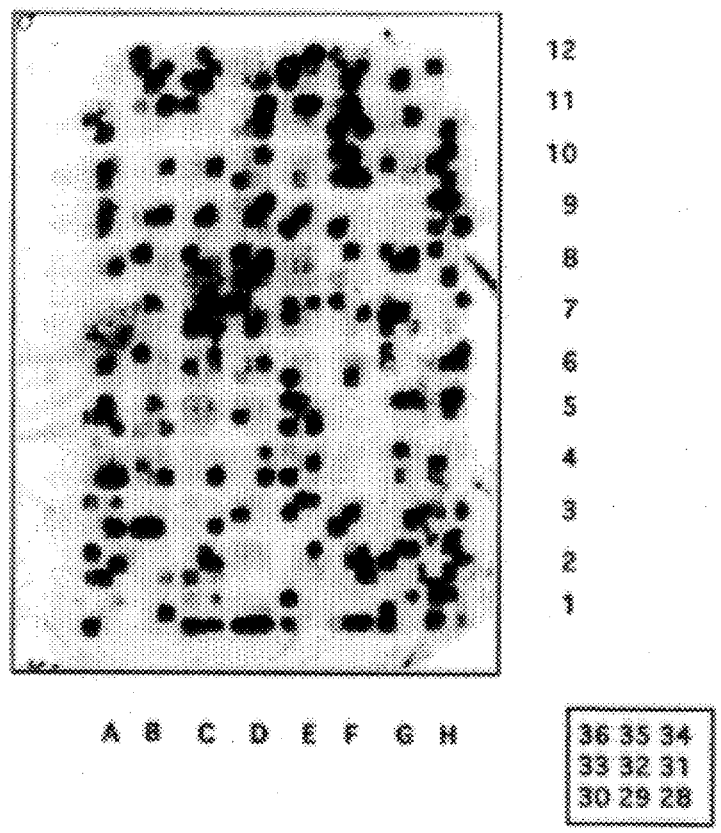
FIG. 2. Autoradiogram of a filter containing castor cDNA clones from 96-well plates #28–36 which had been replicated in a 3×3 grid and probed with $^{32}$P-labelled cDNA from developing castor leaves. The positions of the wells in the original 96-well plates is indicated by the numbers and letters along the edges. The position of clones from each 96-well plate relative to other 96-well plates is indicated in the box at the lower right corner.
Figure 3:
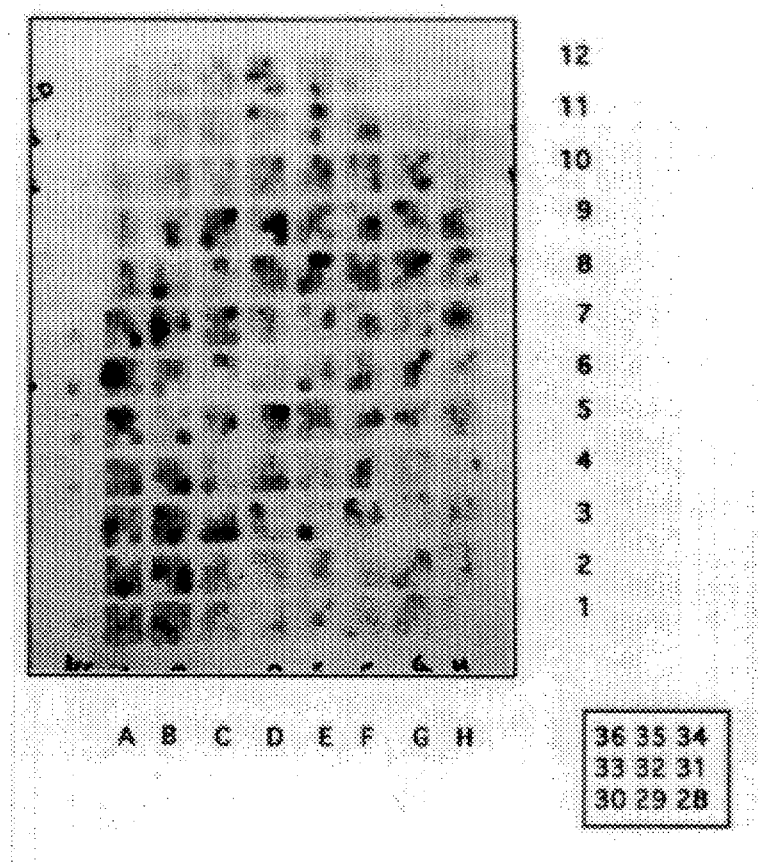
FIG. 3. Autoradiogram of a filter containing castor cDNA clones from 96-well plates #28–36 which had been replicated in a 3×3 grid and probed with $^{32}$P-labelled DNA from redundant clones sequenced in batch 1. The positions of the wells in the original 96-well plates is indicated by the numbers and letters along the edges. The position of clones from each 96-well plate relative to other 96-well plates is indicated in the box at the lower right corner.

Some changes were made when screening plates 28–36 for the second sequencing batch. The seed mRNA and leaf mRNA probes were made by random priming using first-strand cDNA as a template, in an attempt to gain maximum incorporation of radioactivity into less-abundant sequences. In addition, a probe was made from the pooled insert DNA of clones that were sequenced several times in the first batch so that fewer redundant sequences would be obtained. A mixed probe was made from some of the most redundant clones as follows. Plasmid DNA of highly represented clones (Table 1) were digested with BamHI and KpnI and the inserts purified from agarose gels. DNA of these inserts was pooled and ~600 ng labelled with 100 µCi α$^{32}$P dCTP (~80% incorporation) by random priming as described above. Screening results were obtained directly from autoradiograms. An example of the autoradiograms is presented in FIGS. 1–3.

For plates 28–36, 851 of a possible 864 plaques were represented on the filter, and of these 851, 370 (43.5%) gave a strong seed signal, 512 (60.2%) gave no detectable leaf signal, and 141 (16.6%) gave a signal with the probe made from redundant sequences (the effectiveness of screening with this particular probe is discussed below). This resulted in the selection of 348 (40.9% of 851) clones to be sequenced.

TABLE 1

List of highly expressed castor cDNA clones of known function from plates 1–9.

Ribosomal proteins: Clones pCRS262, pCRS312, pCRS356, pCRS358, pCRS377, pCRS396, pCRS407, pCRS409, pCRS416, pCRS426, pCRS432, pCRS442, pCRS446.

12S seed storage protein: Clones pCRS267, pCRS269, pCRS298, pCRS404, pCRS405, pCRS408, pCRS434, pCRS443, pCRS453, pCRS454.

2S seed storage protein: Clones pCRS281, pCRS328, pCRS337, pCRS362, pCRS375, pCRS431.

Meat shock proteins: Clones pCRS264, pCRS348, pCRS397.

Enolase: Clones pCRS330, pCRS380, pCRS415, pCRS439.

DNA Sequencing

The differential screens described above gave a total of 570 lambda phage clones selected for sequencing. The phage were converted to plasmids by a slightly modified (scaled-down) version of the Stratagene protocol provided with the purchase of the λZAP cDNA synthesis kit. Briefly, in a 15 ml conical tube, combine 200 µl XL1-Blue cells, 20 µl phage suspension from 96-well plate, and 1 µl R408 helper phage (Stratagene). Incubate at 37° C. for 15 min, then add 5 ml 2×YT medium (per liter: 10 g NaCl, 10 g yeast extract, 16 g bacto-tryptone), and shake at 37° C. for 3 h. Heat to 70° C. for 20 min, centrifuge 5 min at 4000 g, and store supernatant (phagemid stock) at 4° C. To obtain colonies, mix 200 µl XL1-Blue cells and 1 µl of 1/100 dilution of phagemid stock, incubate 15 min at 37° C. plate 100 µl on LB agar medium containing 100 µg/ml ampicillin and incubate at 37° C. until colonies form (ca. 18 h).

Plasmid DNA was prepared from $E.$ $coli$ cultures (5 ml, LB medium containing 100 mg $l^{-1}$ ampicillin) using "Magic Minipreps" (Promega) according to the instructions of the manufacturer. DNA was analyzed spectrophotometrically for DNA concentration, and submitted to the Michigan State University, Plant Research Laboratory Sequencing Facility for automated sequencing on Applied Biosystems 373A DNA sequenators. The T3 primer (Applied Biosystems, Foster City, Calif.) was generally used to prime the sequencing reactions. Sequence data was manually edited to remove vector/linker sequences, and truncated at the point where sequence quality declined substantially as indicated by a high proportion of ambiguous nucleotide identifications. These edited sequences (typically 400–500 nucleotides) were compared with the public sequence databases by electronic submission of the sequence to the BLAST server (BLAST@ncbi.nlm.nih.gov) provided by the National Center for Biotechnology Information, Bethesda, Md. DNA sequences were compared in all reading frames to the non-redundant translated-nucleotide and protein sequence databases (Swiss-Prot 24.0 or 25.0 plus weekly updates; PIR 35.0, 36.0, or 37.0; GenBank Release 75.0, 76.0, or 77.0, plus daily updates; and EMBL Release 34.0 or 35.0, plus daily updates) by the program blastx (Altschul et al., 1990) in the months March-July, 1993.

Of the 526 clones sequenced, 58 gave sequence data which was not considered informative because of poor quality or the presence of only vector sequences. Sequence from the 468 informative clones was analyzed by the blastx program, leading to the putative identification of 213 (46%) of them by the criteria that these partial sequences had blastx scores greater than 80. DNA sequences generated in this study have been deposited in the NCBI database, dbEST (database for Expressed Sequence Tags), as identification numbers 39704–40169, and in GenBank, as accession numbers T14820–T15266. The sequences will not be made publicly accessible until after the filing date of this patent application.

Two clones pCRS677 (dbEST accession number 40094) and pCRS834 (dbEST accession number 40142) have sequence similarity with plant membrane-bound desaturase genes. The original uncorrected partial nucleotide sequences for pCRS677 and pCRS834 on which this conclusion was based are shown in FIGS. 4 and 5, respectively. The homology is shown in FIGS. 6A and 6B where the deduced amino acid sequence of translation frame +2 obtained from clone pCRS677 is compared to the deduced amino acid sequence of the microsomal ω3 fatty acyl desaturase from $Brassica$ $napus$ and a cDNA from $Vigna$ $radiata$ that is also thought to be a fatty acid desaturase (Iba et al., 1993). A similar result is shown in FIGS. 7A and 7B for clone pCRS834. Therefore these clones were selected for further analysis as putative clones of the oleate hydroxylase.

Isolation and Sequencing of cDNA Clone pFL2

Comparison of the initial partial (uncorrected) sequence data of pCRS677 and pCRS834 obtained with the T3 primer (FIGS. 4 and 5), indicated that these are probably independent clones derived from the same gene (FIGS. 8A and 8B). Although there are a number of differences between the two nucleotide sequences, these are mostly located at the 3' end of the sequences and are, therefore, thought to be sequencing errors resulting from the inaccuracy of the base-calling routines of the automated sequenator used to obtain these partial sequences.

The insert of pCRS677 (~700 bp) was used as a probe to screen a castor pYES2.0 library by colony hybridization at high stringency. Three 100 mm plates of each of the four pools of the pYES2.0 cDNA library were screened by the same methods described above. In brief, $E.$ $coli$ cells containing the pYES2.0 library were plated at a density of approximately 39,000 colonies per 100 mm petri dish on agar solidified LB medium containing ampicillin (100 µg/ml) and grown at 37° C. until small colonies were visible. A nitrocellulose filter (Schleicher & Schell BA85) was laid on each plate, its position marked, and lifted off to a fresh plate, the adhering colonies now facing upwards. Care was necessary that both plate and filter were not too moist, to avoid smearing of the colonies. The original plate was incubated for 5 h at 37° C. to recover colonies, while the filters were processed as follows. Each filter was sequentially placed, colony side up, on Whatman 3 MM paper moist with 10% SDS (3 min), denaturing solution (0.5M NaOH, 1.5 M NaCl; 5 min), neutralizing solution (0.5M Tris-Cl pH 7.4, 1.5M NaCl; 5 min), and 2×SSC (0.3M NaCl, 0.03M Na-Citrate, pH 7.0). The filters were then air-dried for ca. 1 min before pressing twice between sheets of filter paper to remove cell debris. After air-drying a further 30 min, DNA was fixed to the filters by baking in vacuo at 80° C. for 1–2 h.

The filters were prehybridised in a minimal volume of 4×SET (0.6M NaCl, 0.12M Tris-Cl pH 7.4, 8 mM EDTA), 0.1% Na-pyrophosphate, 0.2% SDS, 100 µg/ml heparin, at 65° C., before addition of the probe and hybridization overnight. The pCRS677 insert was excised with BamHI and ApaI, gel-purified, $^{32}$P-labelled by random priming and purified of unincorporated nucleotides by ethanol precipitation in the presence of ammonium acetate. This probe was hybridized to the filters overnight at 65° C. The filters were washed three times in 2×SSC, 0.1% SDS at 65° C., then exposed to X-ray film.

In the primary screen of 47,000 colonies, 84 hybridizing colonies were obtained. The first 28 of these positive colonies were purified by streaking for single colonies. All 28 of the primary positives were positive in the secondary screen, indicating an overall frequency of one positive clone per 560 clones in the cDNA library. DNA prepared from the 28 purified clones was digested with restriction enzymes and analyzed by agarose gel electrophoresis. The enzymes BamHI and XhoI cut the vector on either side of the cloning site, and therefore should excise the inserted DNA when used together. With one exception, all clones had a single fragment smaller than ~800 bp, or an ~800 bp fragment plus one or two additional fragments. Clone 4avi did not fit this pattern. A double-digest with XbaI and HindIII should, similarly, excise the insert. All clones analyzed yielded only one fragment, ranging in size between ~700 bp and ~2.2 kb, except clone 4avi, which had an insert of ~4 kb. Due to minor technical difficulties, however, clones 2ci, 3cv, 4cii, 4aiii, 4ci, 4aii, 4ai, and 3ciii, were not analyzed by digestion with XbaI and HindIII. The majority of clones had one HincII site in the insert, with the exception of clones 3cv, 4cii, 4aiii, 4ci, 3cii, 4aii, 3cvii, and 3cvi, which either lacked this site or had an additional site. Taken together, these results indicate that most of the 28 clones purified had a similar restriction pattern, with 9 possible exceptions. This indicated that most, if not all, represent the same gene. Of the majority of clones, which appeared to have similar restriction patterns but varying insert sizes, 10 were used to obtain partial sequence data shown in FIG. 9. This sequence data indicated that these 10 clones had highly similar sequences and were probably derived from the same gene. It is concluded that this one class of clones is present in the pYES2.0 library at a frequency between 1/560 and 1/1120. The longest clone, 3cvii, was 113 bp longer than the next longest, 3civ-1. However, the first 305 bp of 3cvii showed no similarity to the overlapping portion of 3civ-1 or several other clones of similar length, which were, however, all highly similar in sequence to each other (FIG. 9). It was concluded that the first 305 bp of the cDNA in clone 3cvii contained extraneous DNA, not related to pCRS677 (nor any other known sequence). Further sequence data was obtained only from clone 3civ-1, hereafter designated pFL2. The gene corresponding to the insert in pFL2 is hereafter designated by the symbol fah12 (fatty acid 12-hydroxylase).

DNA Sequencinq

Nucleotide sequences of cloned DNA fragments can be obtained by a variety of commonly used methods. DNA sequencing of the DNA fragments described herein was performed with an ABI Catalyst-8000 robot and an ABI373A DNA sequencer using dye terminator or dye primer sequencing reactions. Sequence data was analyzed using the programs DNASIS and PROSIS (Hitachi Company).

The sequence of the insert in clone pFL2 is shown in FIGS. 10A and 10B. The sequence entails 1448 bp of contiguous DNA sequence (SEQ ID NO:39). The clone encodes a 186 bp 5' untranslated region (i.e. nucleotides preceding the first ATG codon), an 1161 bp open reading frame, and a 101 bp 3' untranslated region, including a short (9 bp) poly(A) tail. The open reading frame encodes a 387 amino acid protein with a predicted molecular weight of 44406.8 (SEQ ID NO: 40). The amino terminus lacks features of a typical signal peptide (yon Heijne, 1985). The predicted sequence of the Brassica napus fad3 microsomal desaturase also lacks a typical signal peptide (Arondel et al., 1992).

The exact translation-initiation methionine has not been experimentally determined, but on the basis of deduced amino acid sequence homology to the microsomal ω6 fatty acyl desaturase (noted below) is thought to be the methionine encoded by the first ATG codon at nucleotide 187.

Comparison of the pFL2 nucleotide and deduced amino acid sequences with sequences of membrane-bound desaturases (Table 2) indicates that pFL2 is homologous to these genes. Sequence similarity between pFL2 and these desaturase genes is considerably weaker than similarities among the desaturase genes. An alignment of the deduced amino acid sequences of the insert in pFL2 and the Arabidopsis fad2 cDNA which encodes an endoplasmic reticulum-localized ω-6 (Δ12) desaturase (Okuley et al., 1994) is shown in FIG. 11. The overall homology between the two gene products was 67% and the length of the sequences differed by only 4 amino acid residues. Thus, in view of the fact that the two genes are from distantly related plants, the high degree of sequence homology indicates that the gene products are of similar function.

The deduced amino acid sequence of pFL2 (FIGS. 10A and 10B) contains the conserved histidine-rich repeats (HXXHH) also found in all known plant membrane-bound desaturases (Arondel et al., 1992; Iba et al., 1993; Yadav et al., 1993; Okuley et al., 1994).

TABLE 2

Amino acid (AA) and nucleotide (NT) sequence similarity between the cDNA in pFL2 and membrane-bound desaturase genes

| Organism | Gene | % Identity AA | % Identity NT | Function |
| --- | --- | --- | --- | --- |
| Ricinus communis | fad7 | 38.6 | 47.1 | ω3 desaturase |
| Brassica napus | fad3 | 37.4 | 46.5 | ω3 desaturase |
| A. thaliana | fad7 | 35.5 | 47.4 | ω3 desaturase |
| A. thaliana | fad2 | 67 | 65.4 | ω6 desaturase |

Northern Blot Analysis

Ricinoleic acid is generally found only in seed oils and oleate-12-hydroxylase activity is only found in the developing seeds of castor. Therefore, an important criterion in discriminating between an ω6 fatty acyl desaturase and oleate hydroxylase is that the oleate hydroxylase gene is expected to be expressed more highly in tissues which have high level of ricinoleate than in other tissues whereas all plant tissues should contain mRNA for an ω6 fatty acyl desaturase since diunsaturated fatty acids are found in the lipids of all tissues in most or all plants. Therefore, it was of great interest to determine whether pFL2 was also expressed only in seeds, or is also expressed in other tissues. This question was addressed by testing for hybridization of pFL2 to RNA purified from developing seeds and from leaves.

A northern blot of RNA from leaves and developing seeds from stage III to stage V (Greenwood and Bewley 1982) of castor was probed with the $^{32}$P-labelled insert of clone pCRS677, which corresponds to ~700 bp of the 3' end of pFL2.

Poly(A)$^+$ RNA prepared as described above from leaves and developing seeds was electrophoresed through an agarose gel containing formaldehyde (Iba et al., 1993). An equal quantity (3 μg) of RNA was loaded in both lanes, and RNA standards (0.16–1.77 kb ladder, Gibco-BRL) were loaded in a third lane. Following electrophoresis, RNA was transferred from the gel to a nylon membrane (Hybond N, Amersham) and fixed to the filter by exposure to UV light. A $^{32}$P-labelled probe was prepared from insert DNA of clone pCRS677 as above, and hybridized to the membrane overnight at 65° C., after it had been prehybridised for ~1 h. The hybridization solution contained 4×SET (0.6M NaCl, 0.12M Ttis-HCl pH 7.4, 8 mM EDTA), 0.1% sodium pyrophosphate, 0.2% SDS, 0.1% heparin, and 5% dextran sulphate. The blot was washed lo three times in 2×SSC, 0.1% SDS at room temperature, then exposed to X-ray film, and to a phosphor-imaging screen (Molecular Dynamics). A probe was subsequently made from the *Colletotrichum graminicola* β-tubulin gene TUB2 (Panaccione and Hanau, 1990) and hybridized to the same blot under the same conditions, except that the hybridization temperature was reduced to 58° C., and was exposed to X-ray film.

Brief (30 min) exposure of the blot to X-ray film revealed that the probe hybridized to a single band of ~1.67 kb, only in the seed RNA lane (FIG. 12, panel A). Upon overexposure (16 h) of the film, a band of similar size was detected in the leaf RNA lane, in addition to a second, larger, band in the seed RNA lane (FIG. 12, panel B). The blot was also exposed to a phosphor-imaging screen, for quantitation of probe hybridization. Total exposure to this screen in an area coveting the band in the leaf lane was $4.36 \times 10^4$ units above background. Total exposure in an area of equal size over the major band in the seed lane was $1.17 \times 10^7$ units above background, 268-fold more than in the leaf lane. The blot was re-probed with β-tubulin gene, which gave bands of equal intensity in the seed and leaf lanes (FIG. 12, panel C), verifying that equal quantities of undegraded RNA were loaded in the two lanes.

These results show that the fah12 gene corresponding to the clone pFL2 is highly and specifically expressed in seed of castor. Over-exposure of the Northern revealed a 268-fold weaker band of similar size in leaf RNA, but also a second band in seed RNA, suggesting that these bands are due to weak hybridization of pFL2 to related sequences, such as microsomal ω6 fatty acyl desaturases. In conjunction with knowledge of the nucleotide and deduced amino acid sequence, strong seed-specific expression of pFL2 is a useful indicator of the role of the enzyme in synthesis of hydroxylated fatty acids in the seed oil.

Southern Blot Analysis

Southern analysis was used to examine the copy number of genes in the castor genome corresponding to clone pFL2, and to examine whether related sequences could be detected in the castor genome, and in the genome of a different plant, in which oleate-12-hydroxylase is absent.

Genornic Arabidopsis DNA (1 μg) and genomic castor DNA (2 μg) were digested with EcoRI, BamHI, or HindIII, and separated in 0.7% agarose gel. A Southern blot was prepared as described in (Sambrook et al., 1989). The blot was prehybridised at 65° C. in a solution containing 4×SET (0.6M NaCl, 0.12M Tris-HCl pH 7.4, 8 mM EDTA), 0.1% sodium pyrophosphate, 0.2% SDS, and 100 μg/ml heparin. The probe was hybridized to the blot at 65° C. overnight in the same solution, except for the addition of 10% dextran sulphate. The blot was washed three times in 2×SSC, 0.1% SDS at room temperature then exposed to X-ray film. Arabidopsis was chosen for the negative control DNA because it has no known oleate-12-hydroxylase. The membrane was hybridized with the $^{32}$P-labelled insert of clone pFL2 at 65° C., and exposed to X-ray film.

Figure 13:
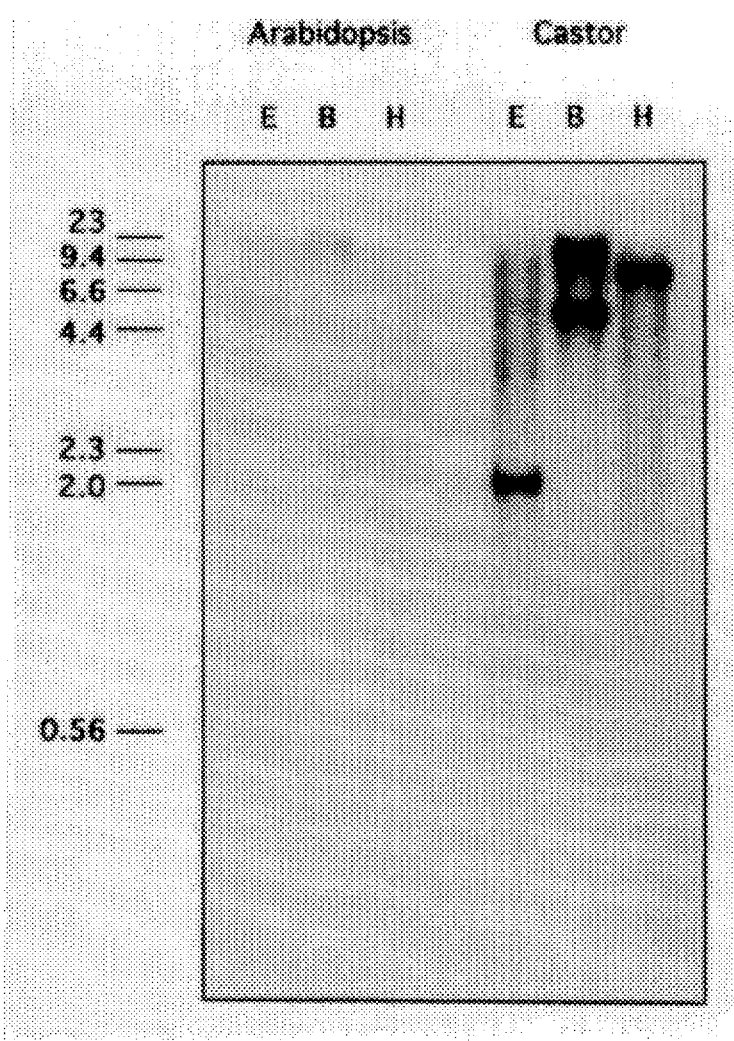
FIG. 13. A Southern blot of genomic DNA from Arabidopsis thaliana and castor (Ricinus communis) digested with restriction enzymes EcoRI (E), BamHI (B), or HindIII (H), was hybridized at high stringency (65° C.) with the $^{32}$P-labelled insert of clone pFL2. Migration of DNA standards (kb) is shown to the left.
Figure 14:
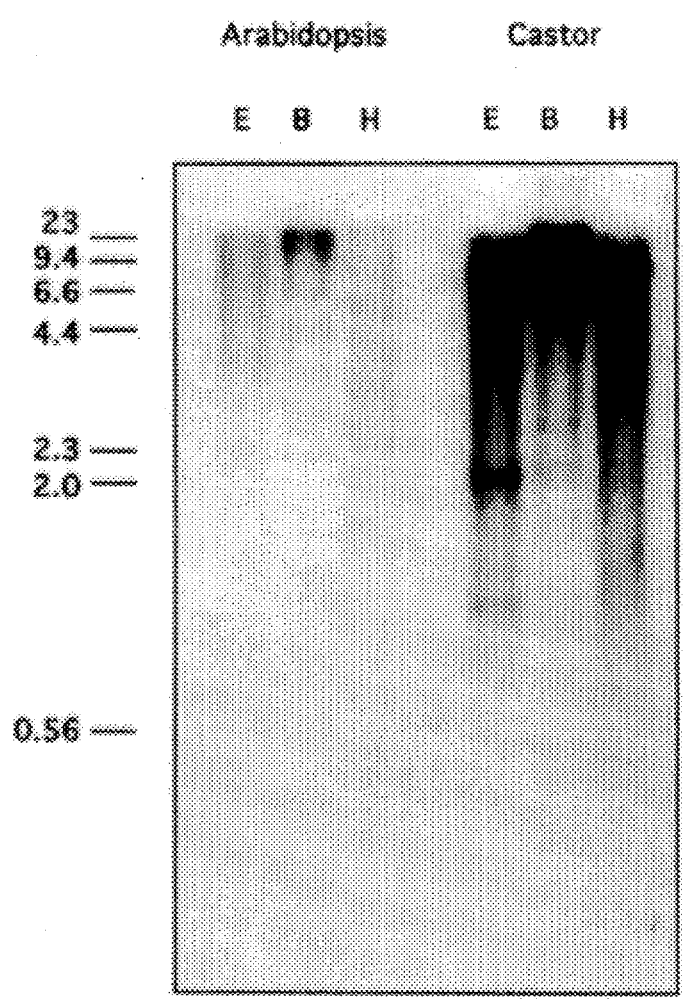
FIG. 14. A Southern blot of genomic DNA from Arabidopsis thaliana and castor (Ricinus communis) digested with restriction enzymes EcoRI (E), BamHI (B), or HindIII (H), was hybridized at moderate stringency (52° C.) with the $^{32}$P-labelled insert of clone pFL2. Migration of DNA standards (kb) is shown to the left.

The probe hybridized with a single band in each digest of castor DNA, but did not hybridize to the Arabidopsis DNA (FIG. 13), indicating that the fah12 gene from which pFL2 was transcribed is probably present in a single copy in the castor genome, and is not present in the Arabidopsis genome. The blot was then hybridized again, with an identical probe, but at less stringent hybridization conditions (52° C.) (FIG. 14). This revealed additional weakly-hybridizing bands in both castor and Arabidopsis. In castor DNA, a total of four bands were detected in both the EcoRI digest and the BamHI digest. In Arabidopsis DNA, four bands (EcoRI), five bands (BamHI), or possibly three bands (HindIII) were detected. These results suggest that at least one additional gene with sequence similarity to pFL2 occurs in both the castor and Arabidopsis genomes. Comparison of the nucleotide sequences of the castor fah12 cDNA and the Arabidopsis fad2 cDNA showed several regions of strong nucleotide sequence homology (FIGS. 15A, 15B and 15C). Thus, some or all of the bands of hybridization observed on low stringency Southern blots are due to hybridization of the fah12 clone to one or more genes for microsomal ω6 fatty acyl desaturase in both castor and Arabidopsis.

Expression of pFL2 in Transgenic Plants

There are a wide variety of plant promoter sequences which may be used to cause tissue-specific expression of cloned genes in transgenic plants. For instance the napin promoter and the acyl carrier protein promoters have previously been used in the modification of seed oil composition by expression of an antisense form of a desaturase (Knutson et al. 1992). Similarly, the promoter for the β-subunit of soybean β-conglycinin has been shown to be highly active and to result in tissue-specific expression in transgenic plants of species other than soybean (Bray et al., 1987). Thus, although we have used the cauliflower mosaic virus 35S promoter in the examples described here, other promoters which lead to seed-specific expression are preferred for the production of modified seed oil composition. Such modifications of the invention described here will be obvious to one skilled in the art.

Figure 16:
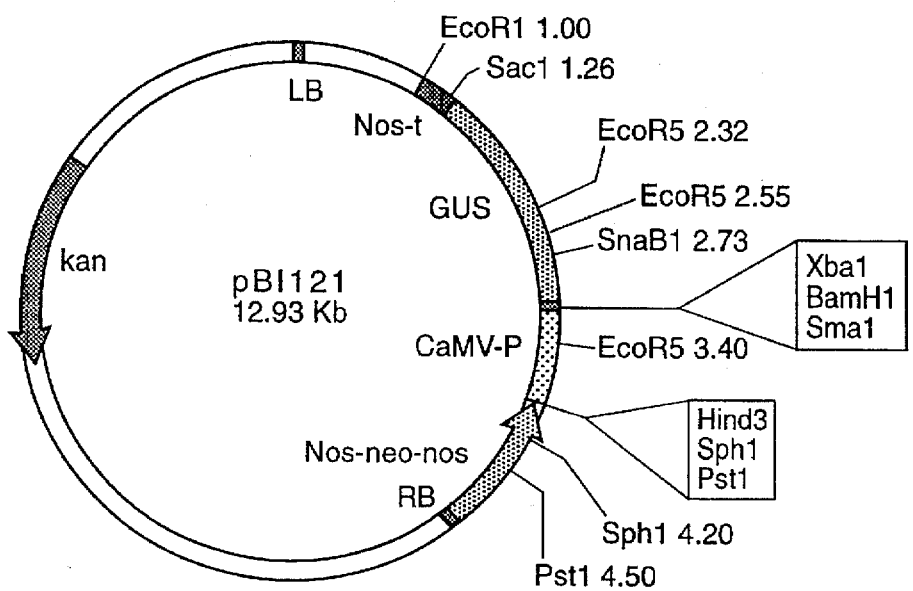
FIG. 16. Map of binary Ti plasmid pBI121.

Constructs for expression of castor oleate hydroxylase plant cells which utilize the CaMV35S promoter region are prepared as follows: The insert of clone pFL2 was ligated between the 35S promoter and nos terminator of the plant expression binary vector pBI121 (FIG. 16) (Clontech, Palo Alto, Calif.) in the correct orientation for expression of the open reading frame, by two independent cloning strategies.

The use of the vector pBI121, in which the only 3' cloning site is SacI, was complicated by the presence of a SacI site in the coding region of the pFL2 insert. In the first route, pFL2 was linearised with XbaI (which cuts at the 3' region flanking the insert), blunt-ended with the Klenow fragment of DNA polymerase I, then digested with BarnHI (which cuts at the 5' end of the insert), releasing the insert, which was gel-purified. The vector pBI121 (FIG. 16) was digested with SacI and blunt-ended with T4 DNA polymerase, then cut with BarnHI and treated with calf intestinal phosphatase to prevent religation with the excised β-glucuronidase fragment. The pFL2 insert was ligated to this pBI121 vector and used to transform *Escherichia coli* DH5α cells to kanamycin resistance. Plasmid DNA of transformants was digested with XbaI and SacI, and two dories (A4, B6) were chosen that had the 1.3 kb fragment indicating that the pFL2 cDNA was correctly inserted into the pBI121 vector. This was confirmed by the fact that SnaBI did not cut these clones (SnaBI cuts the β-glucuronidase gene), and EcoRI/HindIII released a band of appropriate size (~2.5 kb).

Figure 17:
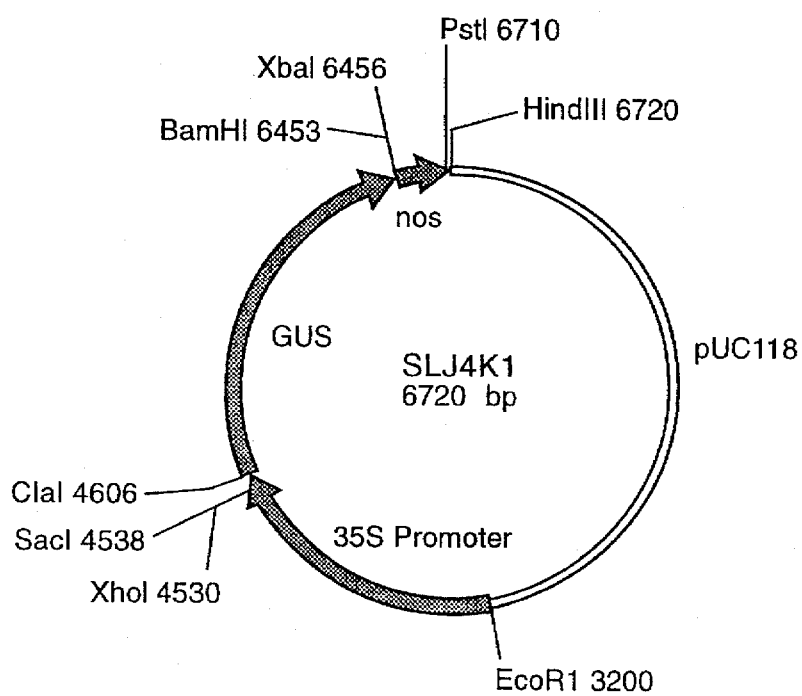
FIG. 17. Map of binary Ti plasmid pSLJ4K1.

In the second route, clone pFL2 was digested with XbaI and then partially digested with SacI. A band of ~1.45 kb representing the entire insert was isolated from a gel. The vector SLJ4K1 (FIG. 17) was obtained from Dr, J. Jones, Sainsbury Institute, John Innes center, Norwich, England. The plasmid was digested with XbaI and SacI, and the vector fragment was gel-purified. The pFL2 insert was ligated to this vector, transformed into DH5α, and checked for the presence of the 1.3 kb SacI insert fragment. Such a clone was then digested with EcoRI and HindIII, and this DNA was ligated to the large EcoRI/HindIII fragment of pBI121, transformed into DH5α and selected for both kanamycin resistance and ampicillin sensitivity. By this procedure, the entire (35S promoter)-(pFL2 insert)-(nos terminator) fragment derived from SLJ4K1 was used to replace the (35S promoter)-(β-glucuronidase)-(nos terminator) fragment of pBI121. The clones obtained were digested with SacI, and one done (9/18 3) which gave the appropriate 1.3 kb fragment was selected.

The three clones (A4 and B6 prepared by the first route, and 9/18 3 prepared by the second), plus the unmodified vector pBI121, were transformed into *Agrobacterium turaefaciens* strains GV3101 and LBA4404 by electroporation. GV3101 (Koncz and Schell, 1986) and LBA4404 (Ooms et al., 1982) contain disarmed Ti plasmids. Cells for electropotation were prepared as follows. GV3101 was grown in LB medium with reduced NaCl (5 gl⁻¹), and LBA4404 was grown in TY medium (5 gl⁻¹ bacto-tryptone, 3 gl⁻¹ yeast extract, pH 7.5). A 500 ml culture was grown to OD600=0.6, then centrifuged at 4000 rpm (GS-A rotor) for 5 min. The supernatant was aspirated immediately from the loose pellet, which was gently resuspended in 500 ml ice-cold water. The cells were centrifuged as before, resuspended in 30 ml ice-cold water, transferred to a 30 ml tube and centrifuged at 5000 rpm (SS-34 rotor) for 5 min. This was repeated three times, resuspending the cells consecutively in 30 ml ice-cold water, 30 ml ice-cold 15% dimethyl sulfoxide (DMSO), and finally in 4 ml ice-cold 15% DMSO. These cells were aliquoted, frozen in liquid nitrogen, and stored at −80° C. Electroporations employed a BTX instrument using cold 1 mm-gap cuvettes containing 40 µl cells and a minimal volume of DNA, a voltage of 1.44 KV, and 129 Ω resistance. The electroporated cells were diluted with 1 ml SOC medium (Sambrook et al., 1989, page A2) and incubated at 28° C. for 1–2 h before plating on medium containing kanamycin (50 mg l⁻¹).

EXAMPLE 1

Production of Ricinoleate in Transgenic Tobacco

A variety of methods have been developed to insert a DNA sequence of interest into the genome of a plant host to obtain the transcription or transcription and translation of the sequence to effect phenotypic changes. The following methods represent only one of many equivalent means of producing transgenic plants and causing expression of the hydroxylase gene.

*Nicotiana tabacura* SR-1 leaf explants were transformed according to Newman et al (1993) with minor modifications as noted below. Seeds of *Nicotiana tabacum* SR-1 are soaked in 95% ethanol for 2 min surface sterilized in a 1.0% solution of sodium hypochlorite containing a drop of Tween 20 for 45 min, and rinsed three times in sterile, distilled water. Seeds are then plated in Magenta boxes with 1/10th concentration of Murashige Skoog (MS) minimal organics medium (Gibco; Grand Island, N.Y.) supplemented with 30 g/L sucrose, 0.56 mM myo-inositol, 2.5 mM MES and adjusted to pH 5.7 and solidified with 0.8% Phytagar (Gibco). Seeds are germinated at 22° C in a 24 h photoperiod with cool fluorescent light of intensity approximately 50 µEinsteins per square meter per second (5E m⁻²s⁻¹). Axenic leaf pieces from 3 to 8 week old plants were transferred to No. 3 medium (MS salts, 30 g/L sucrose, 1.2 µM thiamine, 0.56 mM myoinositol, 1 µM indole-3-acetic acid, 10 µM benzylaminopurine, 2.5 mM MES and adjusted to ph 5.6 and solidified with 0.65% agar). After 3 days of incubation in continuous light of approximately 50 5E m⁻²s⁻¹, the leaf fragments were inoculated by pricking the leaves with sterile syringe needles dipped in fresh colonies of Agrobacterium. After 3 to 4 days the leaf fragments were transferred to No. 3 medium containing 200 µg/ml kanamycin and 500 µg/ml carbenicillin. Shoots which emerged during the following one to three months were transferred to Magenta boxes containing 0.65% agar-solidified MS medium containing 1% sucrose, 2 mg/L indolebutyric acid, 100 µg/ml kanamycin and 500 µg/ml carbenicillin to induce rooting. Rooted plants were transferred to soil and grown under natural light in a glasshouse with a mean daily temperature of 28 ° C. Twelve transgenic lines were obtained (Table 3).

The presence of the transgene in a number of the putative transgenic lines was verified by using the polymerase chain reaction to amplify the insert from pFL2. The primers used were HF2 =GCTCTTTTGTGCGCTCATTC and HR2= TCGACAGTCACCATTGCTCC (SEQ ID NOS: 45 and 46, respectively, which were designed to allow the amplification of a 700 bp fragment. Approximately 100 ng of genomic DNA was added to a solution containing 25 pmol of each primer, 1.5 U Taq polymerase (Boehringer Manheim), 200 uM of dNTPs, 50 mM KCl, 10 mM Tris.Cl (pH 9), 0.1% (v/v) Triton X-100, 1.5 mM MgCl₂, 3% (v/v) formamide, to a final volume of 25 µl. Amplifications conditions were: 4 min denaturation step at 94° C., followed by 30 cycles of 92° C. for 1 min, 55° C. for 1 min, 72° C. for 2 min. A final extension step dosed the program at 72 ° C. for 5 min. All putative transgenic lines tested gave a PCR pattern consistent with the expected genotype (see Table 3) confirming that the lines were, indeed, transgenic.

TABLE 3

Summary of transgenic tobacco lines

| Line obtained | Construct analyzed | Seeds done | Seeds produced | PCR | Ricinol. |
|---|---|---|---|---|---|
| Wild type | – | – | + | – | – |
| 8 | pBI121 | + | | – | |
| 2-1 | B6 | + | + | + | + |
| 2-2 | B6 | + | + | + | + |
| 6-1 | B6 | + | | + | |
| 9-1 | A4 | + | | + | |
| 9-3 | A4 | + | | | |
| 10-1 | B6 | + | | + | |
| 10-2 | B6 | + | | + | |
| 10-3 | B6 | + | | + | |
| 10-5 | B6 | + | | + | |
| 18-1 | B6 | + | | + | |
| 4/12-1 | pBI121 | + | + | – | – |

Figure 18:
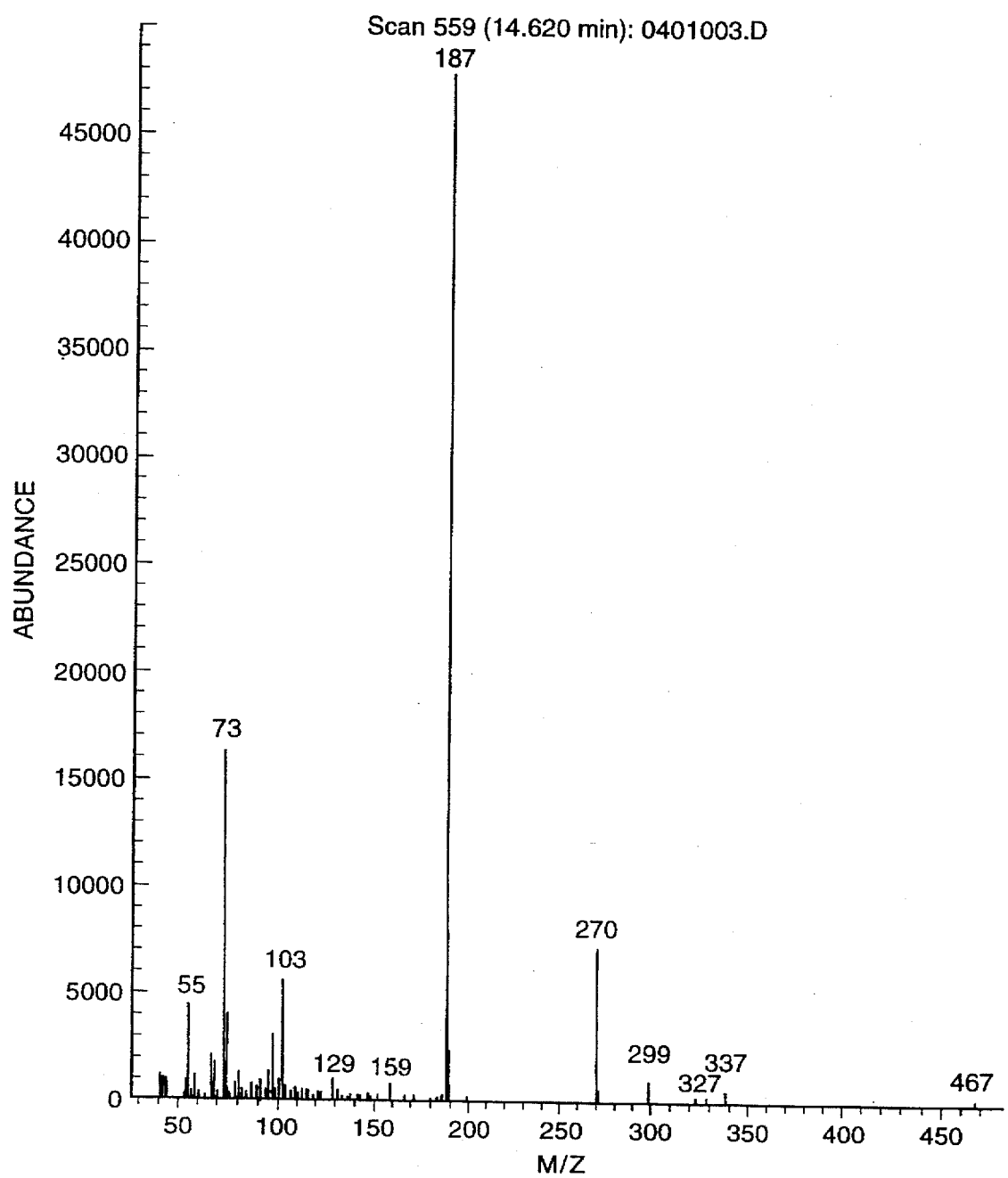
FIG. 18. Mass spectrum of TMS-methyl-ricinoleate
Figures 19A, 19B:
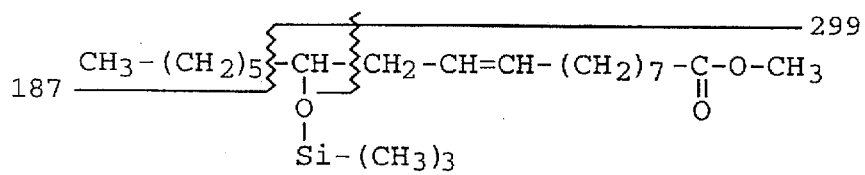
FIGS. 19a and 19b. Fragmentation pattern of TMS-methyl ricinoleate by mass spectrometry.

Transgenic tissues were analyzed by gas chromatography and mass spectrometry for the presence of ricinoleic acid. Calibration standards for the gas chromatograph were 1 µl samples of fatty acid methyl esters of an equal mixture of 16:0, 18:0, 18:1, 18:2 and 18:3 (0.125–0.25 mg/ml). Ricinoleic acid standards (Sigma) were esterified and silylated as described below, and injected at 5 or 25 mg/ml. The mass spectrum of TMS-methyl-ricinoleate is shown in FIG. 18. The fragmentation pattern resulting in the ions observed is explained in FIGS. 19A and 19B.

Duplicate seed samples from two independent fah12 transgenic tobacco lines (2-1 and 2-2), one transgenic tobacco line transformed with pBI121 (4/12-1) and one wild-type SR-1 tobacco line were used to prepare fatty acid methyl esters (FAMEs). FAMEs were prepared by placing 5 seeds in 1.5 ml of 1.0M methanolic HCl in a 13×100 mm glass screw-cap tube capped with a teflon-lined cap and heated to 80° C. for 2 hours. Upon cooling, 1 ml hexane:isopropanol (3:2) and 0.5 ml 0.2 M $Na_2SO_4$ were added and the FAMEs removed from the hexane phase. Approximately 1 µl of N, O-bis(Trimethylsilyl)trifluoroacetamide (BSTFA) was added (BSTFA, Pierce; 100 ml), to derivatize any hydroxyl groups. The reaction was carried out at 70 ° C. for 15 min. The products were dried under nitrogen, redissolved in 200 ml hexane and transferred to a gas chromatograph vial. Two ml of each sample were analyzed on a SP2330 glass capillary column (30 m, 0.75 mm ID, 0.20 mm film, Supelco), using a Hewlett-Packard 5890 II series Gas Chromatograph. The samples were not split, the temperature program was 150 ° C. (6 min) to 215 ° C. (4° C./min), and flame ionization detectors were used. Care was taken to elute out any carry-over material by injecting three hexane blanks after the standards.

TABLE 4

Fatty acid composition of fah12 transgenic tobacco seeds compared to control seeds. Values are mol % of total fatty acids.

| Sample | 16:0 | 18:0 | fatty 18:1 | acids 18:2 | 18:3 | ricinoleate |
|---|---|---|---|---|---|---|
| WTa | 10.1 | 2.65 | 12.25 | 73.65 | 1.05 | 0 |
| WTb | 10.3 | 2.75 | 12.60 | 72.79 | 1.13 | 0 |
| 4/12-1a | 10.41 | 2.40 | 11.63 | 74.23 | 1.14 | 0 |
| 4/12-1b | 10.44 | 2.70 | 11.55 | 73.57 | 1.27 | 0 |
| 2-1a | 10.62 | 2.83 | 11.78 | 73.19 | 1.14 | 0.05 |
| 2-1b | 10.53 | 2.61 | 11.81 | 73.58 | 1.09 | 0.04 |
| 2-2a | 10.95 | 2.42 | 10.98 | 74.11 | 1.07 | 0.09 |
| 2-2b | 11.09 | 2.92 | 11.08 | 73.56 | 0.99 | 0.07 |

Figure 20A:
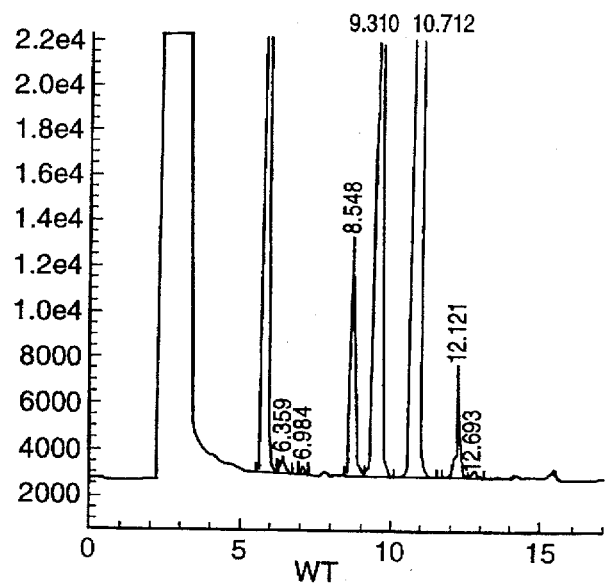
FIGS. 20a, 20b and 20c. Gas chromatograms of control and transgenic tobacco plants. The arrow indicates the peak of methyl-ricinoleate.
Figure 20B:
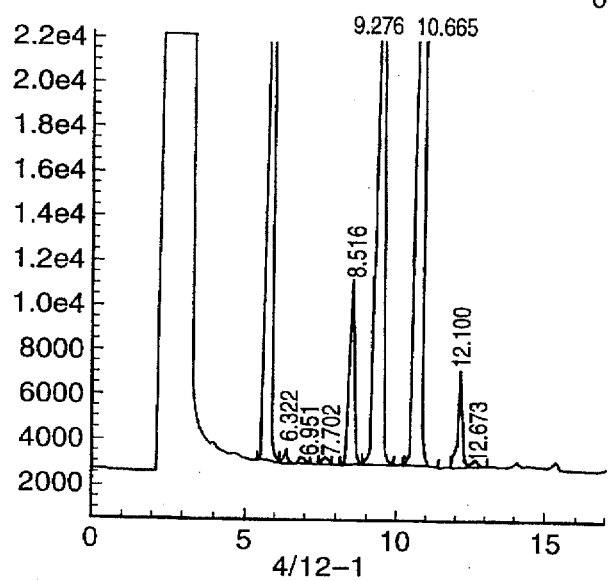
Figure 20C:
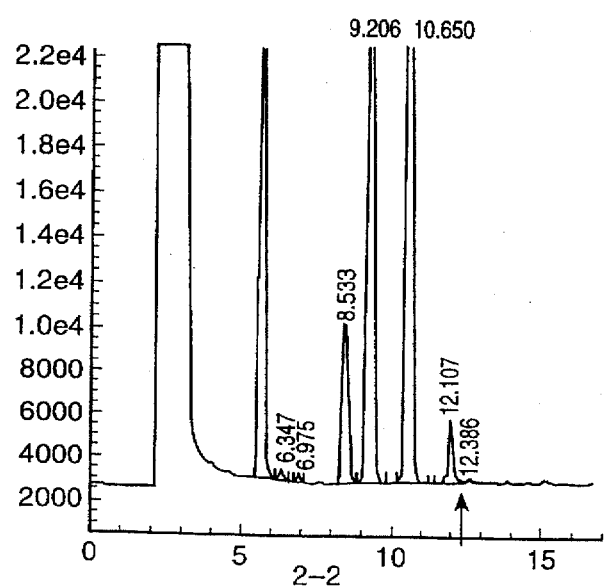

As shown in table 4, seed fatty acid composition for 2-1 and 2-2 are similar to both wild-type and 4/21-1 controls. However, a significant difference was observed in the gas chromatograms in the region of 12.35 to 12.44 min. A peak representing about 0.1% of the fatty acid content in the seed is consistently present in both 2-1 and 2-2 and absent in control wild-type and 4/21-1 seeds (FIGS. 20A, 20B and 20C). Under similar conditions, the elution time of the TMS-methyl-ricinoleate standard was 12.43 min. This preliminary result provided the first indication that fah12-containing transgenic plants 2-1 and 2-2 produced ricinoleic acid.

In order to confirm that the observed peak did correspond to TMS-methyl-ricinoleate, mass spectrometry was used. The objective was to determine if mass spectrums of the compounds eluting in the region of 12.35 to 12.44 min in the previous experiment could be unequivocally attributed to TMS-methyl-ricinoleate. In order to obtain clearer results, attention was focused on the 2-2 transgenic line seeds, which contained about twice as much of the target compound than 2-1 seeds. Seven samples of 20 seeds from the fah12 tobacco transgenic line 2—2 were analyzed by gas chromatography and mass spectrometry. Five samples of 20 wild-type tobacco seeds were used as a control. Three of the seven 2—2 samples were ground in 1 ml chloroform:methanol (2:1); the solvent was then evaporated under a stream of nitrogen prior to transesterification with methanolic HCl. The other samples were extracted directly from intact seeds without grinding as described above. Esterification and silylation steps were carried out as described above for all samples. To determine how complete TMS-derivatization was, BSTFA was not added for two 2—2 samples (and one ricinoleic acid standard). Samples were injected into a SP2330 fused silica capillary column (30 m, 0.25 mm ID, 0.20 mm film, Supelco). The temperature program was 100° C. to 150° C. (20° C./min), 150° C. for 6 min, up to 190° C. (4 ° C./min), down to 100° C. (20 ° C./min). A Hewlett-Packard 5971 series mass selective detector was used in place of the flame ionization detector used in the previous experiment. Three hexane blanks were injected between the standard and the wild-type control, and before the 2—2 samples.

Figure 21:
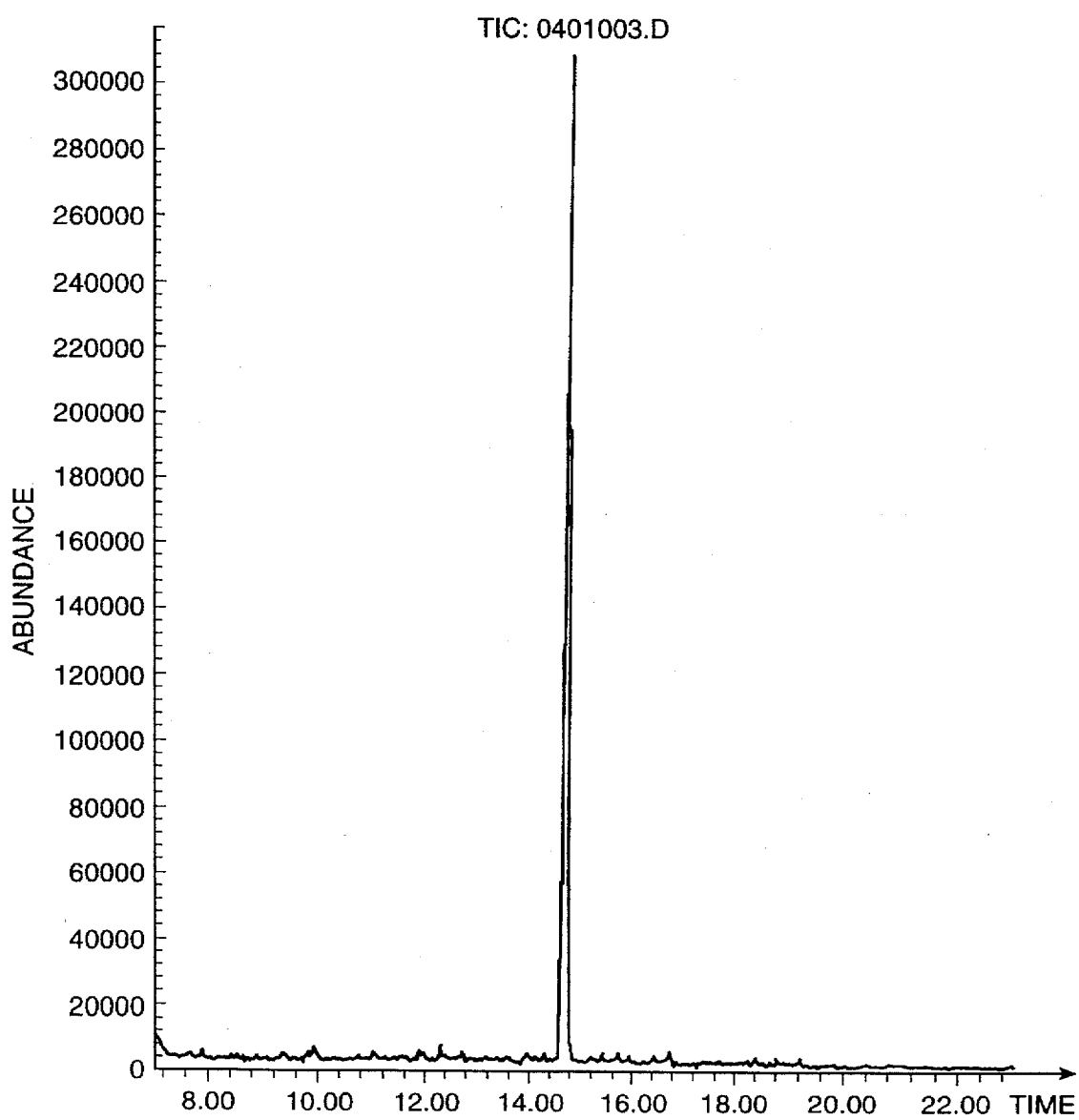
FIG. 21. Gas chromatogram of methyl-ricinoleate standard.
Figure 22:
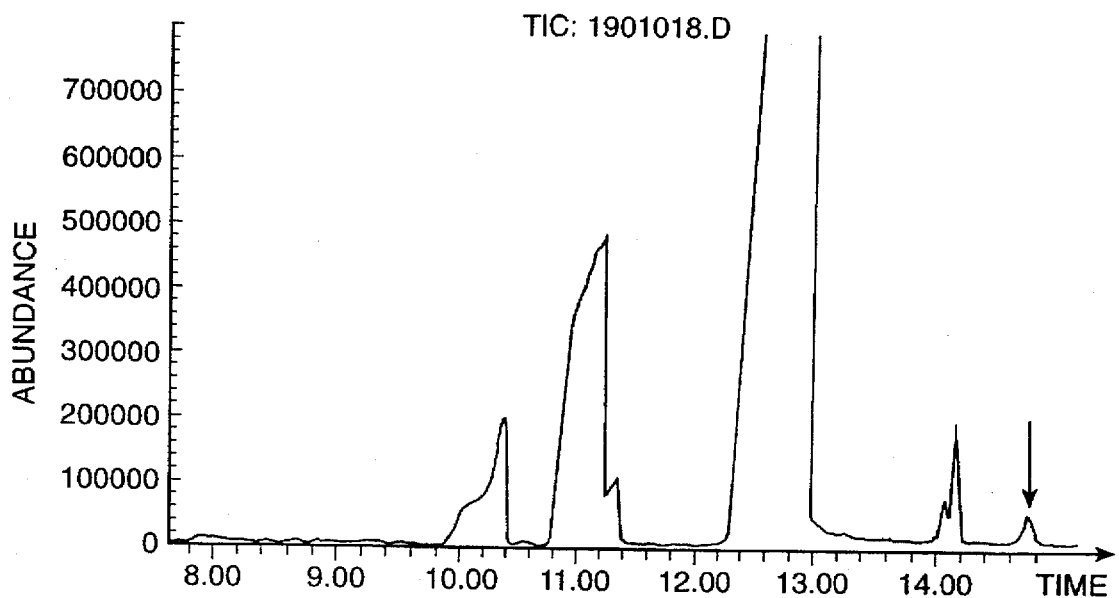
FIG. 22. Total ion chromatogram of fatty acids from seeds of 2—2 transgenic tobacco plants expressing the fah12 gene. The methyl-ricinoleate peak is indicated with an arrow.
Figure 23:
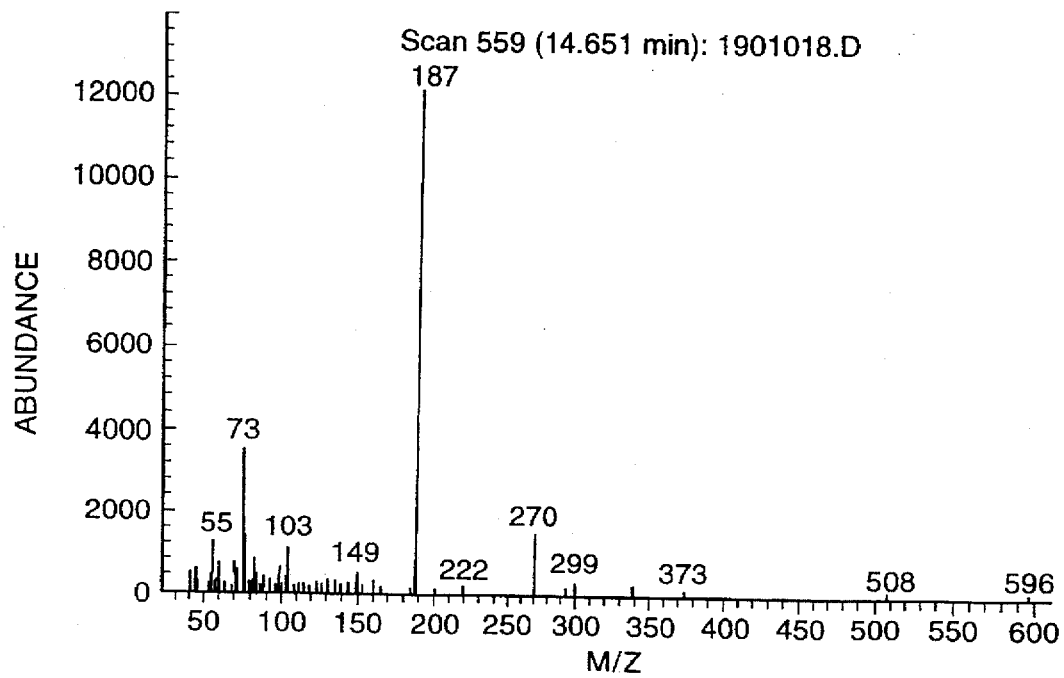
FIG. 23. Mass spectrum of methyl-ricinoleate peak from peak eluting at 14.65 min in FIG. 22.

Grinding the seeds in chloroform:methanol did not result in any significant increase in fatty acid concentrations in the samples. As shown in FIG. 21, TMS-methyl-ricinoleate eluted after 14.602 minutes in this experiment. In five out of seven cases, TMS-methyl-ricinoleate was detected in the 2—2 samples. In two cases the TMS-methyl ricinoleate peak was obscured by a peak of other material that eluted nearby. The TMS-methyl ricinoleate peak was never detected in wild-type samples. One example of the total ion chromatogram for one of the 2—2 sample is shown in FIG. 22. At time 14.651 minutes, a signal was detected which corresponded to the ion spectrum shown on FIG. 23. The standard TMS-methyl-ricinoleate profile in FIG. 24 is given for a comparison. Three characteristic peaks at M/Z 187, 270 and 299 were consistently present in the mass spectrums when ricinoleic acid was detected. A confounding unknown compound elutes after 14.63 minutes in both wild-type and transgenic seeds. However, its mass spectrum is unequivocally different from TMS-methyl-ricinoleate; in particular, the M/Z=270 ion is totally absent (not shown). The presence of this compound as well as inefficient TMS-derivatization precluded detection of TMS-methyl-ricinoleate in two of the 2—2 samples.

These results unequivocally demonstrate the identity of the fah12 cDNA as encoding an oleate hydroxylase. These results also demonstrate that the hydroxylase can be functionally expressed in a heterologous plant species in such a way that the enzyme is catalytically functional. These results also demonstrate that expression of this hydroxylase gene leads to accumulation of ricinoleate in a plant species that does not normally accumulate hydroxylated fatty acids in extractable lipids.

Although the amount of ricinoleate produced in this example is less that desired for commercial production of ricinoleate and other hydroxylated fatty acids from plants, modifications may be made that will increase the level of accumulation of hydroxylated fatty acids in plants that express the fah12 or related hydroxylase genes. Improvements in the level and tissue specificity of expression of the hydroxylase gene are contemplated. Methods to accomplish this by the use of strong, seed-specific promoters such as the B. napus napin promoter will be evident to one skilled in the art. Additional improvements resulting from increases in the amount of substrate are also envisioned. The substrate for the hydroxylase is currently believed to be oleate or other monounsaturated fatty acid esterified to phosphatidylcholine. Therefore, expression of the hydroxylase gene in plant species or particular cultivars that contain elevated levels of oleate-containing phospholipids is believed to lead to increased accumulation of hydroxylated fatty acids. It is also contemplated that the results may be improved by modification of the enzymes which cleave hydroxylated fatty acids from phosphatidylcholine, reduction in the activities of enzymes which degrade hydroxylated fatty acids and replacement of acyltransferases which transfer hydroxylated fatty acids to the sn-1 and sn-3 positions of glycerolipids. Although genes for these enzymes are not currently available, their utility in improving the level of production of hydroxylated fatty adds will be evident based on the results of biochemical investigations of ricinoleate synthesis.

EXAMPLE 2

Production of Ricinoleate in *Arabidopsis thaliana*

In order to verify that the fah12 gene can be functionally expressed in other plant species than tobacco, and to demonstrate that increases in the amount of oleate can affect levels of accumulation of ricinoleate, both wild type and the fad2 mutant of *Arabidopsis thaliana* (L.) were transformed with the pFL2 plasmid containing the oleate hydroxylase cDNA insert. This plasmid was previously used to transform *Nicotiana tabacum* and is described above.

Inoculums of Agrobacterium tumefaciens strain GV3101, previously transformed with pFL2 (see transformation procedure above) were plated on kanamycin LB plates and incubated for 2 days at 30° C. Single colonies were used to inoculate large liquid cultures (LB medium with 50 mg/l rifampicin, 110 mg/l gentamycin and 200 mg/l kanamycin) to be used for the transformation of Arabidopsis plants.

Arabidopsis plants were transformed by the in planta transformation procedure essentially as described by Bechtold et al., (1993). Cells of A. tumefaciens GV3101(pFL2) were harvested from liquid cultures by centrifugation, then resuspended in infiltration medium at $OD_{600}=0.8$ (Infiltration medium was Murashige and Skoog macro and micronutrient medium containing 10 mg/l 6-benzylaminopurine and 5% glucose). Batches of 12–15 plants were grown for 3 to 4 weeks in natural light at a mean daily temperature of approximately 25° C. in 3.5 inch pots containing soil. The intact plants were immersed in the bacterial suspension then transferred to a vacuum chamber and placed under vacuum produced by a laboratory vacuum pump until tissues appeared uniformly water-soaked (approximately 10 min). The plants were grown at 25° C. under continuous light (100 μmol $m^{-2}s^{-1}$ irradiation in the 400 to 700 nm range) for four weeks. The seeds obtained from all the plants in a pot were harvested as one batch. The seeds were sterilized by sequential treatment for 2 min with ethanol followed by 10 min in a mixture of Bleach, water and Tween-80 (50%, 50%, 0.05%) then rinsed thoroughly with sterile water. The seeds were plated at high density (2000 to 4000 per plate) along with appropriate control seeds from a known transformed line and a wild type plant, onto agar-solidified medium in 100 mm petri plates containing ½ X Murashige and Skoog salts medium enriched with B5 vitamins and containing kanamycin at 50 mg/l. After a vernalization period of two nights at 4° C., seedlings were grown for a period of seven days until transformants were clearly identifiable as healthy green seedlings against a background of chlorotic kanamycin-sensitive seedlings. The transformants were transferred to soil for two weeks before leaf tissue could be used for DNA and lipid analysis.

DNA may be extracted from young leaves from transformants to verify the presence of an intact fah12 gene. Amplification of the fah12 insert of the pFL2 plasmid may be carried out as described above for tobacco transformants, using the same DNA primers. DNA samples from Arabidopsis lines transformed with the unmodified pBI121 vector and from wild type plants are used as controls, along with appropriate dilutions of pFL2 plasmid DNA preparations. The transformants can be positively identified after visualization of a characteristic 1 kb amplified fragment on an ethidium bromide stained agarose gel.

Leaves and seeds from fah12 transgenic Arabidopsis plants are subsequently analyzed for the presence of ricinoleic acid, using gas chromatography. The same procedure, previously described for tobacco seeds, is used. Fatty acid methyl esters are extracted from 100–200 mg leaf tissue or 10–20 seeds, and any hydroxyl groups derivatized using N, O-bis(Trimethylsilyl)trifluoroacetamide (BSTFA, Pierce). Control silylated FAMEs from wild type and known pBI121 transgenic lines (transformed with unmodified vector) are analyzed along with both types of fah12 transgenic lines, with wild type or fad2 backgrounds. A TMS-methylricinoleate standard is used to determine if novel peaks are due to the accumulation of ricinoleate in the transgenic plant tissue. An equal mass mixture of FAMEs (16:0, 18:0, 18:1, 18:2, 18:3, Sigma) is also injected to identify any modification in fatty acid composition due to the expression of fah12.

The average fatty acid composition of leaves in Arabidopsis wild type and fad2 mutant lines was reported by Miquel and Browse (1992). Fatty acid composition of the different seed lipid fractions was reported by Kunst et al., (1992). In contrast with tobacco seeds, 20:1 and 22:1 fatty acids accumulate in Arabidopsis seeds. Due to the presence in these fatty acids of a double bond on carbon 9, it is believed that they constitute a new substrate for the oleate-12-hydroxylase encoded by fah12. Studies on the possible substrates for the castor hydroxylase have shown that monounsaturated fatty acids of diverse chain lengths can be hydroxylated, and that the hydroxyl group is always placed three carbons distal to the double bond (Howling et al., 1972). Although oleate was shown be preferred as a substrate, 20:1 and 22:1 should be hydroxylated in transgenic Arabidopsis seeds, as they only differ from oleate by the number of carbon atoms between the double bond and their methyl end. However, it is believed that the amount of hydroxylation of these fatty acids should be relatively low because they are not normally esterified to the sn-2 position of phospholipids in Arabidopsis, the preferred substrate for the castor hydroxylase. This limitation can be overcome by introducing a gene for an sn-2 acyltransferase that does not exclude 20:1 and 22:1 from the sn-2 position of glycerolipids.

The presence of ricinoleate in the leaves or in the seeds may be verified in all cases by mass spectrometry, using the method described above (see Example 1). Similarly, any late-eluting compound found in chromatograms from transgenic lines but not in the controls may also be subjected to mass-spectrometry, and mass-spectra analyzed for the presence of ions characteristic of TMS-derivatized hydroxylated fatty acids. It is contemplated that higher levels of oleate in fad2 mutants increase the level of accumulation of ricinoleic acid.

This example illustrates, in a different plant system, the expression of the fah12 gene encoding an active castor oleate-12-hydroxylase. Although Arabidopsis is not an economically important plant species, it is widely accepted by plant biologists as a model for higher plants. Therefore, this example demonstrates the general utility of the invention described here to the modification of oil composition in higher plants. One advantage of studying the expression of this novel gene in Arabidopsis is the existence in this system of a large body of knowledge on lipid metabolism, as well as the availability of a collection of mutants which can be used to provide useful information on the biochemistry of fatty acid hydroxylation in plant species. Another advantage is the ease of transposing any of the information obtained on metabolism of ricinoleate in Arabidopsis to Brasslea species such as the crop plant *Brassica napus* in order to mass produce ricinoleate for industrial use.

EXAMPLE 3

Obtaining Other Plant Fatty Acyl Hydroxylases

Having obtained sequence (amino acid and DNA) for castor oleate hydroxylase, fatty acyl hydroxylase genes from other plant sources can be readily isolated. In this example, three methods are described to isolate other hydroxylase genes: (A) by DNA hybridization techniques using sequences or peptide sequence information from the castor hydroxylase gene, (B) by polymerase chain reaction based on sequence similarities between the castor oleate hydroxylase gene and the Arabidopsis Δ12 desaturase, and (C) by immunological cross-reactivity using antibodies to the castor protein as a probe.

In any of these methods, cDNA or genomic libraries from the desired plants are generally necessary. Many methods of constructing cDNA or genomic libraries are provided in the scientific literature (for example see Huyuh et at., 1985) and many kits for synthesis of cDNA libraries are available commercially (eg. In Vitrogen, Pharmacia, Stratagene).

Isolation of Hydroxylase Genes by Heterologous Hybridization

The full-length cDNA done for the castor hydroxylase is a preferred heterologous hybridization probe. However, fragments of the cDNA are also useful as heterologous hybridization probes. In order to determine if the castor cDNA is a suitable probe for a given species, Northern analysis of RNA from various tissues of the target plant species is conducted to determine appropriate hybridization conditions. Since hydroxylated fatty adds generally accumulate preferentially in seeds but not in leaves, RNA is isolated from developing embryo tissues and leaves as described in Example 1, electrophoresed in a formaldehyde/agarose gel and transferred to a nylon membrane filter as described in Example 1. The $^{32}$P-labeled oleate hydroxylase probe (Sambrook et al., 1989) is added to a hybridization solution containing 50% formamide, 6×SSC (or 6×SSPE), 5×Denhardt's reagent, 0.5% SDS, and 100 5µg/ml denatured salmon sperm DNA fragments. The hybridization solution containing the labeled probe is incubated with the Northern filter at approximately 40° C. for 18 hours or longer to allow hybridization of the probe to sequences which show regions of significant homology (more than about 60% identity). The filter is then washed at low stringency (room temperature to 42 ° C. in 1X SSC). After exposing the filter to an X-ray film for various amounts of time, stringency conditions can be adjusted by decreasing the amount of formamide progressively to zero and duplicate filters probed until a limited number of distinct bands can be reproducibly detected. The presence of a higher degree of hybridization to the lane of RNA from tissues that accumulate hydroxylated fatty acids is taken as preliminary evidence that the probe is detecting transcripts from a hydroxylase gene.

If one or several mRNA species do hybridize to the DNA probe under the chosen stringency conditions, a cDNA library (or genomic library) is then constructed from the target plant tissue using purified poly-A RNA (hisant and Houdebine, 1990) that was isolated at the stage when hydroxylation of fatty acids is known to occur. The cDNA library is screened using labelled fah12 cDNA as a probe under conditions established for Northern blots. As mentioned above, a number of methods exist for labelling the DNA fragment, utilizing for example $^{32}$P or digoxigenin-labelled deoxynucleotides. Typically, 50,000 to 100,000 plaques are plated on an E. coli host strain (eg. strain XL1-blue would be a suitable host if the Stratagene λZapII vector is used for constructing the library). After transfer of the plaques onto Nylon membranes, hybridization to the probe is carried out in the appropriate hybridization buffer, for example 4×SET, 0.2% SDS, 0.1% sodium pyrophosphate and 100 mg/ml heparin (see Southern hybridization section above), for a period of 16 to 24 hours. Again, care should be taken to choose low stringency conditions including the appropriate hybridization temperature, such as 55° C., and subsequent washing conditions (room temperature to 55° C. in 1–2×SSC). Several adjustments may have to be made until only a small number of phage clones are detected which can be analyzed further. Sequence information should be collected at this point on isolated clones (see Example 1) to verify that they encode a related fatty acid hydroxylase. In this case a full-length cDNA should be isolated from the library for the production of transgenic plants which can in turn be analyzed for any accumulation of hydroxylated fatty acids (see examples 1 and 2). Similar procedures are followed for the production and screening of a genomic library. The genomic clone can also be used for the production of hydroxylated fatty acids in transgenic plants when expressed either under its own promoter or under the control of another promoter such as the B. napus napin promoter, the Arabidopsis 12S promoter, the soybean 7S storage protein promoter or any of the many other promoters which have been characterized.

It is contemplated that, genes encoding Δ12-desaturase may also be detected and recovered due to sequence hornology between the Δ12 desaturase and 12-hydroxylase genes. Hydroxylase and desaturase genes can be distinguished by cloning and sequencing the corresponding cDNA clones and comparing them to the known hydroxylase and desaturase genes. Hydroxylase genes can be recognized by having a higher degree of overall sequence identity to the castor oleate hydroxylase gene than to the Arabidopsis Δ12 desaturase gene.

Isolation of Hybridization Probes by PCR Methods

An alternative approach to heterologous hybridization is to amplify the target gene using degenerate PCR primers. Based on the high degree of amino acid sequence identity between the Arabidopsis fad2 gene and the castor oleate hydroxylase, probes for oleate hydroxylases can be obtained by preparing mixed oligonucleotides of greater than 10, preferably of 15 or more, nucleotides in length representing all possible nucleotide sequences which could encode the corresponding amino acid sequences. This method is clearly documented by Gould et al. (1989). Typically, mixed oligonucleotide primers of 15 to 40 nucleotides are used in PCR reactions. For example the following oligonucleotide pairs (or fragments thereof) are contemplated as generally useful to amplify a 0.65 kb fragment of cDNAs for acyl hydroxylases from other plants. These primers may also be used to amplify a ≧0.65 kb genomic fragment from other species (the exact size of a genomic clone cannot be determined beforehand because the size and position of introns in the genome of these species is not known).

PRIMER- 1:
5'-TGGAA(GA)TA(CT)(TA)(GC)(AGCT)CA(CT)(AC)G (AGCT)(AC) G( ACGT)CA( A C)CA-3'

PRIMER-2:
5'AA(GACT)A(AG)(AG)TG(AG)TG(ACGT)GC(ACGT) AC(AG)TG(ACGT) GT(AG)TC-3' (SEQ ID NOS: 47 and 48)

These examples are intended only to illustrate the method and are not intended to be an exhaustive list of all possible oligonucleotide primers that would be suitable for this purpose. Typically, one skilled in the art would prepare a number of such primers based on the regions of conserved sequence between the castor fah12 and Arabidopsis (or other) Δ12 desaturase gene products, and would then test various combinations of these primers for their ability to produce a PCR product of the expected size. When a PCR product of the expected size was produced, the band would be excised from an agarose gel, cloned and the nucleotide sequence determined. As noted above, comparison of the sequence of the fragment permits identification of the fragment as being part of a hydroxylase gene or a desaturase gene. The cloned fragment may then be used as a hybridization probe under conditions of high stringency (ie., 68° C. in 5×SCC) to isolate cDNA or genomic clones from the target species. As noted above, these clones may be identified as hydroxylase or desaturase dones by sequence similarity to known hydroxylase and desaturase genes. The identity of a particular done is then verified by expression of the done in a suitable transgenic host as described in Example 1. The choice of a suitable host for expression of the gene is mediated by the availability in the host of the substrate for the hydroxylase enzyme and the ability to transform the particular host. In view of recent progress in transforming many plant species, methods of transformation are not thought to be a limitation.

Use of Immunological Methods to Identify Hydroxylase Genes

Acyl hydroxylase genes can also be identified by immunological cross-reactivity using antibodies to the enzyme as a probe. This experiments involves three steps: (1) isolation of large quantities of the castor protein from recombinant *E. coli* strains for the fah12 gene or from castor; (2) production of antibodies against the protein by inoculated rabbits; (3) using the labelled antibodies as a probe on an expression library of mRNA sequences from the target plant. Because of the relative ease of production of large quantities of protein from a cloned gene, the use of recombinant protein is the preferred method.

In the first step, the fah12 insert of the pFL2 clone can be transferred by appropriate cloning techniques into one of the numerous commercially available plasmid expression vectors (such as the pET3; Fox et al., 1993), then transformed into the appropriate *E. coli* strain (Fox et al., 1993). Sequences on the vector, such as appropriate transcription/ translation termination sequences downstream of the insert and promoter sequences upstream (such as the lac promoter) should be present to allow regulated accumulation of recombinant protein.

After growing large liquid cultures of the recombinant strain, a variety of protein purification techniques can be used. Typically, proteins accumulated in *E. coli* inclusion bodies are released and collected after lysis of the cells by a centrifugation step. In the second step, rabbits are serially injected using native or denatured proteins. Antibodies can be recovered from the immunized rabbit sera, using for example beads coated with protein A, a component of the cell wall of *S. aureus* that bind strongly to the constant region of the IgG heavy chain. Alternatively, antibodies can be purified by affinity to antigen immobilized on nitrocellulose filters. The suitability of the purified antibody as a probe should then be tested by hybridizing it sequentially to denatured castor proteins, in vitro translation products of the original fah12 mRNA and to translated vector sequences.

Before constructing a cDNA expression library from which cDNAs clones encoding a novel hydroxylase may be isolated, the produced antibodies should be probed onto a Western blot carrying bound proteins from the target plant. To that effect, an appropriate amount of tissue yielding about 100 µg of proteins is ground in liquid nitrogen, then dispersed in suspension buffer (0.1M NaCl, 0.01 M Tris. HCl (pH 7.6), 0.001M EDTA (pH 8.0), 1 µg/ml aprotinin, 100 µg/ml PMSF) before being added to an equal volume of 2×SDS gel-loading buffer (100 mM Tris. Cl (pH 6.8, 200 mM DDT, 4% SDS, 0.2% BPB, 20% glycerol). After sonication, the sample is added to an SDS-acrylamide gel of the appropriate concentration (10% acrylamide for example). After electrophoresis and staining of the gel, the separated proteins can be transferred onto a nitrocellulose filter which will be incubated in hybridization buffer containing the hydroxylase-raised antibody.

First, hybridization is carried out in a 1:100 to 1:5000 solution of the antibody in the following buffer: 5% nonfat dried milk, 0.01% antifoam A, 0.02% sodium azide in PBS). The incubation temperature is 4° C. In order to increase the sensitivity of the detection, which is important in the present case of heterologous antibody-antigen hybridization, increasing incubation times would be explored to determine the optimum conditions.

After this primary incubation, the antibody-antigen complexes can be detected in a variety of ways, using $^{125}I$-labelled anti-immunoglobin or protein A, or more commonly one of these two secondary reagent conjugated to horseradish peroxidase or alkaline phosphatase. In the latter case, the appropriate substrate to the conjugated enzyme is added prior to exposure of the filter to X-ray films.

In the case when one or several protein species can be detected on the western blot, an expression cDNA library can be constructed with purified polyA RNA from tissue(s) accumulating the hydroxylated fatty acid. cDNAs should preferentially be cloned in a bacteriophage vector rather than a plasmid vector, as larger numbers of clones can conveniently be screened. As an example, lambda gt11 and its derivatives can be used (Huyuh et al., 1985). In these vectors expression of cloned cDNA species is under the control of the lac repressor. Again, a typical 50,000 to 100,000 clones can be screened for expression of a fatty acyl hydroxylase. In the presence of IPTG, recombinant phages express the foreign gene, and the resulting proteins can be imprinted on nitrocellulose filters for subsequent western hybridization, in the conditions described above. As mentioned in the previous section describing how labelled DNA probes can be used, positive clones should then be analyzed further to determine if they do encode an hydroxylase with similarity to the castor enzyme.

It is contemplated that the foregoing methods can be used to allow the isolation of acyl hydroxylase genes from species other than castor where hydroxylated fatty acids can be found. As mentioned earlier, at least 33 structurally distinct monohydroxylated plant fatty acids have been described (Gunstone et al., 1986; Smith, 1985; van de Loo et al., 1993). The approaches described above can be of utility to isolate the genes encoding the corresponding hydroxylases. These species would be of primary interest for the isolation of genes related to fah12, especially the species in the Lesquerella genus. Members of this genus accumulate oil, which like castor oil, contains a hydroxyl group on the fatty acid three carbons distal to the first double bond from the carboxy end. *Lesquerella densipila* is of particular interest since it accumulates the 16 carbon hydroxy fatty acid equivalent of ricinoleic acid. Similarly, this species also accumulates a di-unsaturated version of ricinoleic lo acid. The enzyme involved in the biosynthesis of the isomer isoricinoleic acid in Strophanthus species is also expected to have structural and catalytic similarity to the castor oleate-12-hydroxylase. In that case, the hydroxyl group and the double bond are inverted with respect to ricinoleic acid.

Clones identified using DNA hybridization or immunological screening techniques are then purified, the DNA isolated, and the sequence of the genes is determined as described in Example 1. In this manner, it is verified that the clones encode a related fatty acyl hydroxylase. The newly isolated plant hydroxylase sequences can also be used to isolate genes for fatty acyl hydroxylases from other plant species using the techniques described above.

The above examples demonstrate critical factors in the production of hydroxylated fatty acids. A complete cDNA sequence of the castor oleate hydroxylase is also provided with a demonstration of the activity of the polypeptide encoded thereby in transgenic plants. A full sequence of the castor hydroxylase is also given with various constructs for use in host cells. Through this invention, one can obtain the amino acid and nucleic acid sequences which encode plant fatty acyl hydroxylases from a variety of sources and for a variety of applications. Accordingly, within its various embodiments, it will be appreciated that the invention includes such features as: recombinant DNA constructs comprising at least a portion of a plant fatty acyl hydroxylase encoding sequence, preferably but not necessarily a plant oleate hydroxylase encoding sequence; transgenic host cells including such construct and containing an expressed plant fatty acyl hydroxylase; methods of producing plant hydroxylase in such host cells or progeny thereof; methods of increasing the fatty acid content in plant cells or in triglycerides produced from plants, e.g. oilseed crop plants, using the present constructs. Oilseed crop plants which are contemplated include rapeseed, Canola, flax, sunflower, safflower, cotton, cuphea, soybean, peanut, coconut, oil palm and corn. Other features of the invention such as the possibility of using constructs according to the invention or nucleotides or deduced amino acid sequences derived therefrom to identify and isolate acyl hydroxylase genes from plant species other than *Ricinus communis* (L), will also be evident from the foregoing.

All publications mentioned in this specification are indicative of the level of skill of those skilled in the art to which this invention pertains. All publications are herein incorporated by reference to the same extent as if each individual publication was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

REFERENCES

Altschul, S. F., Gish, W., Miller, W., Myers, E. W., Lipman, D. J. (1990) Basic local alignment search tool, J. Mol. Biol., 215, 403–410.

Arondel, V., Lemieux, B., Hwang, I., Gibson, S., Goodman, H. M., Somerville, C. R. (1992) Map-based cloning of a gene controlling omega-3 fatty acid desaturation in Arabidopsis. Science 258, 1353–1355.

Atsmon, D. (1989) Castor, in *Oil Crops of the World*, Robbelen, G., Downey, K. R., and Ashri, A., Eds., McGraw-Hill, New York, pp. 438–447.

Bafor, M., Smith, M. A., Jonsson, L., Stobart, K., Styme, S. (1991) Ricinoleic acid biosynthesis and triacylglycerol assembly in microsomal preparations from developing castor-bean (*Ricinus communis*) endosperm. Biochem. J. 280, 507.

Battey, J. F., Ohlrogge, J. B. (1989) A comparison of the metabolic fate of fatty acids of different chain lengths in developing oilseeds. Plant Physiol. 90, 835–840.

Bechtold, N., Ellis, J. and Pelletier, G. (1993) In Planta Agrobacterium mediated gene transfer by infiltration of adult *Arabidopsis thaliana* plants. C. R. Acad. Sci. Paris 316, 1194–1199.

Beltz, G. A., Jacobs, K. A., Eickbuch, T. H., Cherbas, P. T., Kafatos, F. C. (1983) Isolation of multigene families and determination of homologies by filter hybridization methods. Methods in Enzymology 100, 266–285.

Bray, E. A., Naito, S., Pan, N. S., Anderson, E., Dube, P., Beachy, R. N. (1987) Expression of the β-subunit of β-conglycinin in seeds of transgenic plants. Planta 172:364–370.

Browse, J., Somerville, C. (1991) Glycerolipid synthesis: biochemistry and regulation. Ann. Rev. Plant Physiol. Plant Mol. Biol. 42, 467.

Canvin, D. T. (1963) Formation of oil in the seed of *Ricinus communis* L., Can. J. Biochem. Physiol. 41, 1879–1885.

Ditta, G., Stanfield, S., Corbin, D., Helinski, D. R. (1980) Broad host range DNA cloning system for gram-negative bacteria: Construction of a gene bank of *Rhizobium meliloti*. Proc. Natl. Acad. Sci. USA 77,7347–7351.

Fox B. C., Shanklin, J., Somerville, C., Munck, E. (1993) Stearoyl-acyl carrier protein $\Delta^9$ desaturase from *Ricinus communis* is a diiron-oxo protein. Proc. Natl. Acad. Sci., 90, 2486–2490.

Galliard, T., and Stumpf, P. K. (1966) Fat metabolism in higher plants XXX. Enzymatic synthesis of ricinoleic acid by a microsomal preparation from developing *Ricinus communis* seeds. J. Biol. Chem. 241, 5806.

Gould, S. J., Subramani, S., Scheffler, I. E. (1989) Use of the DNA polymerase chain reaction for homology probing. Proc. Natl. Acad. Sci. USA 86, 1934–1938.

Greenwood, J. S., Bewley, J. D. (1982) Seed development in *Ricinus communis* (castor bean). I. Descriptive morphology, Can. J. Bot., 60, 1751–1760.

Gunstone, F. D., Harwood, J. L., Padley, F. B. (1986) *The Lipid Handbook*, Chapman and Hall, London, chapters 1.9 pp 19–20 and 3.3.5 pp 57–58.

Howling, D., Morris, L. J., Gurr, M. I., James, A. T. (1972) The specificity of fatty acid desaturases and hydroxylases. The dehydrogenation and hydroxylation of monoenoic acids, Biochim. Biophys. Acta 260, 10.

Huyuh, T. V., Young, R. A., Davis, R. W. (1985) Constructing and screening cDNA libraries in λgt10 and λgt11. In DNA Cloning, Vol. 1: A Practical Approach, (ed) D. M. Glover. IRL Press, Washington DC pp 49–77.

Iba, K., Gibson, S., Nishiuchi, T., Fuse, T., Nishimura, M., Arondel, V., Hugly, S., and Somerville, C. (1993) A gene encoding a chloroplast omega-3 fatty acid desaturase complements alterations in fatty acid desaturation and chloroplast copy number of the fad7 mutant of *Arabidopsis thaliana*. J. Biol. Chem. 268, 24099–24105.

James, A. T. Hadaway, H.C., Webb, J. P. W. (1965) The biosynthesis of ricinoleic acid, Biochem. J. 95, 448–452.

Kearns, E. V., Hugly, S., Somerville, C. R. (1991) The role of cytochrome $b_5$ in Δ12 desaturation of oleic acid by microsomes of safflower (*Carthamus tinctorius* L.), Arch. Biochem. Biophys. 284, 431–436.

Knutson, D. S., Thompson, G. A., Radke, S. E., Johnson, W. B., Knauf, V. C., Kridl, J. C. (1992) Proc. Natl. Acad. Sci. USA 89, 2624–2628.

Kok, M., Oldenhuis, R., van der Linden, M. P. G., Raatjes, P., Kingma, J., van Lelyveld, P. H., Witholt, B. (1989) The *Pseudomonas oleovorans* alkane hydroxylase gene: sequence and expression. J. Biol. Chem. 264, 5435–5441.

Koncz, C., Schell, J. (1986) The promoter of $T_L$-DNA gene 5 controls the tissue-specific expression of chimeric genes carried by a novel type of Agrobacterium binary vector. Mol. Gen. Genet. 204, 383–396.

Křen, V., Řezanka, T., and Řeháček, Z. (1985) Occurrence of ricinoleic acid in submerged cultures of various Claviceps sp., Experentia 41, 1476–1477.

Miquel, M. Browse, J. (1992) Arabidopsis mutants deficient in polyunsaturated fatty acid synthesis. J. Biol. Chem. 267, 1502–1509.

Moreau, R. A., Stumpf, P. K. (1981) Recent studies of the enzymic synthesis of ricinoleic acid by developing castor beans, Plant Physiol. 67, 672.

Morris, L. J. (1967) The mechanism of ricinoleic acid biosynthesis in Ricinus communis seeds. Blochem. Biophys. Res. Commun. 29, 311.

Morris, L. J. (1970) Mechanisms and stereochemistry in fatty acid metabolism. Blochem. J. 118, 681–693.

Morris, L. J., Hall, S. W., James, A. T. (1966) The biosynthesis of ricinoleic acid by Claviceps purpurea. Biochem. J. 100, 29c–30c.

Newman, T. C., Ohme-Takagi, M., Taylor, C. B., Green, P. J. (1993) DST sequences, highly conserved among plant SAUR genes, target reporter transcripts for rapid decay in tobacco. Plant Cell 5, 701–714.

Okuley, J., Lightner, J., Feldman, K., Yadav, N., Lark, E., Browse, J. (1994) Arabidopsis FAD2 gene encodes the enzyme that is essential for polyunsaturated lipid synthesis. Plant Cell 6, 147–158.

Ooms, G., Hooykaas, P. J. J., van Veen, R. J. M., van Beelen, P., Regensburg-Tuink, T. J. G., Schilperoort, R. A. (1982) Octopine Ti-plasmid deletion mutants of Agrobacterium tumefaciens with emphasis on the right side of the T-region. Plasmid 7, 15–29.

Panaccione, D. M., Hanau, R. M. (1990) Characterization of two divergent β-tubulin genes from Colletotrichum graminicola, Gene 86, 163–170.

Prasad, R. B. N., Rao, Y. N., and Rao, S. V. (1987) Phospholipids of palash (Butea monosperma), papaya (Carica papaya), jangli badam (Sterculia foetida), coriander (Coriandrum sativum) and carrot (Daucus carota) seeds. J. Am. Oil Chem. Soc. 64, 1424.

Puissant, C., Houdebine, L. (1990) An improvement of the single-step method of RNA isolation by acid guanidinium thiocyanate-phenol-chloroform extraction. BioTechniques 8, 148–149.

Sambrook, J., Fritsch, E. F., and Maniatis, T., Molecular Cloning: a Laboratory Manual, 2nd ed., Cold Spring Harbor Laboratory Press, 1989.

Schmidt, H., Sperling, P, Heinz, E. (1993) New in vitro and in vivo evidence for lipid-linked desaturation in plants. In Biochemistry and Molecular Biology of Membrane and Storage Lipids of Plants, eds, N. Murata and C. R. Somerville, American Society of Plant Physiologists, pp 40–49.

Smith C. R., Jr. (1985) Unusual seed oils and their fatty acids, in Fatty Acids, Pryde E. H., Ed., American Oil Chemists' Society, Champaign, Second edition, pp 29–47.

Smith, M. A., Jonsson, L., Stymne, S., Stobart, K. (1992) Evidence for cytochrome $b_5$ as an electron donor in ricinoleic acid biosynthesis in microsomal preparations from developing castor bean (Ricinus communis L.), Blochem. J. 287, 141–144.

Suzuki, M., Hayakawa, T., Shaw, J. P., Rekik, M., Harayama, S. (1991) Primary structure of xylene monooxygenase: similarities to and differences from the alkane hydroxylation system. J. Bacteriol. 173, 1690–1695.

Thiede, M. A., Ozols, J., Strittmatter, P. (1986) Construction and sequence of cDNA for rat liver stearoyl coenzyme A desaturase. J. Biol. Chem. 261, 13230–13235.

van de Loo, F. J., Fox, B. G., Somerville, C. (1993) Unusual fatty acids, in Lipid Metabolism in Plants, T. S. Moore Jr., Ed., CRC Press, Boca Raton, pp91–126.

van de Loo, F., and Somerville, C. (1994) A plastid omega-3 desaturase from castor (Ricinus communis L.). Plant Physiol 105, 443–444.

von Heijne, G. (1985) Signal sequences. J. Mol. Biol. 184,99–105.

Yadav, N. S., Wierzbicki, A., Aegerter, M., Caster, C. S., Perez-Grau, L., Kinney, A. J., Hitz, W. D., Booth, R., Schweiger, B., Stecca, K. L., Allen, S. M., Blackwell, M., Reiter, R. S., Carlson, T. J., Russell, S. H., Feldmann, K. A., Pierce, J., Browse, J. (1993) Cloning of higher plant ω3 fatty acid desaturases. Plant Physiol. 103, 467–476.

---

What is claimed is:

1. A seed of a transgenic plant, wherein said transgenic plant has integrated in its genome a DNA construct encoding oleate-12 hydroxylase as shown in SEQ ID NO:40, and wherein said DNA construct encoding oleate-12 hydroxylase is transcribed and translated to produce an increased percentage of hydroxylated fatty acids in said seed as compared to a seed of said plant not containing said DNA construct.

2. The seed of claim 1 wherein said DNA construct contains base 187 to base 1347 of SEQ ID NO:39.

3. The seed of claim 1 wherein said plant is selected from the group consisting of rapeseed, Canola, flax, sunflower, safflower, cotton, Cuphea, soybean, peanut, coconut, oil palm, and corn.

4. The seed of claim 1 wherein said DNA construct further comprises a seed-specific promoter.

5. The seed of claim 4 wherein said seed-specific promoter is a napin promoter or a promoter of said oleate-12 hydroxylase.

6. The seed of claim 1 wherein said DNA construct further comprises a cauliflbwer mosaic virus 35S promoter.

7. The seed of claim 1 wherein at least one of said hydroxylated fatty acida is selected from the group consisting of 12-hydroxy-9-octadecenoic acid (ricinoleic acid), 14-hydroxy-11-eicosenoic acid (lesquerolic acid), and 12-hydroxy-9,15-octadecadienoic acid.

8. A seed of a transgenic plant, wherein said transgenic plant has incorporated in its genome a DNA construct encoding oleate-12 hydroxylase into said plant, wherein said DNA construct encodes amino acid sequence SEQ ID NO:40, and wherein said DNA construct encoding oleate-12 hydroxylase is transcribed and translated to produce an increased percentage of a hydroxylated fatty acyl compound in said seed as compared to a seed of said plant not containing said DNA construct.

9. The seed of claim 8 wherein said DNA construct contains base 187 to base 1347 of SEQ ID NOL:39.

10. The seed of claim 8 wherein said plant is selected from the group consisting of rapeseed, Canola, flax, sunflower, safflower, cotton, Cuphea, soybean, peanut, coconut, oil palm, and corn.

11. The seed of claim 8 wherein said DNA construct further comprises a seed-specific promoter.

12. The seed of claim 11 wherein said seed-specific promoter is a napin promoter or a promoter of said oleate-12 hydroxylase.

13. The seed of claim 8 wherein said DNA construct further comprises a cauliflower mosaic virus 35S promoter.

14. The seed of claim 8 wherein said hydroxylated fatty acyl compound comprises a hydroxylated fatty acid selected from the group consisting of 12-hydroxy-9-octadecenoic acid (ricinoleic acid), 14-hydroxy-11-eicosenoic acid (lesquerolic acid), and 12-hydroxy-9,15-octadecadienoic acid.

* * * * *